(12) United States Patent
Park et al.

(10) Patent No.: US 11,871,657 B2
(45) Date of Patent: Jan. 9, 2024

(54) COMPOUND FOR ORGANIC ELECTRIC DEVICE, ORGANIC ELECTRIC DEVICE USING SAME, AND ELECTRONIC DEVICE THEREOF

(71) Applicant: DUK SAN NEOLUX CO., LTD, Cheonan-si (KR)

(72) Inventors: Jong Gwang Park, Cheonan-si (KR); Yun Suk Lee, Seongnam-si (KR); Yu Ri Kim, Wonju-si (KR); Yeon Hee Choi, Cheonan-si (KR); Kyoung Chul Kim, Sejong (KR)

(73) Assignee: Duk San Neolux Co., Ltd.

( * ) Notice: Subject to any disclaimer, the term of this patent is extended or adjusted under 35 U.S.C. 154(b) by 826 days.

(21) Appl. No.: 16/619,236

(22) PCT Filed: Jun. 1, 2018

(86) PCT No.: PCT/KR2018/006290
§ 371 (c)(1),
(2) Date: Dec. 4, 2019

(87) PCT Pub. No.: WO2018/225991
PCT Pub. Date: Dec. 13, 2018

(65) Prior Publication Data
US 2020/0152874 A1    May 14, 2020

(30) Foreign Application Priority Data

Jun. 5, 2017    (KR) .................. 10-2017-0069607

(51) Int. Cl.
*H10K 85/60*    (2023.01)
*C07C 211/61*    (2006.01)
(Continued)

(52) U.S. Cl.
CPC .......... *H10K 85/633* (2023.02); *C07C 211/61* (2013.01); *H10K 50/11* (2023.02);
(Continued)

(58) Field of Classification Search
CPC . C07C 211/61; C07C 217/94; C07C 2603/18; C07C 2603/26; C07C 2603/40;
(Continued)

(56) References Cited

U.S. PATENT DOCUMENTS 10,297,758 B2    5/2019    Lee et al.
10,446,762 B2   10/2019    Kim et al.
(Continued)

FOREIGN PATENT DOCUMENTS

CN    101987822 A   *   3/2011
CN    104781233 A       7/2015
(Continued)

OTHER PUBLICATIONS

WO-2018016786-A1, machine translation (Year: 2018).*
(Continued)

*Primary Examiner* — Dylan C Kershner
*Assistant Examiner* — Elizabeth M. Dahlburg
(74) *Attorney, Agent, or Firm* — Harness, Dickey & Pierce, P.L.C.

(57) ABSTRACT

Compounds capable of improving high luminous efficiency, low driving voltage, and a service life of a device such as an organic electric device and electronic devices that include the organic electric device. The compounds may have a Chemical Formula 1, wherein at least one of $Ar^1$ to $Ar^5$ can be a substituent having Chemical Formula 1-1:

(Continued)

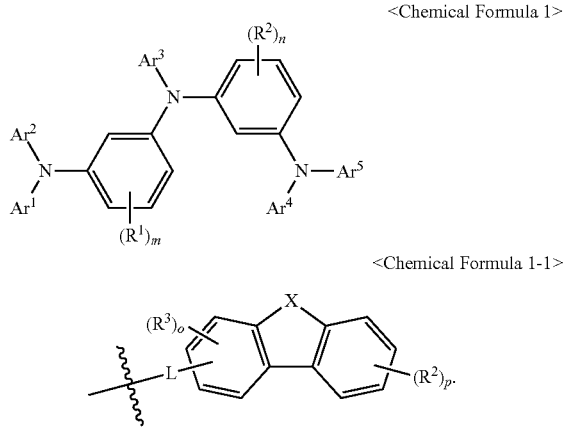

<Chemical Formula 1>

<Chemical Formula 1-1>

11 Claims, 1 Drawing Sheet

(51) Int. Cl.
*H10K 50/11* (2023.01)
*H10K 50/15* (2023.01)
*H10K 50/17* (2023.01)

(52) U.S. Cl.
CPC ............ *H10K 50/15* (2023.02); *H10K 50/17* (2023.02); *H10K 85/624* (2023.02); *H10K 85/626* (2023.02)

(58) Field of Classification Search
CPC ............ C07C 2603/50; C07C 2603/94; H10K 85/615; H10K 85/624; H10K 85/626; H10K 85/631; H10K 85/633; H10K 50/11; H10K 50/15; H10K 50/17; H10K 59/00; C07B 2200/05; Y02E 10/549
See application file for complete search history.

(56) References Cited

U.S. PATENT DOCUMENTS

| | | | |
|---|---|---|---|
| 2015/0069350 A1* | 3/2015 | Kim | C09K 11/06 257/40 |
| 2016/0005981 A1 | 1/2016 | Kim et al. | |
| 2016/0190466 A1* | 6/2016 | Pfister | C07D 405/04 549/330 |
| 2016/0301011 A1 | 10/2016 | Nakaie et al. | |
| 2017/0141311 A1 | 5/2017 | Lee et al. | |
| 2017/0200903 A1 | 7/2017 | Park et al. | |
| 2018/0083204 A1 | 3/2018 | Kim et al. | |
| 2019/0157560 A1 | 5/2019 | Lee et al. | |
| 2019/0173023 A1 | 6/2019 | Kim et al. | |

FOREIGN PATENT DOCUMENTS

| | | | | |
|---|---|---|---|---|
| CN | 105051011 A | | 11/2015 | |
| CN | 105712962 A | | 6/2016 | |
| DE | 10249723 A1 | * | 5/2004 | ............ C08G 61/02 |
| JP | 10265773 A | * | 10/1998 | |
| JP | 2006-195089 A | | 7/2006 | |
| JP | 2006195089 A | * | 7/2006 | |
| JP | 2007-110097 A | | 4/2007 | |
| JP | 2007-219387 A | | 8/2007 | |
| JP | 2012098388 A | * | 5/2012 | |
| KR | 10-2014-0018101 A | | 2/2014 | |
| KR | 10-2016-0067925 A | | 6/2016 | |
| WO | WO-2018-016786 A1 | | 1/2018 | |

OTHER PUBLICATIONS

International Search Report (in English and Korean) and Written Opinion (in Korean) issued in PCT/KR2018/006290, dated Sep. 17, 2018; ISA/KR.
U.S. Appl. No. 16/334,527, filed Mar. 19, 2019, Park et al.
U.S. Appl. No. 16/494,801, filed Mar. 20, 2019, Park et al.
U.S. Appl. No. 16/494,235, filed Sep. 13, 2019, So et al.

\* cited by examiner

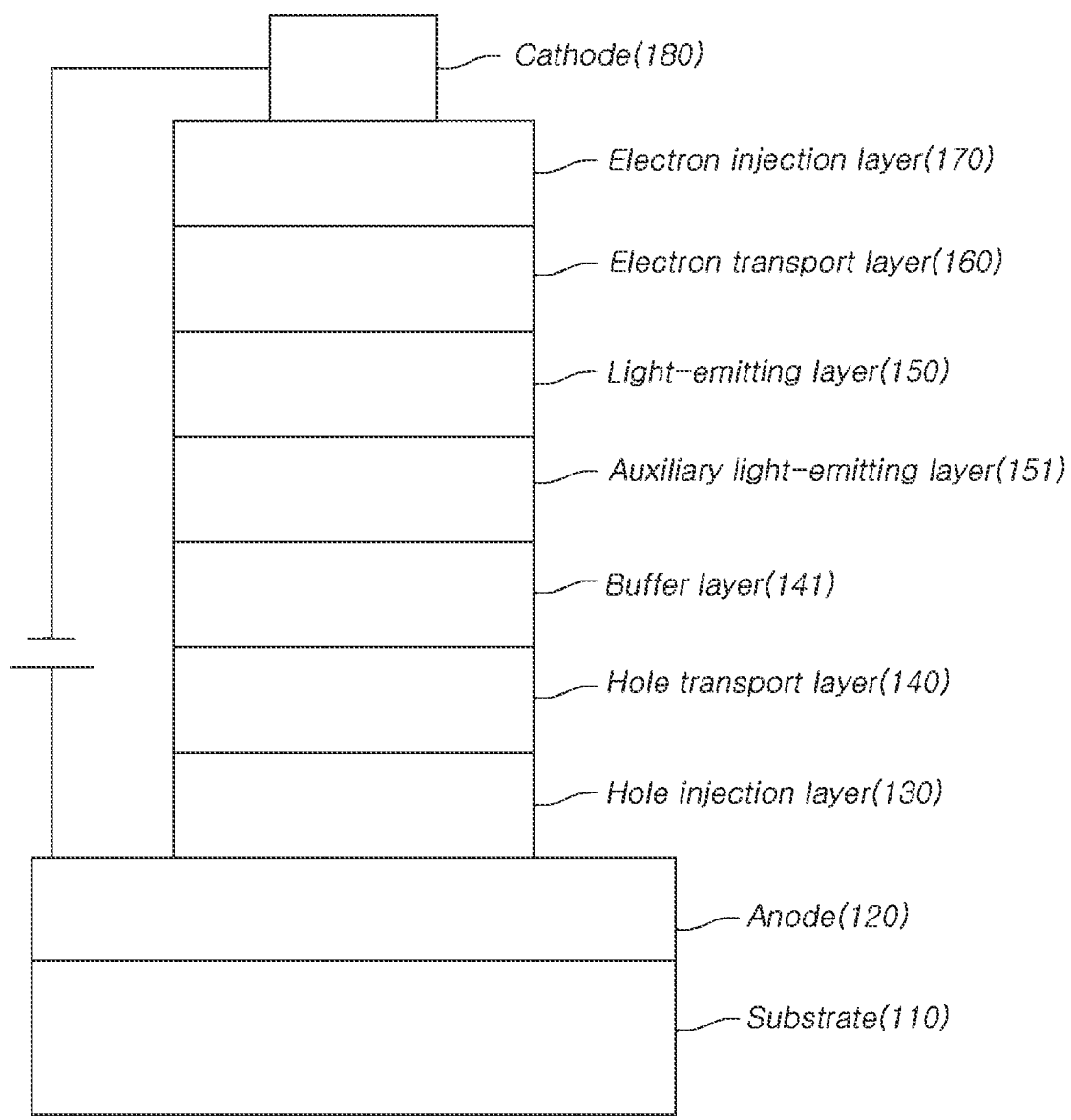

COMPOUND FOR ORGANIC ELECTRIC DEVICE, ORGANIC ELECTRIC DEVICE USING SAME, AND ELECTRONIC DEVICE THEREOF

CROSS-REFERENCE TO RELATED APPLICATIONS

This application is a U.S. National Phase Application under 35 U.S.C. 371 of International Application No. PCT/KR2018/006290, filed on Jun. 1, 2018, which claims the benefit of Korean Patent Application No. 10-2017-0069607, filed on Jun. 5, 2017. The entire disclosures of the above applications are incorporated herein by reference.

TECHNICAL FIELD

The present embodiments pertain to a compound for an organic electric element, an organic electric element using same, and an electronic device thereof.

BACKGROUND ART

In general, an organic light emitting phenomenon refers to the phenomenon of converting electrical energy into light energy by means of an organic material. An organic electric element using an organic light emitting phenomenon is usually structured to include an anode and a cathode, with an organic layer interposed therebetween. The organic layer, for the most part, has a multi-layer structure composed of different materials in order to increase the efficiency and stability of the organic electric element. For example, the organic layer may comprise a hole injection layer, a hole transport layer, a light emitting layer, an electron transport layer and an electron injection layer.

According to functions, the materials used in organic layers of the organic electric element may be classified into a light emitting material and a charge transport material, such as a hole injection material, a hole transport material, an electron transport material, an electron injection material and the like.

The biggest problems with organic electric light-emitting elements include lifespan and efficiency. As large-area displays predominate the market, the efficiency and lifespan problems are the issues that should be solved.

Efficiency, lifespan, and driving voltage are related to each other. As the efficiency increases, the driving voltage decreases relatively, which decreases the crystallization of organic materials due to the Joule heating generated during operation, with the consequent increase of the lifespan.

However, simple improvement of the organic layer does not guarantee maximal efficiency. This is because long life and high efficiency can be achieved at the same time when energy levels, T1 values, and intrinsic properties (mobility, interfacial properties, etc.) between individual organic layers are combined optimally.

In addition, in order to solve the light emission problem with a hole transport layer in an organic electric light-emitting element, an auxiliary light-emitting layer has recently been required to exist between the hole transport layer and the light-emitting layer. Thus, different auxiliary light-emitting layers should be developed for respective individual light-emitting layers (R, G, and B).

As a rule, an electron and a hole recombine to produce an exciton in a light-emitting layer to which the electron and the hole have been transferred from an electron transport layer and a hole transport layer, respectively.

However, materials for use in the hole transport layer are, for the most part, low in T1 value because they must have low HOMO values. Thus, the exciton generated in the light-emitting layer migrates into the hole transport layer, causing a charge unbalance in the light-emitting layer and emitting light at the boundary of the hole transport layer.

Upon light emission at the boundary of the hole transport layer, the organic electric element meets the problem of decreasing in color purity and efficiency and becoming short in lifespan. Therefore, there is an urgent need for development of an auxiliary light-emitting layer having a high T1 value and a HOMO level between the hole transport layer HOMO energy level and the light-emitting layer HOMO energy level.

Meanwhile, there is also a need to develop a hole injection layer material that can retard the penetration and diffusion of a metal oxide from a cathode (ITO) to an organic layer, which is one of the causes of reducing the lifespan of an organic electric element, and exhibits stability against the Joule heating generated during element operation, that is, has a high glass transition temperature. Given a low glass transition temperature, a hole transport layer material degrades the uniformity of the thin film surface upon element operation, which is reported to have a great influence on element lifespan. Moreover, OLEDs are formed mainly using deposition methods. In this regard, a material that can endure long against the deposition, that is, a material highly resistant to heat is required.

Consequently, in order for an organic electric element to sufficiently exhibit excellent properties, materials constituting the organic layers in the element, for example, a hole injection material, a hole transport material, a light-emitting material, an electron transport material, an electron injection material, an auxiliary light-emitting layer material and so forth should be stable and effective in advance. Up to now, however, stable and effective organic layer materials for organic electric elements have not been developed sufficiently. Therefore, there is a continued and desperate need for novel materials particularly for a hole transport layer or an auxiliary light-emitting layer.

DETAILED DESCRIPTION OF THE INVENTION

Technical Problem

In order to solve the above-mentioned problems encountered in the related art, embodiments of the present disclosure have led to the discovery of a compound having a novel structure. Further, it was found that this compound, when applied to an organic electrical element, can significantly improve luminous efficiency, stability, and life span in the element.

Accordingly, a purpose of the present disclosure is to provide a novel compound, an organic electric element using the same, and an electronic device including the organic electric element.

Technical Solution

In accordance with an aspect thereof, the present disclosure provides a compound represented by the following Chemical Formula:

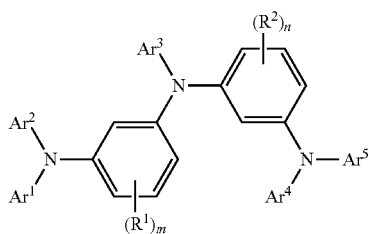

<Chemical Formula 1>

In accordance with another aspect thereof, the present disclosure provides an organic electric element using the compound represented by the Chemical Formula above, and an electronic device thereof.

Advantageous Effects

By employing the compound according to the present disclosure, an element can be endowed with a high luminous efficiency, a low driving voltage, and high thermal resistance and can greatly improve in color purity and lifespan.

BRIEF DESCRIPTION OF THE DRAWINGS

The FIGURE is a schematic cross-sectional view of an organic light-emitting diode according to an embodiment of the present disclosure.

MODE FOR CARRYING OUT THE INVENTION

Hereinafter, some embodiments of the present disclosure will be described in detail with reference to the accompanying illustrative drawing.

In designation of reference numerals to components in the drawings, it should be noted that the same elements will be designated by the same reference numerals although they are shown in different drawings. Further, in the following description of the present disclosure, a detailed description of known functions and configurations incorporated herein will be omitted when it may make the subject matter of the present disclosure rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

As used in this specification and the appended claims, unless otherwise indicated, the meanings of the following terms are as follows.

The term "halo" or "halogen" as used herein refers to fluorine (F), bromine (Br), chlorine (Cl), or iodine (I) unless otherwise indicated.

As used herein, the term "alkyl" or "alkyl group" refers to a saturated aliphatic functional radical of 1 to 60 carbon atoms with a single bond therein, including a straight chain alkyl group, a branched chain alkyl group, a cycloalkyl (alicyclic) group, an alkyl-substituted cycloalkyl group, and a cycloalkyl-substituted alkyl group, unless otherwise indicated.

The term "haloalkyl group" or "halogenalkyl group", as used herein, means a halogen-substituted alkyl group unless otherwise specified.

The term "heteroalkyl group", as used herein, means that at least one of the carbon atoms constituting the alkyl group has been replaced with a heteroatom.

As used herein, the terms "alkenyl group" and "alkynyl group", refer to a straight or branched chain of 2 to 60 carbon atoms with a double and a triple bond therein, respectively, unless stated otherwise, but are not limited thereto.

Unless otherwise stated, the term "cycloalkyl" as used herein refers to an alkyl forming a ring having 3 to 60 carbon atoms, without being limited thereto.

Unless otherwise stated, the term "alkoxyl group", "alkoxy group", or "alkyloxy group" as used herein means an alkyl group of 1 to 60 carbon atoms having an oxygen radical attached thereto, but is not limited thereto.

As used herein, the term "alkenoxyl group", "alkenoxy group", "alkenyloxyl group", or "alkenyloxy group" means an alkenyl group of 2 to 60 carbon atoms having an oxygen radical attached thereto, unless otherwise stated, but is not limited thereto.

As used herein, the term "aryloxyl group" or "aryloxy group" means an aryl group of 6 to 60 carbon atoms having an oxygen radical attached thereto unless otherwise specified, but is not limited thereto.

As used herein, the terms "aryl group" and "arylene group" each refer to having 6 to 60 carbon atoms unless otherwise stated, but are not limited thereto. In the present disclosure, an aryl group or an arylene group means a single or multiple aromatic ring, including an aromatic ring which is formed as neighboring substituents participate in a bond or a reaction. For example, the aryl group may be a phenyl group, a biphenyl group, a terphenyl group, a naphthyl group, an anthracenyl group, a fluorene group, a spirofluorene group, or a spirobifluorene group.

The prefix "aryl" or "ar" means a radical substituted with an aryl group. For example, an arylalkyl group is an alkyl group substituted with an aryl group and an arylalkenyl group is an alkenyl group substituted with an aryl group. In this regard, the radical substituted with an aryl group has the number of carbon atoms described herein.

Also, when prefixes are named consecutively, it means that the substituents are listed in the order described first. By way of example, an arylalkoxy group means an alkoxy group substituted with an aryl group, an alkoxylcarbonyl group means a carbonyl group substituted with an alkoxyl group, and an arylcarbonylalkenyl group means an alkenyl group substituted with an arylcarbonyl group wherein the arylcarbonyl group is a carbonyl group substituted with an aryl group.

As used herein, the term "heteroalkyl" means an alkyl bearing one or more heteroatoms unless otherwise indicated. As used herein, the terms "heteroaryl group" and "heteroarylene group" refer respectively to an aryl group and an arylene group of 2 to 60 carbon atoms bearing one or more heteroatoms therein, unless otherwise specified, without being limited thereto. It may include at least one of a single ring and multiple rings, and may be formed by combining adjacent functional groups.

Unless otherwise indicated, the term "heterocyclic group" as used herein, refers to at least one of heteroaliphatic rings and heteroaromatic rings of 2 to 60 carbon atoms bearing one or more heteroatoms as a ring member thereof, which may be mono- or multi-cyclic and may be formed as neighboring functional groups combine with each other.

The term "heteroatom" as used herein refers to N, O, S, P, or Si unless otherwise stated.

"Heterocyclic groups" may also include rings comprising $SO_2$, in place of carbon atoms, as a ring member. For example, a "heterocyclic group" includes the following compounds.

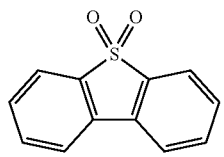 [SMILES: O=S1(=O)c2ccccc2-c2ccccc21]

Unless otherwise stated, the term "aliphatic" as used herein means an aliphatic hydrocarbon of 1 to 60 carbon atoms, and the "aliphatic ring" means an aliphatic hydrocarbon ring of 3 to 60 carbon atoms.

Unless otherwise stated, the term "ring" as used herein refers to an aliphatic ring of 3 to 60 carbon atoms, an aromatic ring of 6 to 60 carbon atoms, a hetero ring of 2 to 60 carbon atoms, or a fused ring consisting of a combination thereof whether or not it is saturated or unsaturated.

Other hetero-compounds or hetero-radicals other than the aforementioned hetero-compounds include, but are not limited to, one or more heteroatoms.

Unless otherwise stated, the term "carbonyl" as used herein is represented by —COR', wherein R' is hydrogen, an alkyl group of 1 to 20 carbon atoms, an aryl group of 6 to 30 carbon atoms, a cycloalkyl group of 3 to 30 carbon atoms, an alkenyl group of 2 to 20 carbon atoms, an alkynyl group of 2 to 20 carbon atoms, or a combination thereof.

Unless otherwise specified, the term "ether" as used herein is represented by —R—O—R', wherein R and R' are each independently hydrogen, an alkyl group of 1 to 20 carbon atoms, an aryl group of 6 to 30 carbon atoms, a cycloalkyl group of 3 to 30 carbon atoms, an alkenyl group of 2 to 20 carbon atoms, an alkynyl group of 2 to 20 carbon atoms, or a combination thereof.

Also, unless explicitly stated otherwise, the term "substituted" in the expression "substituted or unsubstituted" means having at least one substituent selected from the group consisting of, but not limited to, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl, a $C_3$-$C_{20}$ cycloalkyl group, a $C_6$-$C_{20}$ aryl group, a deuterium-substituted $C_6$-$C_{20}$ aryl group, a $C_8$-$C_{20}$ aryl alkenyl group, a silane group, a boron group, a germanium group, and a $C_2$-$C_{20}$ hetero-ring.

Also, unless otherwise stated, the chemical formulas used in the present invention are as defined for the exponent parts of the substituent in the following chemical formula:

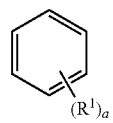

wherein,
when a is an integer of 0, the substituent $R^1$ being null,
when a is an integer of 1, one substituent $R^1$ is bonded to any one of the constituent carbon atoms of the benzene ring,
when a is an integer of 2 or 3, the substituents $R^1$'s, which may be the same or different, are each bonded as represented below, and
when a is an integer of 4 to 6, the substituents $R^1$'s are bonded to the constituents carbon atoms of the benzene ring in the same manner
while the hydrogens bonded to the constituent carbon atoms of the benzene ring are not indicated:

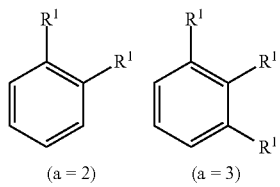

The FIGURE is an exemplary view of an organic electric device according to an embodiment of the present disclosure.

Referring to The FIGURE, an organic electric device 100 according to the present disclosure includes a substrate 110 in which a first electrode 120 and a second electrode 180 are formed, with an organic layer containing a compound according to the present disclosure interposed therebetween. In this regard, the first electrode 120 may be an anode and the second electrode 180 may be a cathode. In the case of an inverted type, the first electrode may be a cathode and the second electrode may be an anode.

The organic layer may include a hole injection layer 130, a hole transport layer 140, a light-emitting layer 150, an electron transport layer 160, and an electron injection layer 170 on the first electrode 120 in sequence. In this regard, the layers except for the light-emitting layer 150 may not be formed. A hole blocking layer, an electron blocking layer, an auxiliary light-emitting layer 151, or a buffer layer 141 may be further included, and the electron transport layer 160 may serve as a hole blocking layer.

In addition, although not shown, the organic electric element according to the present disclosure may further include a protective layer or a photo-efficiency improving layer (capping layer) formed on at least one of the surfaces of the first and the second electrode, which are located opposite to the organic layer.

The compound according to the present disclosure applied to the organic layer may be used as a host or dopant in the hole injection layer 130, the hole transport layer 140, the electron transport layer 160, the electron injection layer 170, or the light-emitting layer 150, or as a material for the photo-efficiency improving layer. Preferably, the compound of the present disclosure may be used for the light-emitting layer 150.

Meanwhile, compounds, although having the same core framework, may vary in band-gap, electrical property, and interfacial property, depending on positions at which substituents are bonded to the core framework. Thus, the selection of cores and the combination of sub-substituents bound thereto are also very significant. Importantly, long lifespan and high efficiency can be achieved simultaneously if energy levels, T1 values, and intrinsic properties (mobility, interfacial properties, etc.) in individual organic layers are optimally combined.

Hence, the present disclosure utilizes the compound represented by Chemical Formula 1 in forming a light-emitting layer, whereby energy levels, T1 values, intrinsic properties (mobility, interfacial properties, etc.) in individual organic layers can be optimized, with the consequent improvement of both lifespan and efficiency in the organic electric element.

An organic electric element according to an embodiment of the present invention may be manufactured using a physical vapor deposition (PVD) method. For example, a metal or a conductive metal oxide or an alloy thereof is deposited on a substrate to form an anode 120 on which organic layers including a hole injection layer 130, a hole transport layer 140, a light-emitting layer 150, an electron transport layer 160, and an electron injection layer 170 are then formed, followed by depositing a material available as a cathode 180 on the organic layers. Optionally, formation may be made of an auxiliary light-emitting layer 151 between the hole transport layer 140 and the light-emitting layer 150 and an auxiliary electron transport layer between the light-emitting layer 150 and the electron transport layer 160.

In addition, a fewer number of the organic layers may be formed by a solution or solvent process other than a deposition method, e.g., a spin coating process, a nozzle printing process, an inkjet printing process, a slot coating process, a dip coating process, a roll-to-roll process, a doctor blading process, a screen printing process, or a heat transfer method, using various polymer materials. Since the organic layers according to the present disclosure may be formed in various ways, the scope of the present disclosure is not limited by the forming method.

The organic electric element according to the present invention may be a top emission type, a bottom emission type or a double-sided emission type, depending on the material used.

In addition to being easily made to have high resolution and excellent processability, a white organic light-emitting diode (WOLED) can be fabricated using the color filter technology of the existing LCD. Various structures for WOLEDs, which are mainly used as backlight units, have been proposed and patented. Representative of them are a side-by-side method in which R (Red), G (Green), and B (Blue) light emitting parts are mutually position in a plane, a stacking method in which R, G, and B light-emitting layers are stacked up and down, and a color conversion material (CCM) method using the electroluminescence of a blue (B) organic light emitting layer and the photo-luminescence of an inorganic phosphor based on the light therefrom. The present disclosure may also be applied to these WOLEDs.

In addition, the organic electric element according to the present invention may be one of an organic electroluminescent diode (OLED), an organic solar cell, an organic photoconductor (OPC), an organic transistor (organic TFT), or a monochromatic or white illumination device.

Another embodiment of the present disclosure may provide a display device including the about-mentioned organic electric element of the present disclosure, and an electronic device including a control unit for controlling the display device. In this regard, the electronic device may be a current or future wired or wireless communication terminal and includes all electronic devices including, for example, a mobile communication terminal such as a mobile phone, a PDA, an electronic dictionary, a PMP, a remote controller, a navigation device, a game machine, various TVs, and various computers.

Hereinafter, the compound according to one aspect of the present disclosure is explained. The compound according to an aspect of the present disclosure is represented by the following formula (1):

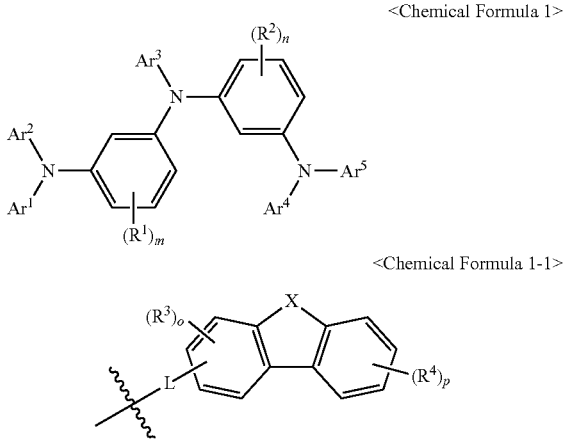

<Chemical Formula 1>

<Chemical Formula 1-1> wherein,

1) $Ar^1$ to $Ar^5$, which may be the same or different, are each independently one selected from the group consisting of a $C_6$-$C_{60}$ aryl group; a substituent represented by Chemical Formula 1-1; a fluorenyl group; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; and a $C_6$-$C_{30}$ aryloxy group, with a proviso that at least one of $Ar^1$ to $Ar^5$ is a substituent represented by Chemical Formula 1-1, 2) $R^1$ to $R^4$ are each independently on selected from the group consisting of hydrogen; deuterium; a $C_6$-$C_{60}$ aryl group; a fluorenyl group; a $C_2$-$C_{60}$ hetero ring group bearing at least one hetero atom of O, N, S, Si, and P as a ring member; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; and a $C_6$-$C_{30}$ aryloxy group, wherein multiple $R^3$'s or multiple $R^4$'s may combine with each other to form an aromatic or a heteroaromatic ring, 3) m, n, and p are each independently an integer of 0 to 4, with a proviso that when m, n, and p are each 2 or greater, the multiple $R^1$'s, $R^2$'s, and $R^4$'s may each be the same or different, 4) o is an integer of 0 to 3, with a proviso that when o is 2 or greater, the $R^3$'s are the same or different, 5) X is selected to be $C(R_a)(R_b)$, wherein $R_a$ and $R_b$ are each independently one selected from the group consisting of a $C_6$-$C_{60}$ aryl group; a fluorenyl group; a $C_2$-$C_{60}$ hetero ring group bearing at least one hetero atom of O, N, S, Si, and P as a ring member; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; a $C_6$-$C_{30}$ aryloxy group; and a $C_6$-$C_{60}$ arylene group, and may optionally combine with each other to form a spiro compound with the carbon atom bonded thereto.

6) L is one selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ hetero ring group bearing at least one hetero atom of O, N, S, Si, and P as a ring member, with preference for a single bond;

wherein, the aryl group, the fluorenyl group, the arylene group, the hetero ring group, the fused ring group, the alkyl group, the alkenyl group, the alkoxy group, and the aryloxy group may each be further substituted with at least one substituent selected from the group consisting of deuterium; halogen; a $C_1$-$C_{20}$ alkyl group or $C_6$-$C_{20}$ aryl group-substituted or unsubstituted silane group; a siloxane group; a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a deuterium-substituted $C_6$-$C_{20}$ aryl group; a fluorenyl group; a $C_2$-$C_{20}$ hetero ring group; a $C_3$-$C_{20}$ cycloalkyl group; a $C_7$-$C_{20}$ arylalkyl group; and a $C_8$-$C_{20}$ arylalkenyl group, wherein the substituents may combine with each other to form a ring wherein the term "ring" refers to a $C_3$-$C_{60}$ aliphatic ring, a $C_6$-$C_{60}$ aromatic ring, a $C_2$-$C_{60}$ hetero ring, or a fused ring consisting of a combination thereof whether it is saturated or unsaturated.

As for the aryl group, its number of carbon atoms may be 6-60, preferably 6-40, and more preferably 6-30. The number of carbon atom in the hetero ring may be 2-60, preferably 2-30, and more preferably 2-20. The alkyl group may have 1-50 carbon atoms, preferably 1-30 carbon atoms, more preferably 1-20 carbon atoms, and particularly preferably 1-10 carbon atoms.

Concrete examples of the aryl group include a phenyl group, a biphenyl group, a terphenyl group, a naphthyl group, and a phenanthryl group while the arylene group may be exemplified concretely by a phenylene group, a biphenylene group, a terphenylene group, a naphthalene group, a phenanthrylene group, a pyrene group, and a triphenylene group.

In greater detail, the compound represented by Chemical Formula 1 may be any one of the following compounds, but is not limited thereto.

Chemical Formula 1 may be concretely expressed as one of Chemical Formulas 2 to 7, below:

<Chemical Formula 2>

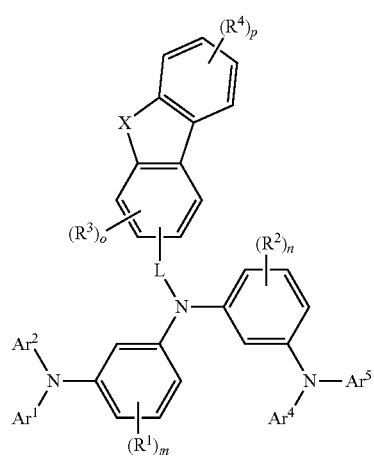

<Chemical Formula 3>

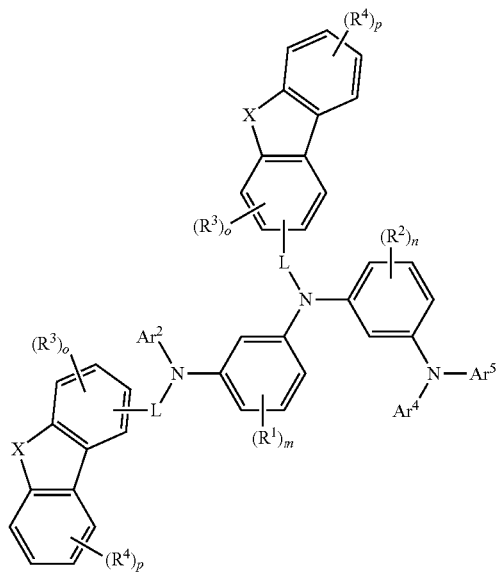

<Chemical Formula 4>

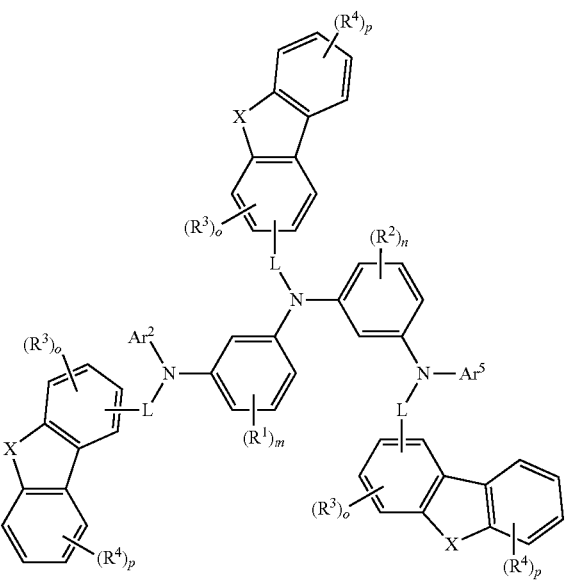

<Chemical Formula 5>

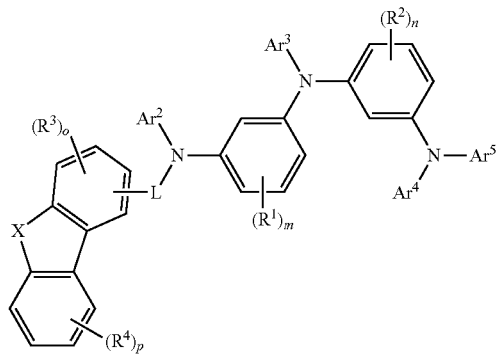

<Chemical Formula 6>
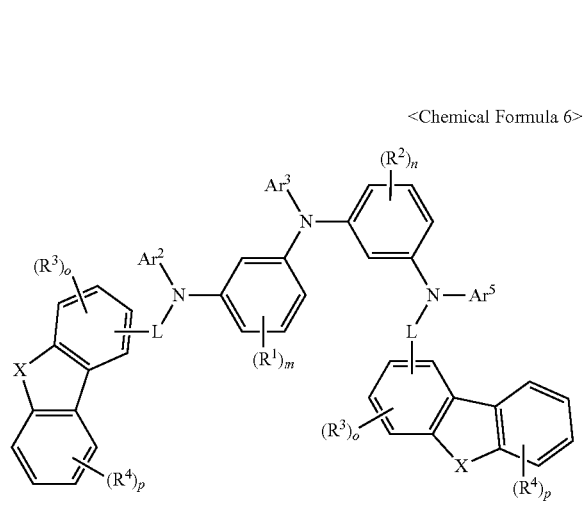
<Chemical Formula 7>
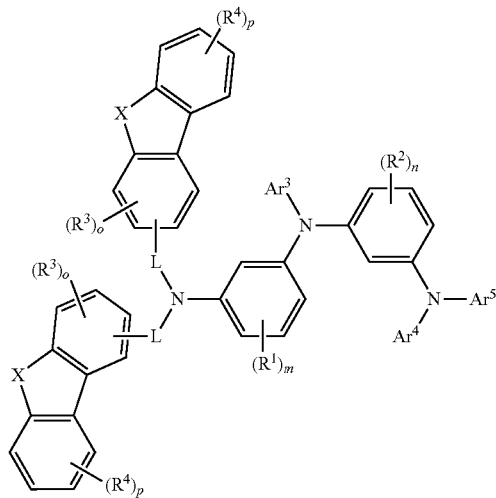
wherein, X, $Ar^1$ to $Ar^5$, L, $R^1$ to $R^4$, m, n, o, and p are as defined for X, $Ar^1$ to $Ar^5$, L, $R^1$ to $R^4$, m, n, o, and p in Chemical Formula 1.
Concrete examples of the compound represented by Chemical Formula 1 include, but are not limited to, the following compounds:
P-1
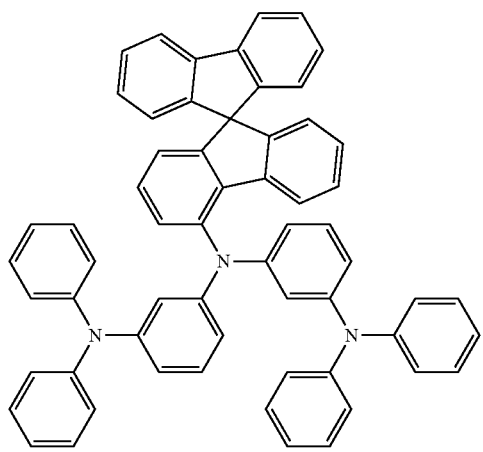
P-2
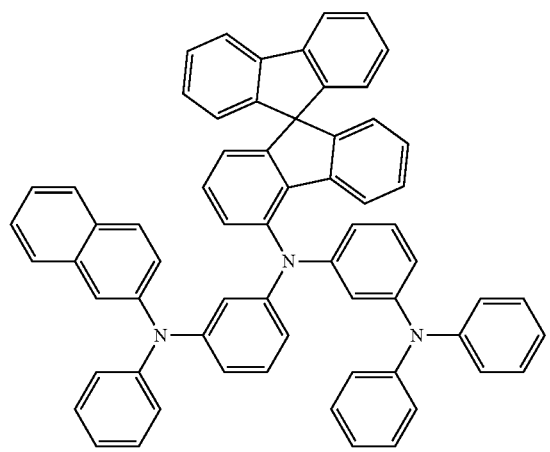
P-3
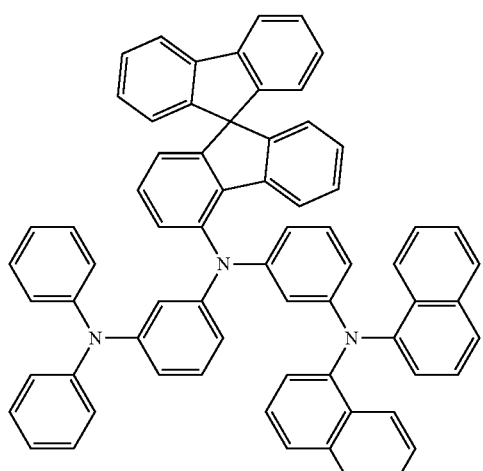
P-4
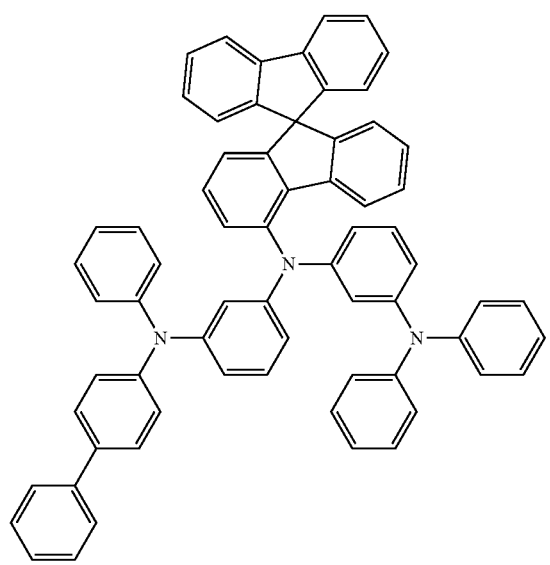

-continued
P-5
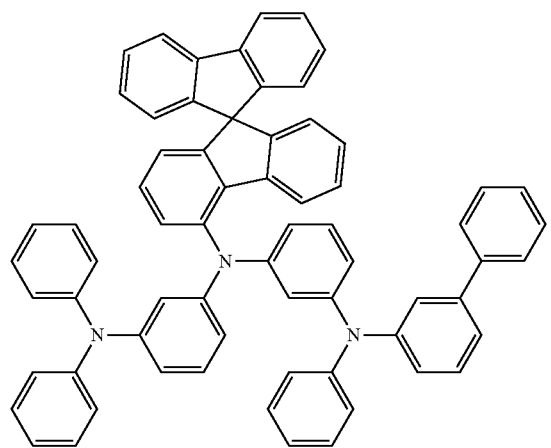
P-6
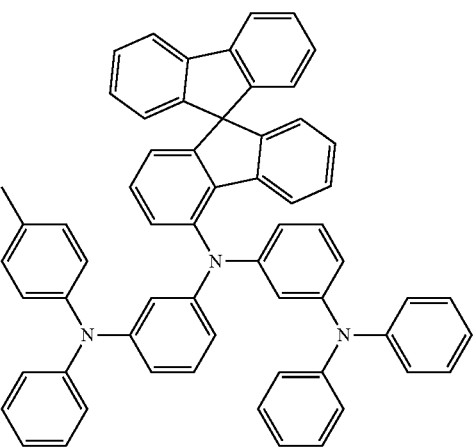
P-7
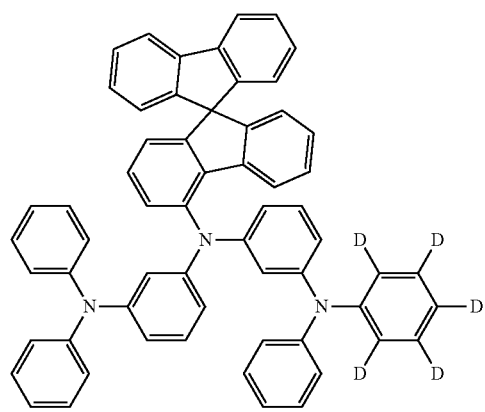
P-8
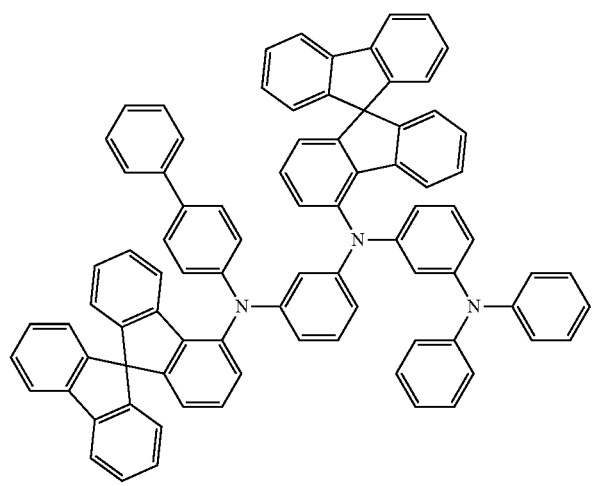
P-9
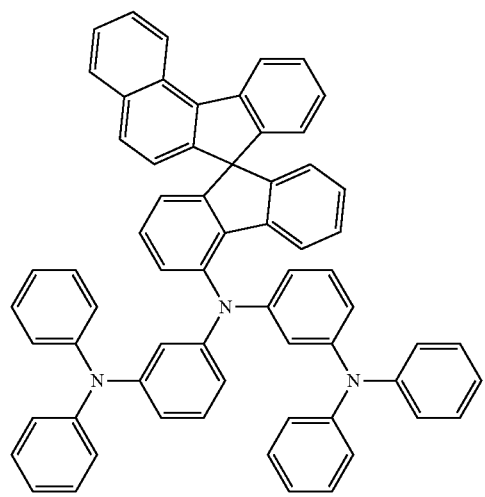
P-10
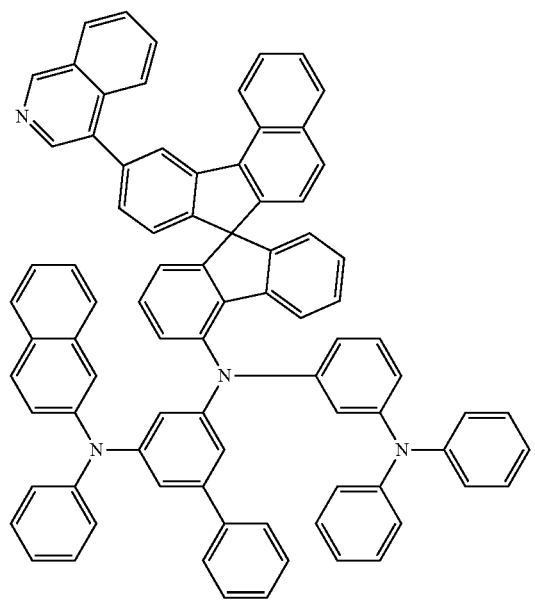

-continued
P-11
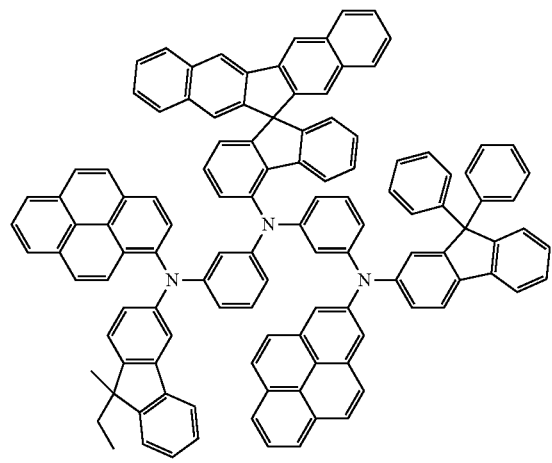
P-12
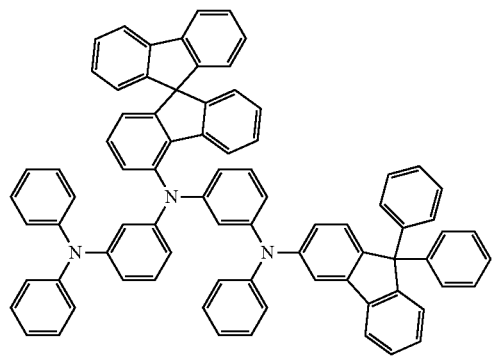
P-13
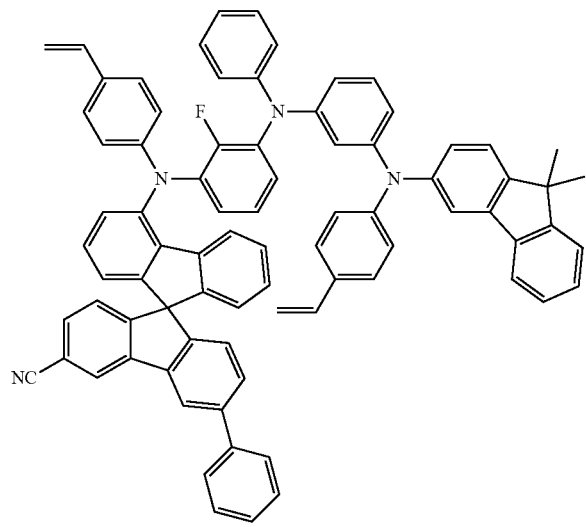
P-14
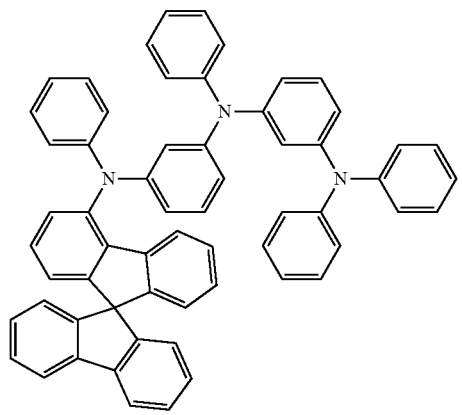
P-15
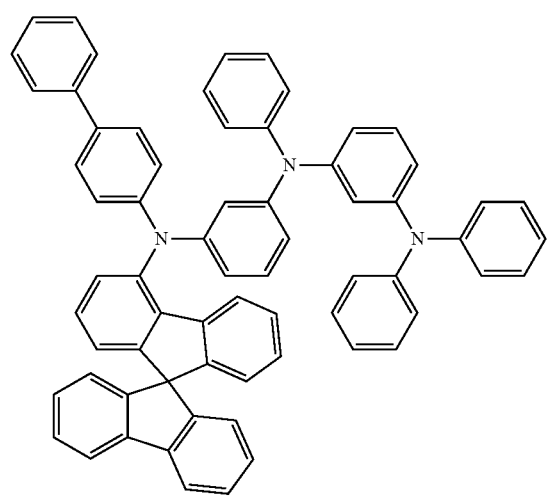
P-16
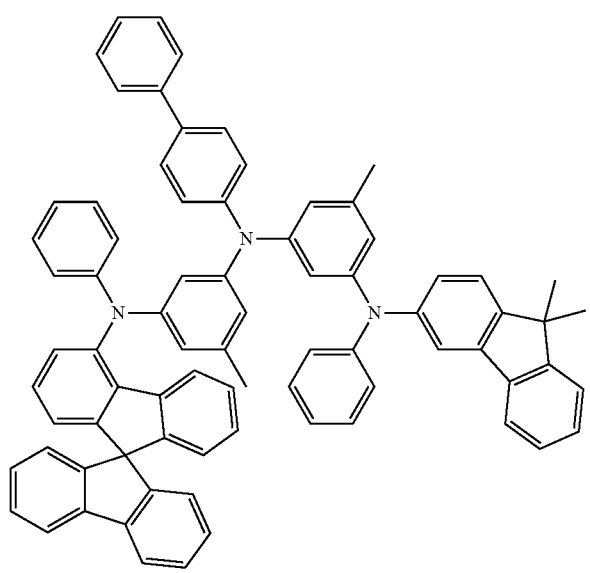

-continued
P-17
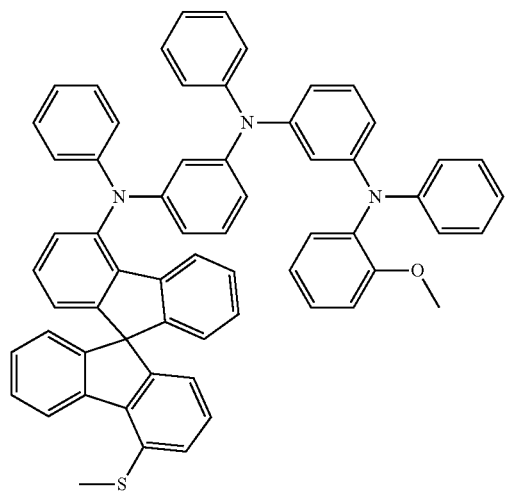
P-18
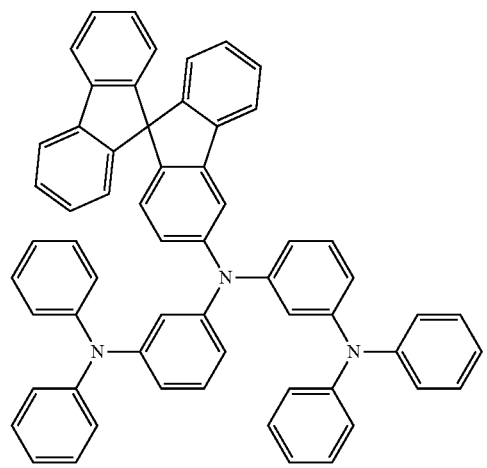
P-19
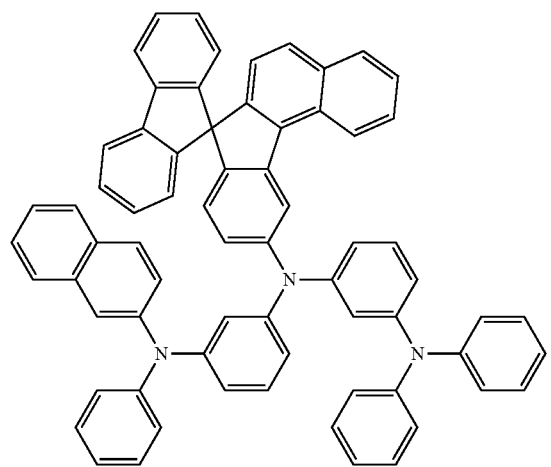
P-20
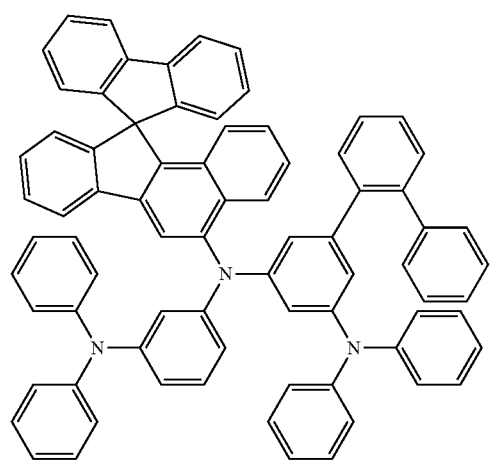
P-21
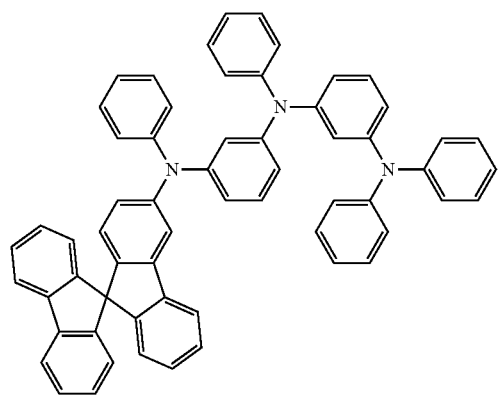
P-22
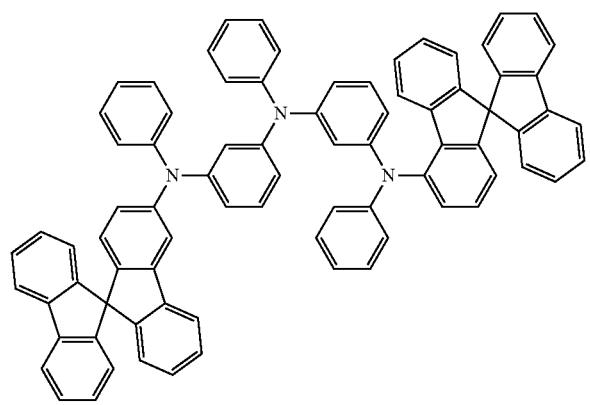

-continued
P-23
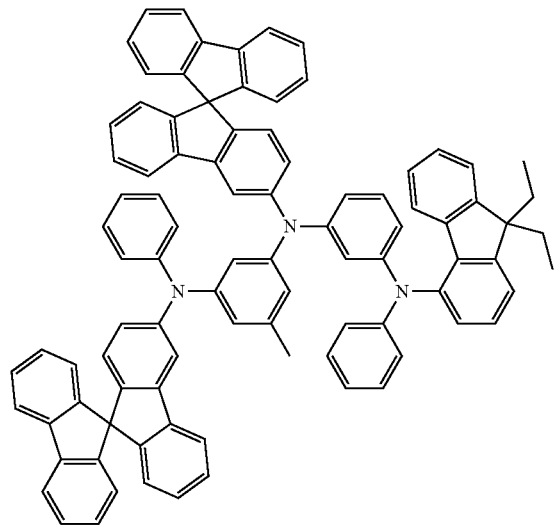
P-24
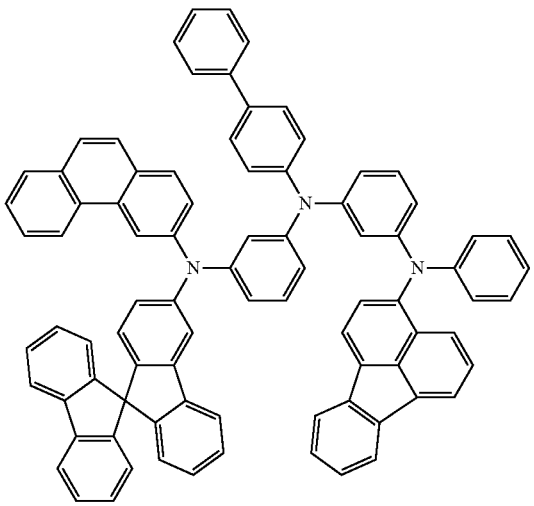
P-25
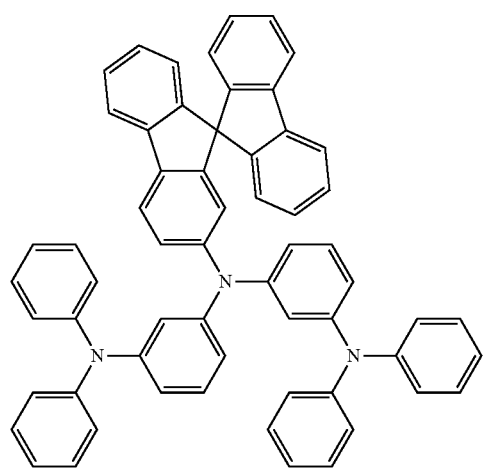
P-26
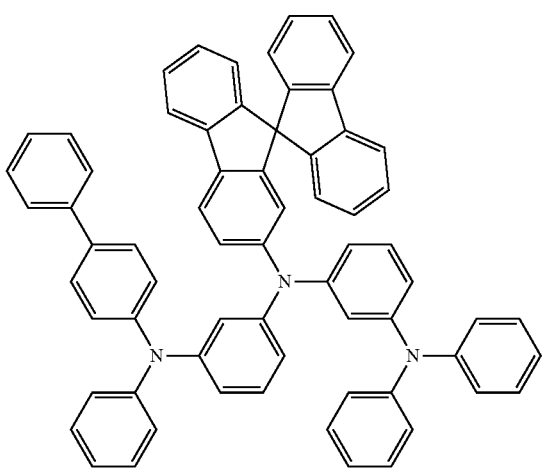
P-27
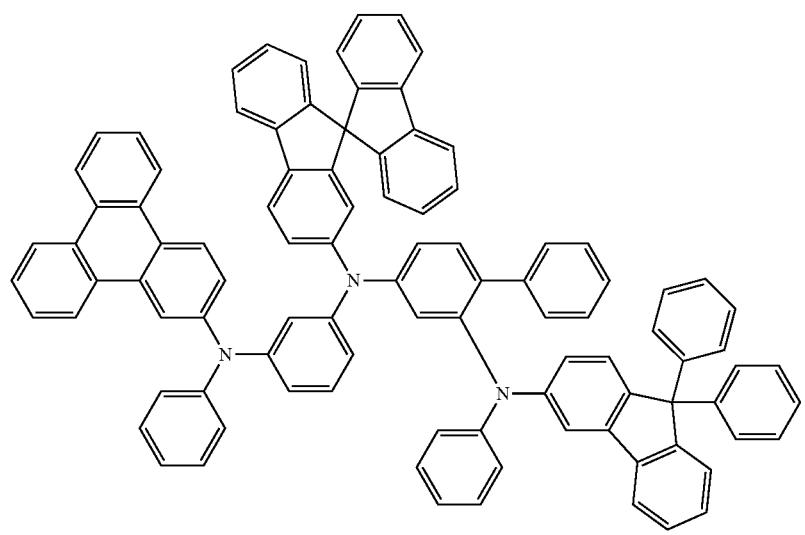

-continued
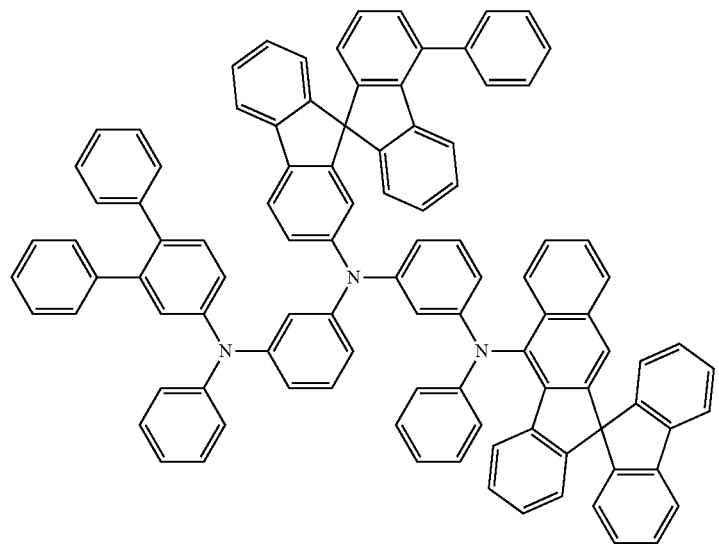
P-28
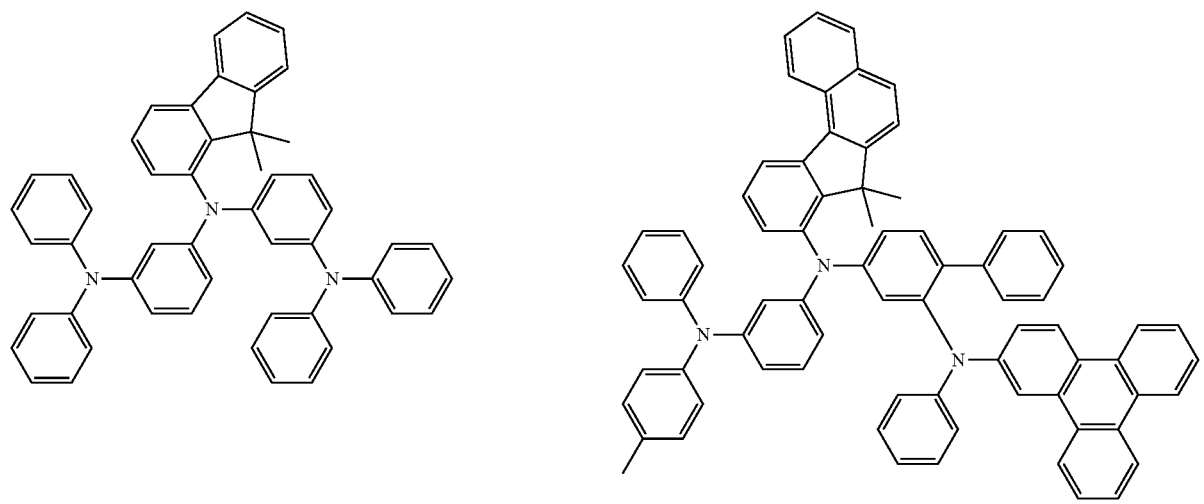
P-53     P-54
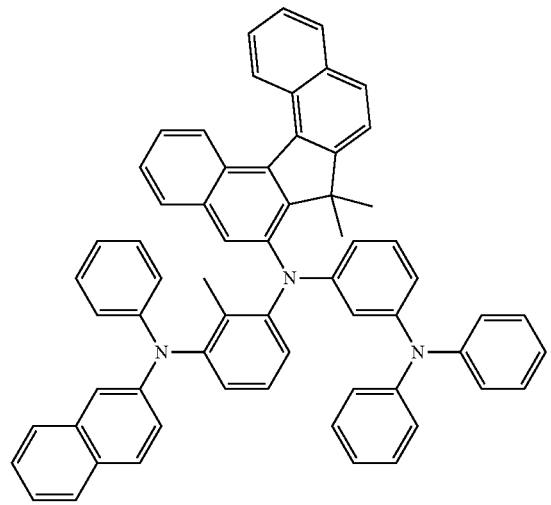
P-55     P-56

-continued
P-57
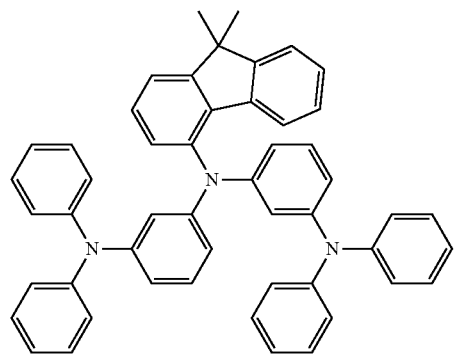
P-58
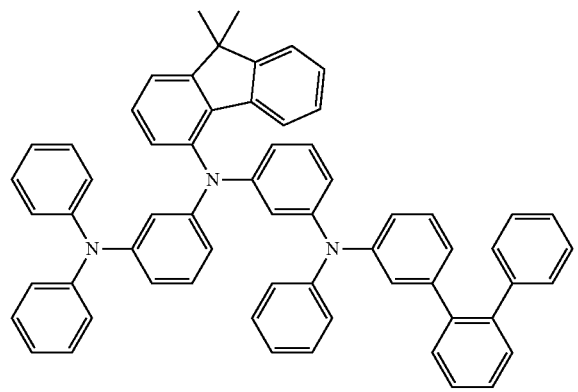
P-59
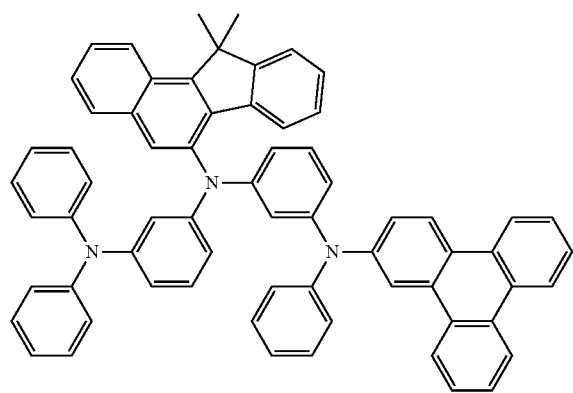
P-60
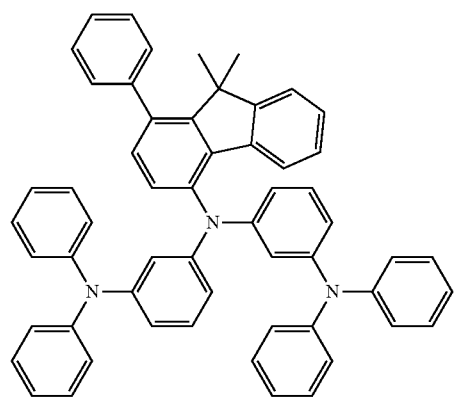
P-61
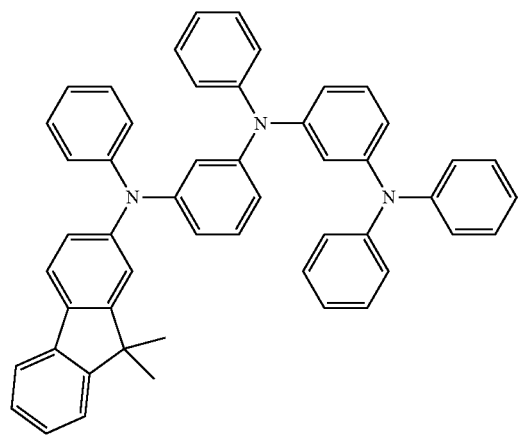
P-62
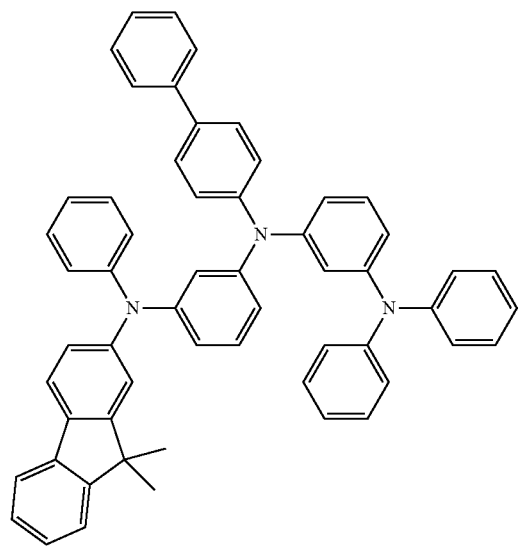

-continued
P-63
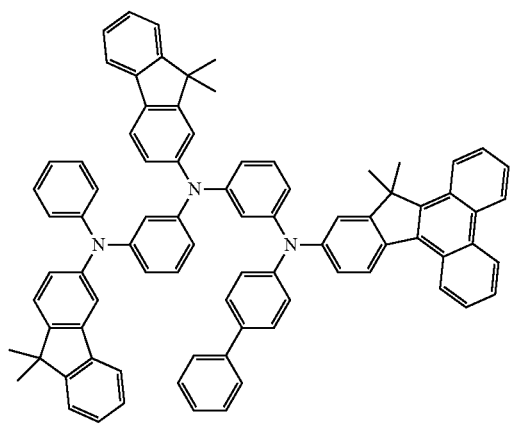
P-64
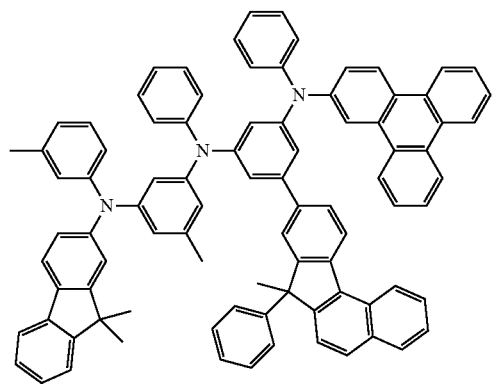
P-65
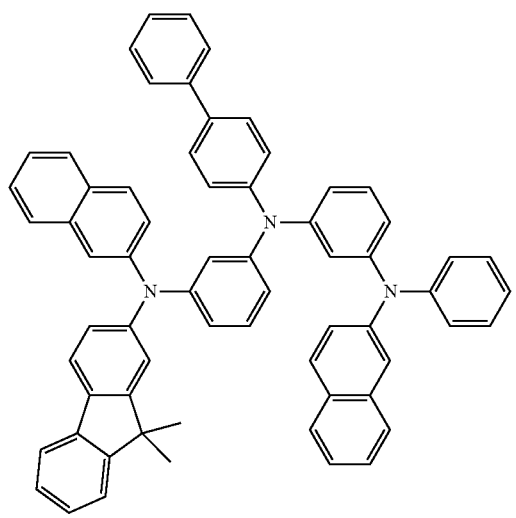
P-66
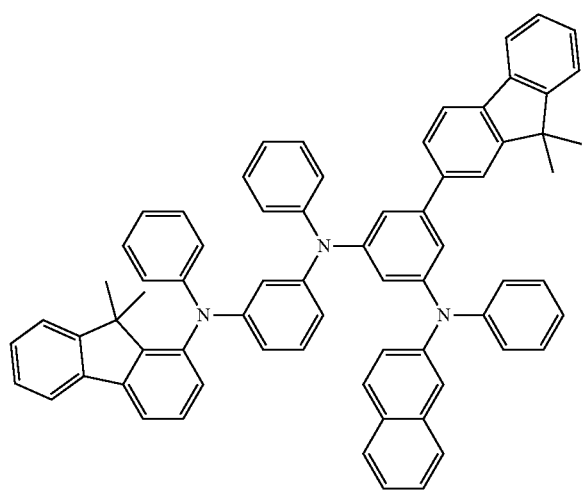
P-67
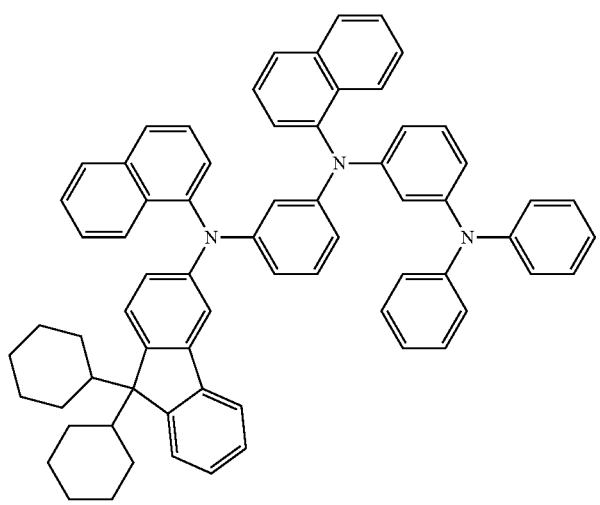
P-68
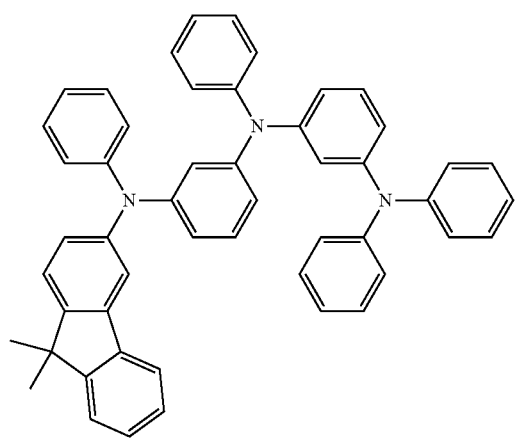

-continued
P-69
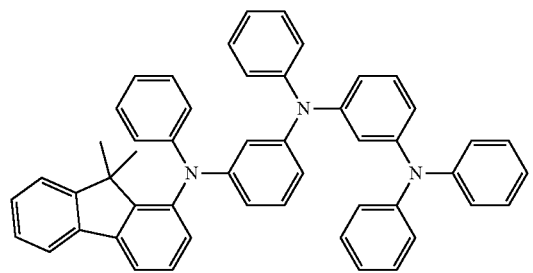
P-70
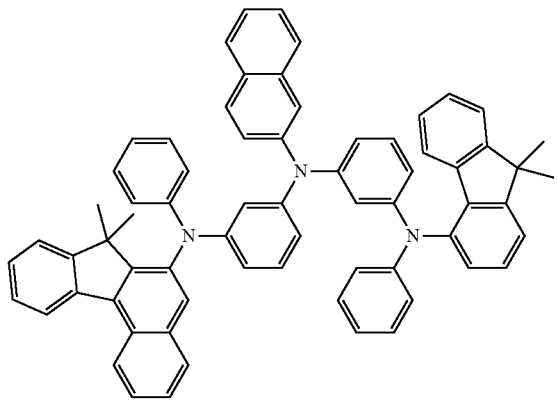
P-71
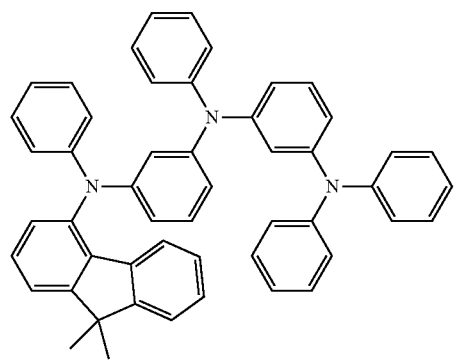
P-72
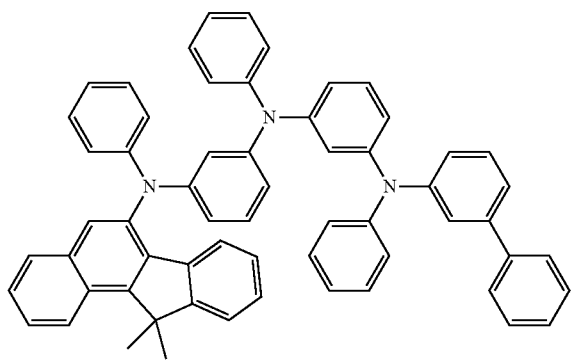
P-73
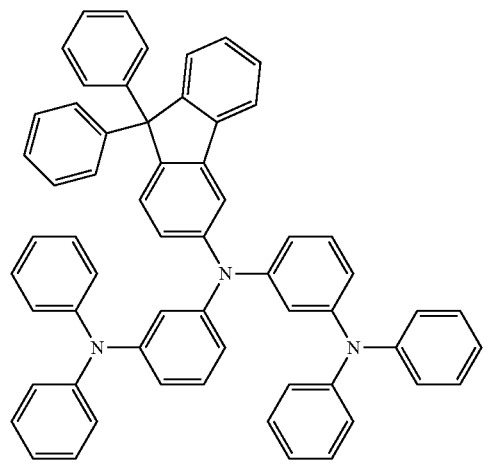
P-74
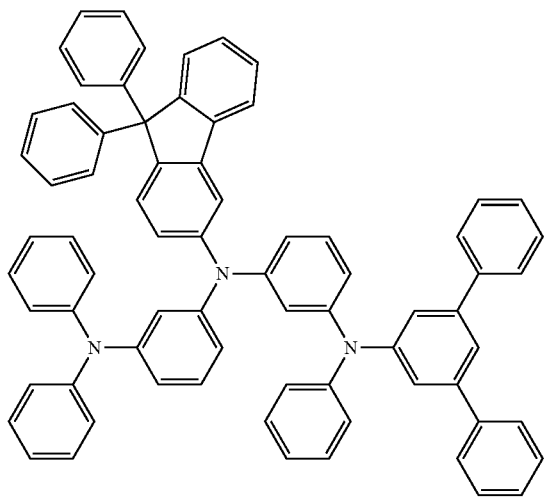

-continued
P-75
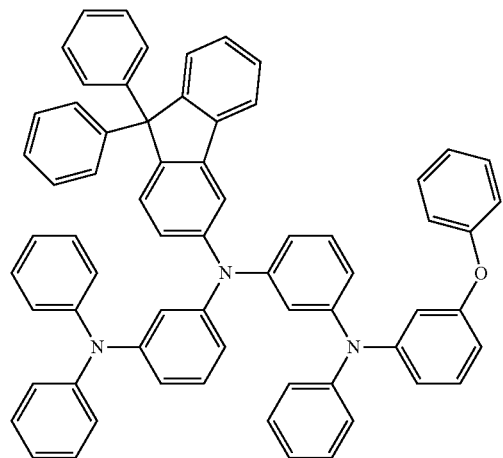
P-76
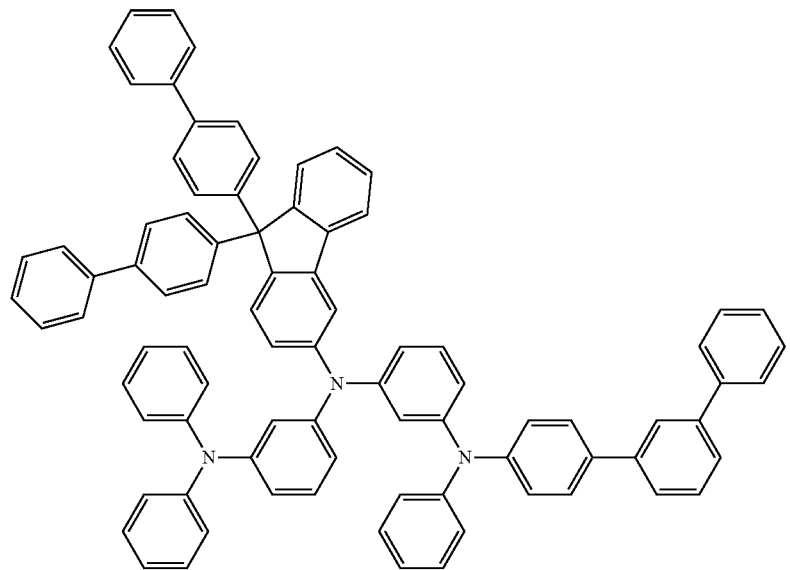
P-77
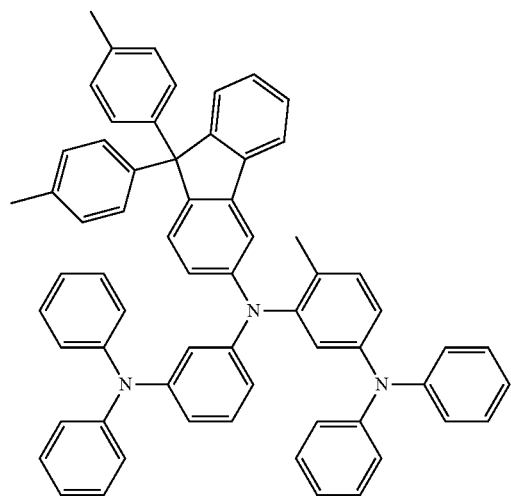
P-78
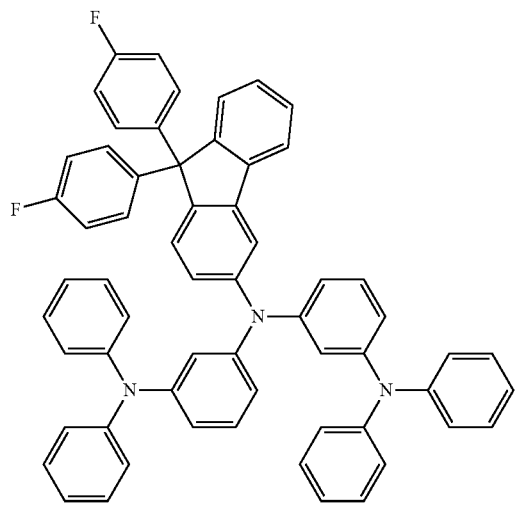

-continued
P-79
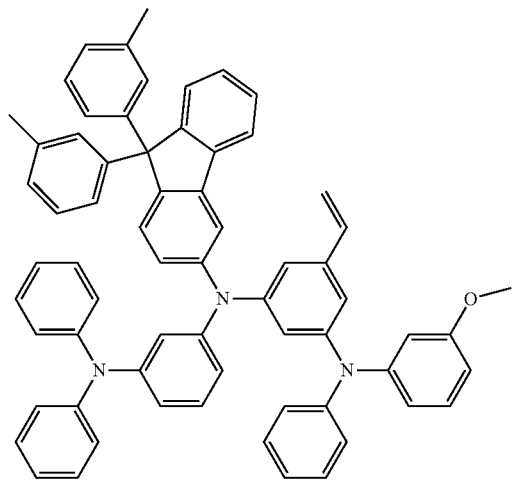
P-80
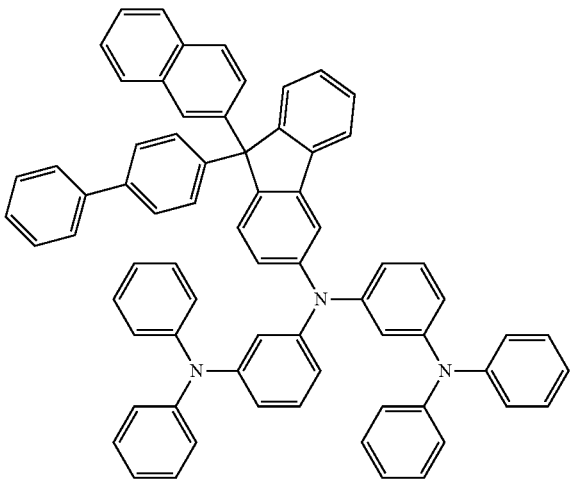
P-81
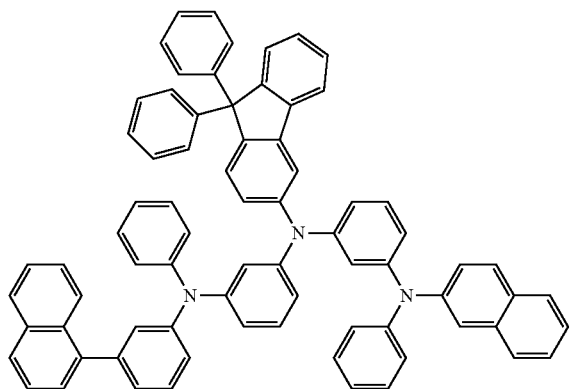
P-82
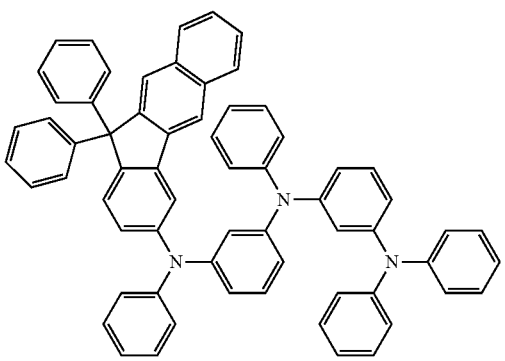
P-83
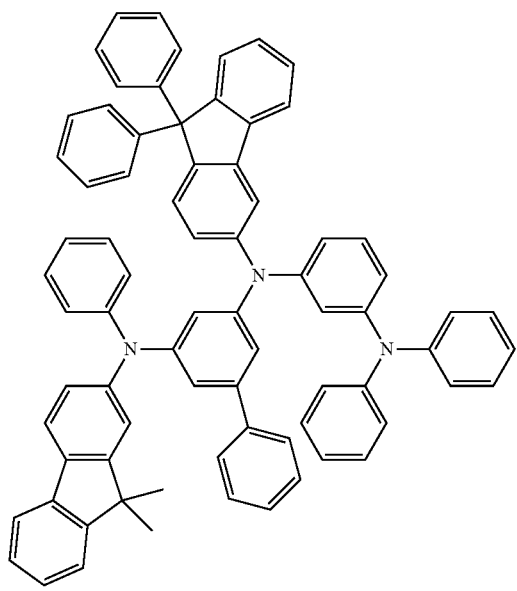
P-84
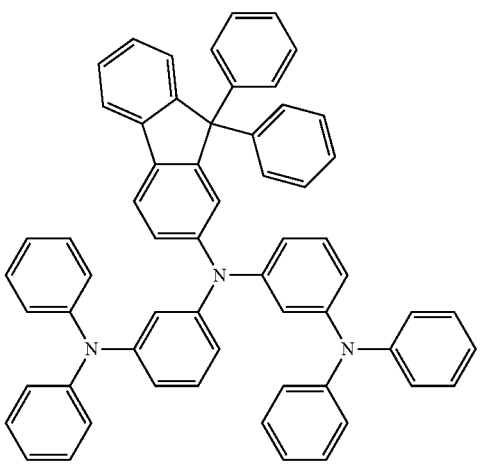

-continued
P-85
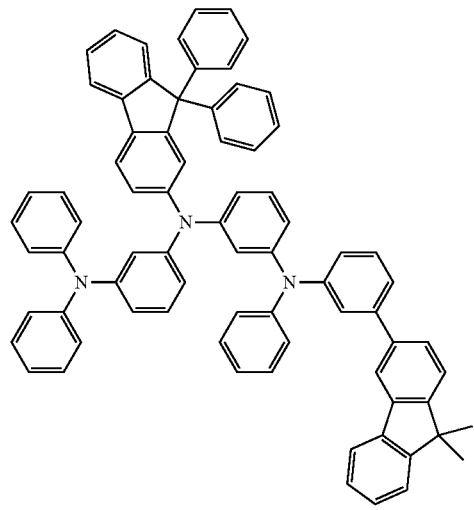
P-86
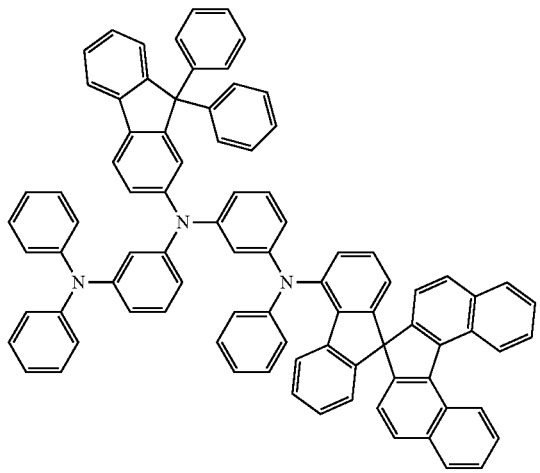
P-87
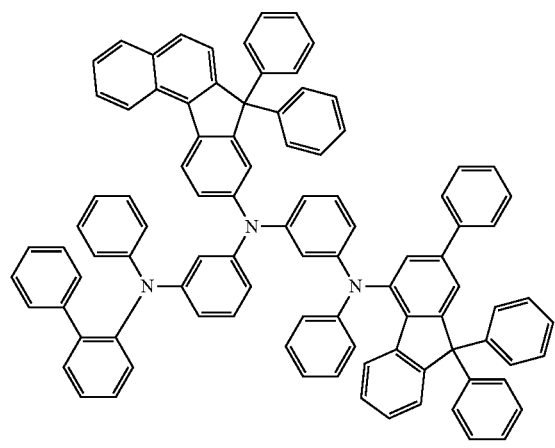
P-88
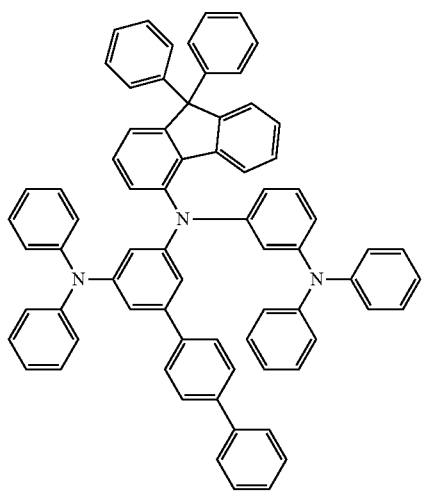
P-89
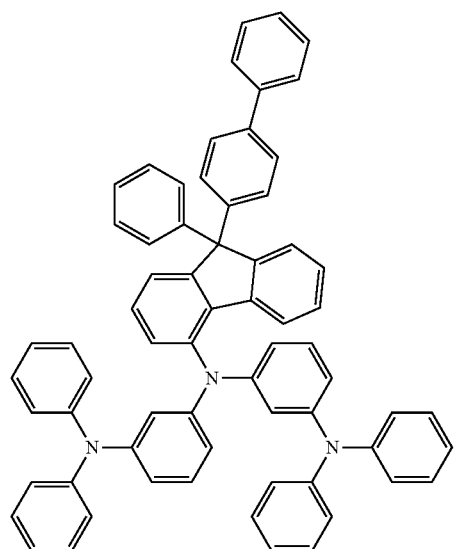
P-90
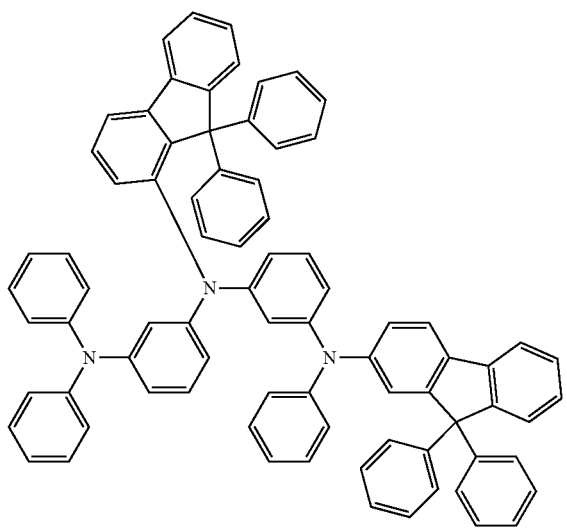

-continued
P-91
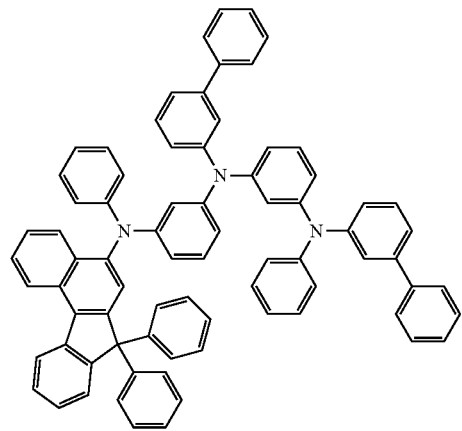
P-92
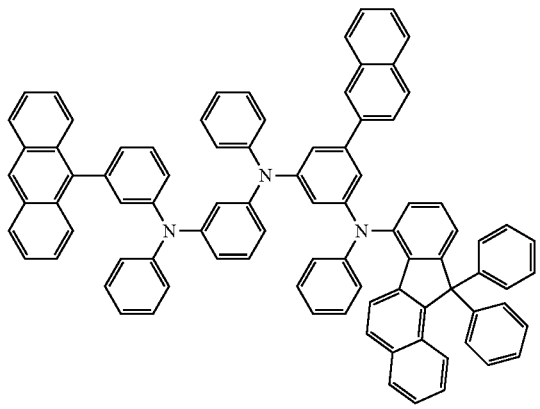
P-93
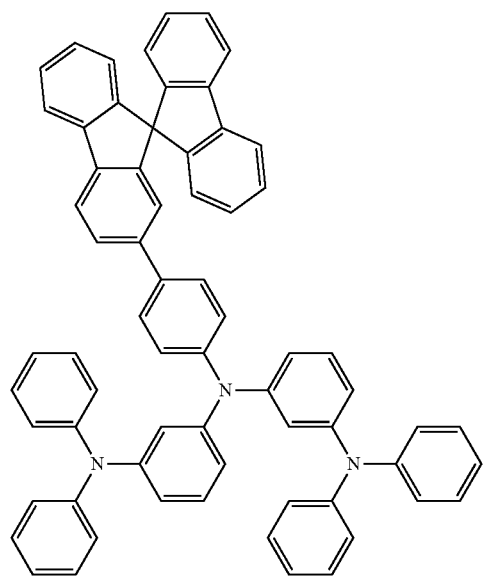
P-94
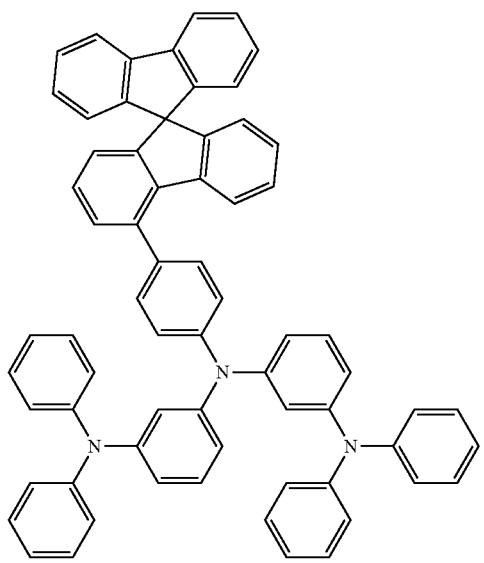
P-95
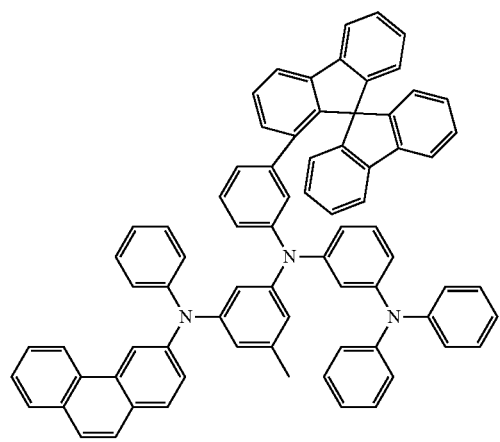
P-96
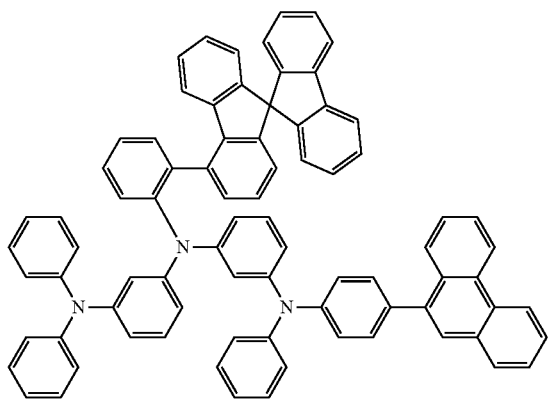

-continued
P-97
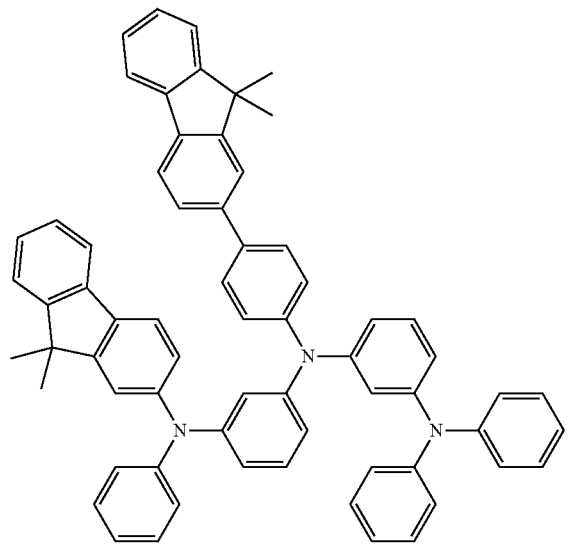
P-98
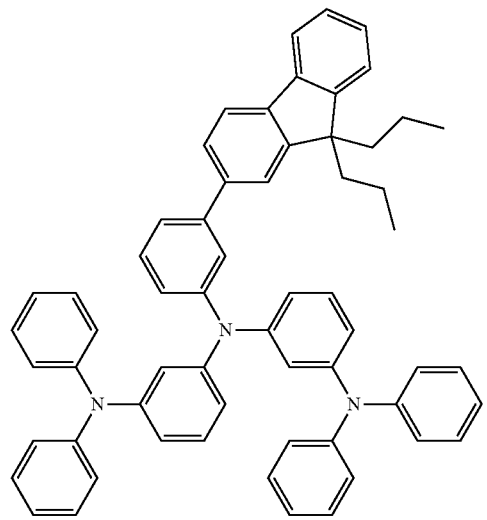
P-99
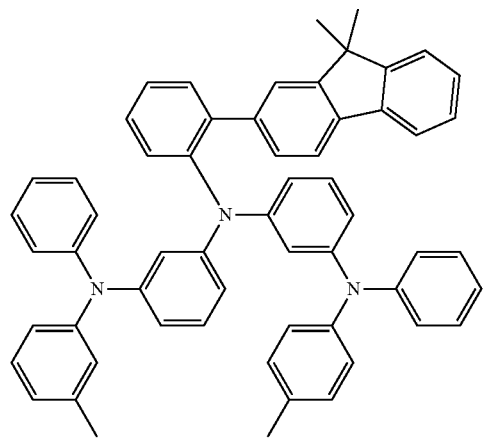
P-100
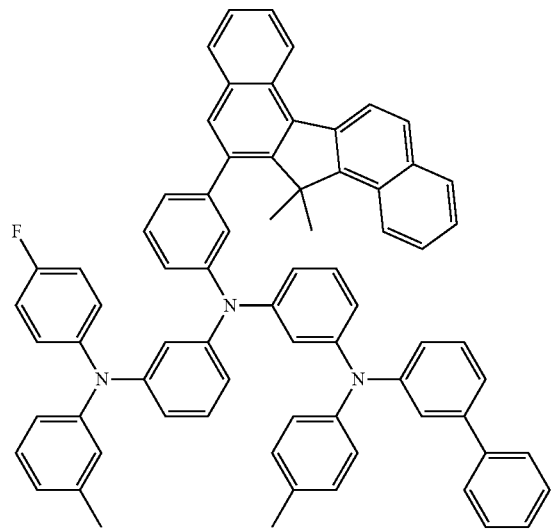
P-101
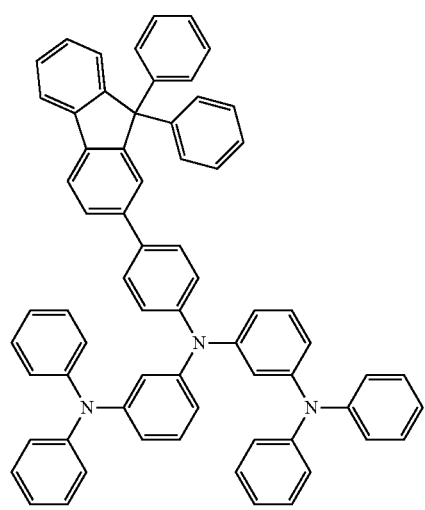
P-102
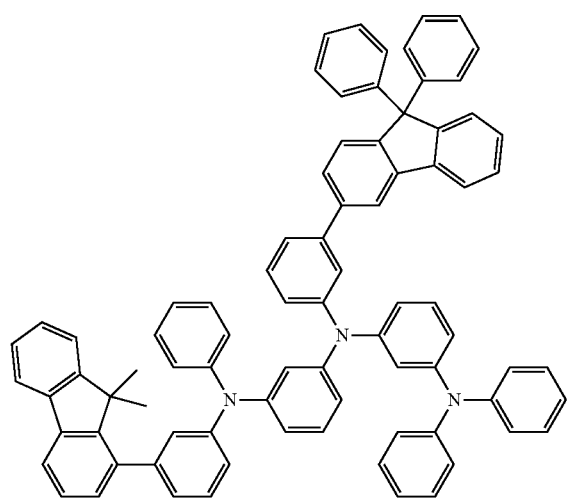

P-103

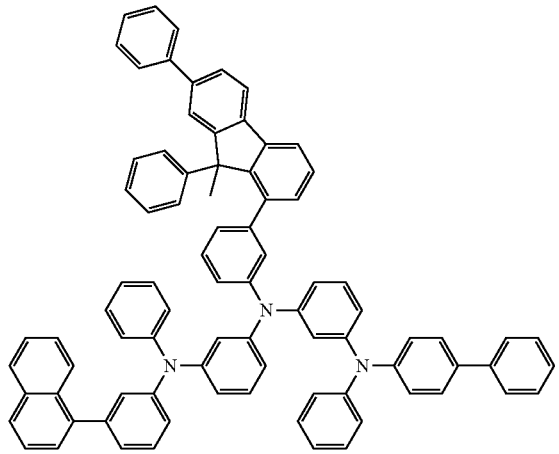

P-104

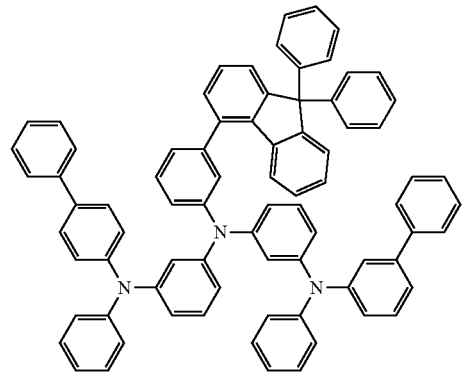

In another embodiment, the present disclosure provides a compound for an organic electric element represented by Chemical Formula 1.

In another embodiment, the present disclosure provides an organic electric element containing the compound represented by Chemical Formula 1.

In this context, the organic electric element includes a first electrode; a second electrode; and an organic layer disposed between the first electrode and the second electrode. The organic layer may contain a compound represented by Chemical Formula 1, and the compound represented by Chemical Formula 1 may be contained in at least one of a hole injection layer, a hole transport layer, an auxiliary light-emitting layer, a light-emitting layer, an auxiliary electron transport layer, an electron transport layer, and an electron injection. In particular, the compound represented by Formula 1 may be contained in a hole transport layer or an auxiliary light-emitting layer.

That is, the compound represented by Chemical Formula 1 may be used as a material for a hole injection layer, a hole transport layer, an auxiliary light-emitting layer, a light-emitting layer, an auxiliary electron transport, an electron transport layer, or an electron injection layer. In particular, the compound represented by Chemical Formula 1 may be used as a material for a hole transport layer or an auxiliary light-emitting layer. Provided are specifically an organic electric element comprising an organic layer containing one of the compounds represented by Chemical Formula 1 therein, and more specifically an organic electric element comprising an organic layer containing one of the compounds represented by the individual formulas (P-1 to P-104) therein.

Another embodiment provides an organic electric element wherein the compounds are contained singly or in combination thereof or in combination with at least one different compound in at least one of the hole injection layer, the hole transport layer, the auxiliary light-emitting layer, the light-emitting layer, the auxiliary electron transport layer, the electron transport layer, and the electron injection layer. In greater detail, each of the layers may contain a single compound of Chemical Formula 1, two or more compounds of Chemical Formula 1, or a mixture of the compound of claims 1 to 3 and a compound that does not corresponding to the present disclosure. Herein, the compound not corresponding to the present disclosure may be a single compound or two or more compounds. In the context that the compound of the present disclosure is contained in combination with a different compound, the different compound may be a well-known one or a compound to be developed in future. The compounds contained in the organic layer may be homogeneous or a mixture of two or more heterogeneous compounds represented by Chemical Formula 1.

Provided according to still another embodiment of the present disclosure is the organic electric element further comprising a photo-efficiency improving layer formed on at least one of the surfaces of the first and the second electrode, which are located opposite to the organic layer.

Hereinafter, the synthesis of the compounds represented by Chemical Formula 1 according to the present disclosure and the fabrication of the organic electric element will be described in detail by way of examples, which are set forth to illustrate, but not to limit the present disclosure.

SYNTHESIS EXAMPLES

The compound (final product) represented by Chemical Formula 1 according to the present disclosure is synthesized by reacting Sub 1 with Sub 2, as illustrated in, but not limited, the following Reaction Scheme 1. In Reaction Scheme 1, $Ar^1$ to $Ar^5$, L, $R^1$ to $R^4$, and m are as defined in Chemical Formula 1.

<Reaction Scheme 1>

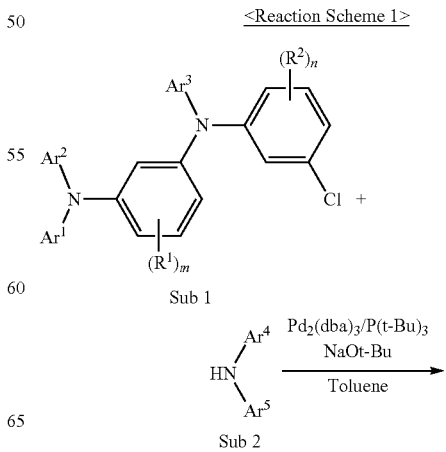

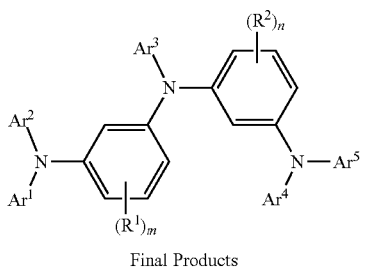

Final Products

I. Synthesis of Sub 1

Sub 1 of Reaction Scheme 1 can be synthesized via the reaction route of Reaction Scheme 2, with no limitations imparted thereto.

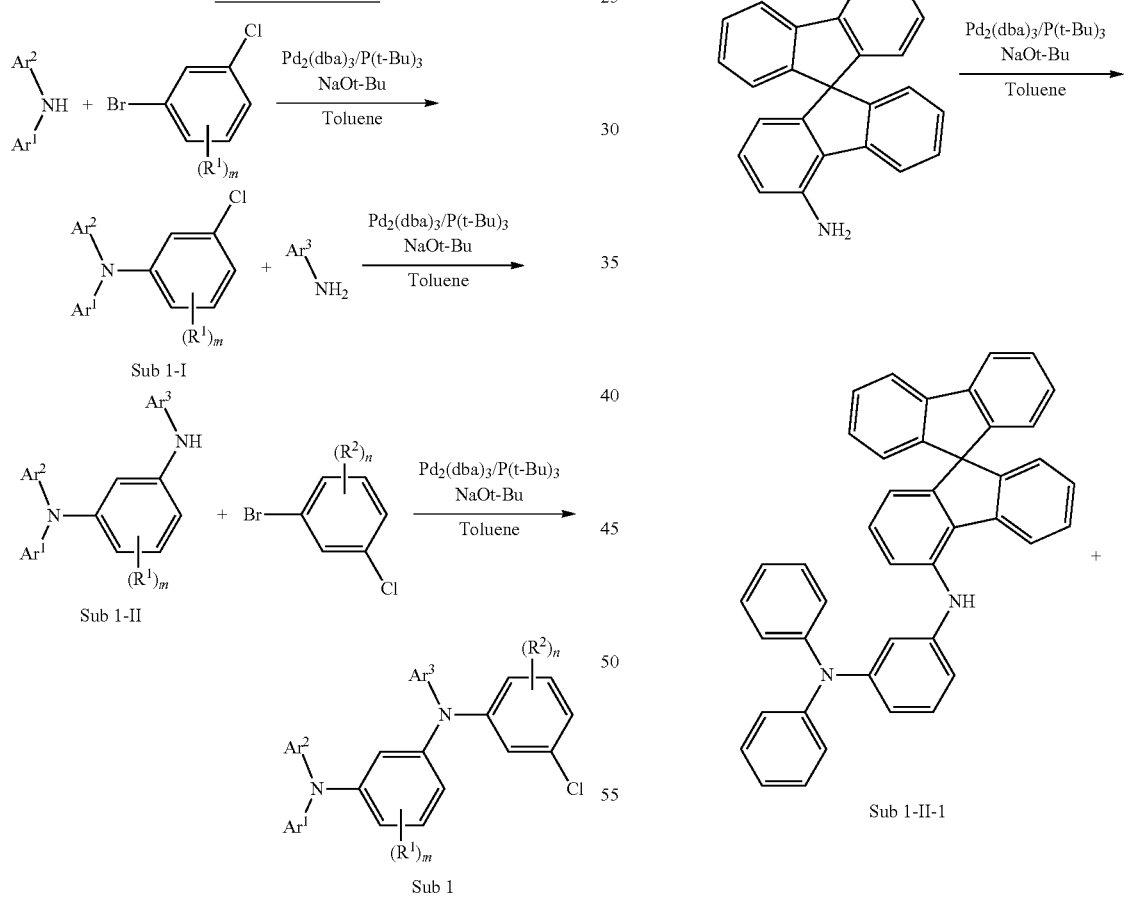

Sub 1

In Reaction Scheme 2, the amine reactant (HN—$Ar^1Ar^2$) was synthesized using the method disclosed in Korean Patent Number 10-1251451 (issued Apr. 5, 2013) to the present applicant.

Concrete compounds of Sub 1 can be synthesized as in the following Synthesis Examples:

1. Synthesis Example: Sub 1-1

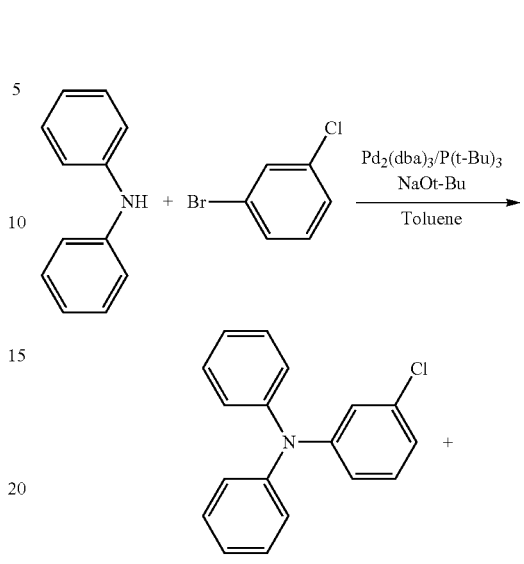

Sub 1-I-1

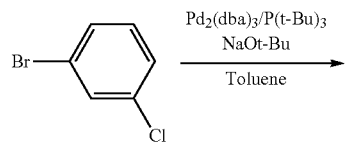

Sub 1-II-1

2. Synthesis Example: Sub 1-14

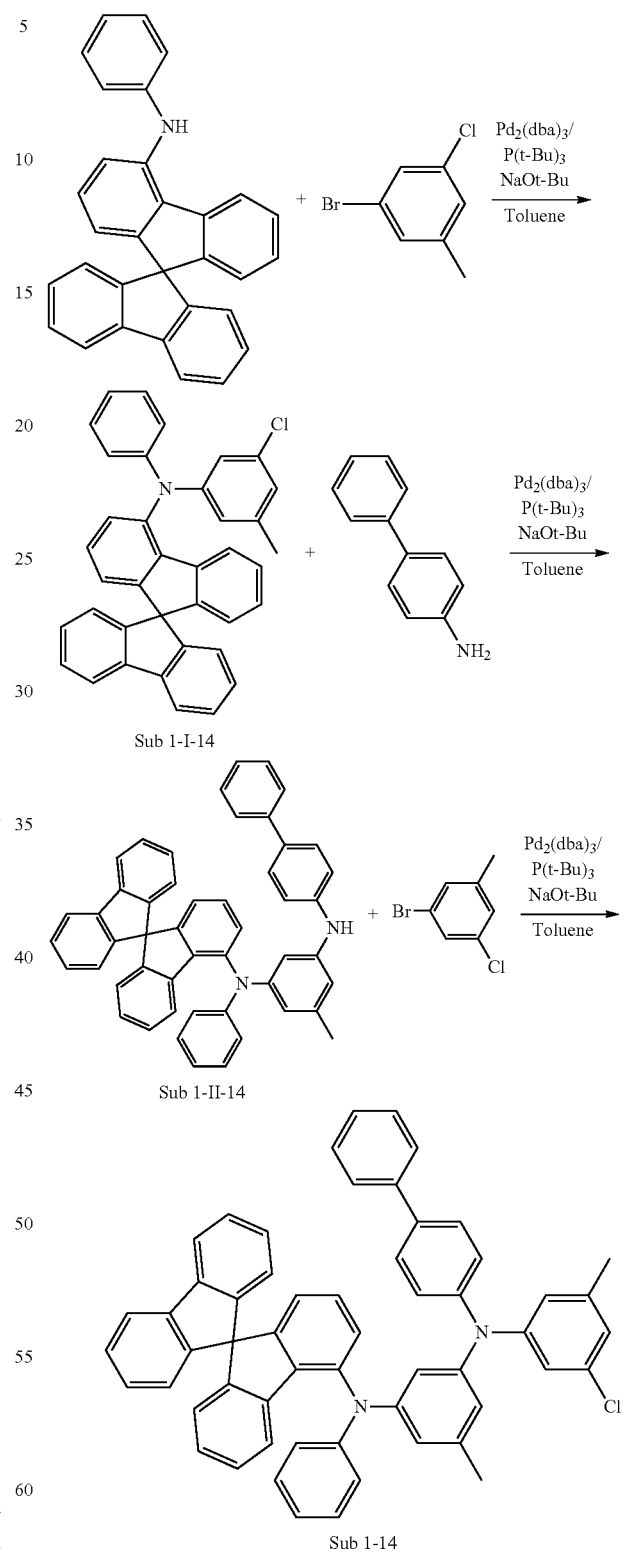

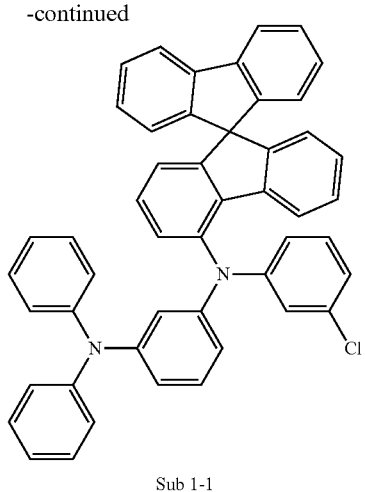

Sub 1-1

(1) Synthesis of Sub 1-I-1

In a round-bottom flask, a solution of diphenylamine (500 g, 2954.6 mmol) in toluene (9 L) was added with 1-bromo-3-chlorobenzene (680 g, 3550.0 mmol), $Pd_2(dba)_3$ (81.2 g, 88.6 mmol), 50% $P(t-Bu)_3$ (86.4 ml, 177.2 mmol), and NaOt-Bu (853 g, 8863.6 mmol) and then stirred at 80° C. After completion of the reaction, extraction was performed with $CH_2Cl_2$ and water. The organic layer thus formed was dried over $MgSO_4$ and concentrated. The concentrate was purified by silica gel column chromatography, followed by recrystallization to afford 752 g of the product Sub 1-I-1 (yield: 91%).

(2) Synthesis of Sub 1-II-1

Sub 1-I-1 (100 g, 357.4 mmol) obtained in the above synthesis was added, together with 9,9'-spirobi[fluoren]-4-amine (118.4 g, 357.4 mmol), $Pd_2(dba)_3$ (9.8 g, 10.7 mmol), 50% $P(t-Bu)_3$ (10.5 ml, 21.4 mmol), and NaOt-Bu (103.1 g, 1072.2 mmol) to toluene (1190 ml) and then stirred at 130° C. After completion of the reaction, extraction was performed with $CH_2Cl_2$ and water. The organic layer thus formed was dried over $MgSO_4$ and concentrated. The concentrate was purified by silica gel column chromatography, followed by recrystallization to afford 180 g of the product Sub 1-II-1 (yield: 87.7%).

(3) Synthesis of Sub 1-1

Sub 1-II-1 (180 g, 313.2 mmol) obtained in the above synthesis was added, together with 1-bromo-3-chlorobenzene (60 g, 313.2 mmol), $Pd_2(dba)_3$ (8.6 g, 9.4 mmol), 50% $P(t-Bu)_3$ (9.2 ml, 18.8 mmol), and NaOt-Bu (90.3 g, 939.6 mmol), to toluene (1050 ml) and then stirred at 130° C. After completion of the reaction, extraction was performed with $CH_2Cl_2$ and water. The organic layer thus formed was dried over $MgSO_4$ and concentrated. The concentrate was purified by silica gel column chromatography, followed by recrystallization to afford 201 g of the product Sub 1-1 (yield: 93.5%).

(1) Synthesis of Sub1-I-14

N-phenyl-9,9'-spirobi[fluoren]-4-amine (100 g, 245.4 mmol), 1-bromo-3-chloro-5-methylbenzene (60.5 g, 294.5 mmol), Pd$_2$(dba)$_3$ (6.7 g, 7.4 mmol), 50% P(t-Bu)$_3$ (7.2 ml, 14.7 mmol), and NaOt-Bu (70.8 g, 736.2 mmol) were added to toluene (900 ml) and reacted as in the synthesis method for Sub 1-I-i to afford 91.8 g of the product Sub 1-I-14 (yield: 70.3%).

(2) Synthesis of Sub 1-II-14

Sub 1-I-14 (90 g, 169.2 mmol) obtained in the above synthesis was added, together with [1,1'-biphenyl]-4-amine (28.6 g, 169.2 mmol), Pd$_2$(dba)$_3$ (4.7 g, 5.1 mmol), 50% P(t-Bu)$_3$ (4.9 ml, 10.2 mmol), and NaOt-Bu (48.8 g, 507.4 mmol), to toluene (560 ml) and the mixture was reacted as in the synthesis method for Sub 1-II-1 to afford 95.4 g of the product Sub 1-II-14 (yield: 84.8%).

(3) Synthesis of Sub 1-14

Sub 1-II-14 (95 g, 142.9 mmol) obtained in the above synthesis was added, together with 1-bromo-3-chloro-5-methylbenzene (29.4 g, 142.9 mmol), Pd$_2$(dba)$_3$ (3.9 g, 4.3 mmol), 50% P(t-Bu)$_3$ (4.2 ml, 8.6 mmol), and NaOt-Bu (41.2 g, 428.7 mmol), to toluene (480 ml) and the mixture was reacted as in the synthesis method for Sub 1-1 to afford 88.8 g of the product Sub 1-14 (yield: 78.7%).

3. Synthesis Example: Sub 1-19

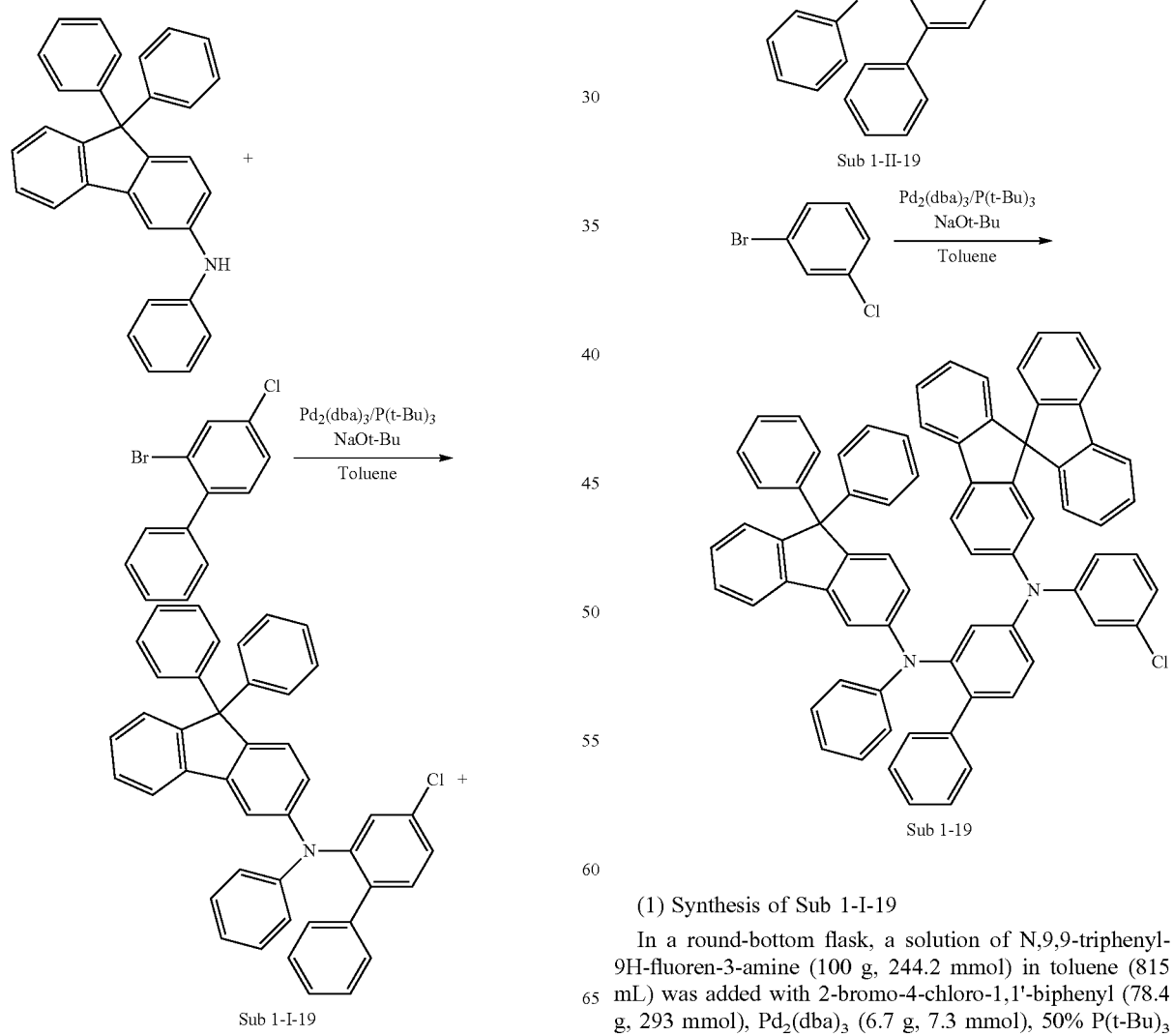

(1) Synthesis of Sub 1-I-19

In a round-bottom flask, a solution of N,9,9-triphenyl-9H-fluoren-3-amine (100 g, 244.2 mmol) in toluene (815 mL) was added with 2-bromo-4-chloro-1,1'-biphenyl (78.4 g, 293 mmol), Pd$_2$(dba)$_3$ (6.7 g, 7.3 mmol), 50% P(t-Bu)$_3$ (7.1 ml, 14.6 mmol), and NaOt-Bu (70.4 g, 732.6 mmol) and the mixture was reacted as in the synthesis method for Sub 1-I-i to afford 100 g of the product Sub 1-I-19 (yield: 68.7%).

(2) Synthesis of Sub 1-II-19

Sub 1-I-19 (100 g, 167.7 mmol) obtained in the above synthesis was added, together with 9,9'-spirobi[fluoren]-2-amine (55.6 g, 167.7 mmol), Pd$_2$(dba)$_3$ (4.6 g, 5.03 mmol), 50% P(t-Bu)$_3$ (5 ml, 10.1 mmol), and NaOt-Bu (48.4 g, 503.2 mmol), to toluene (560 ml) and the mixture was reacted as in the synthesis method for Sub 1-II-1 to afford 120 g of the product Sub 1-II-19 (yield: 80.3%).

(3) Synthesis of Sub 1-19

Sub-II-19 (120 g, 134.7 mmol) obtained in the above synthesis was added, together with 1-bromo-3-chlorobenzene (25.8 g, 134.7 mmol), Pd$_2$(dba)$_3$ (3.7 g, 4 mmol), 50% P(t-Bu)$_3$ (3.9 ml, 8.1 mmol), and NaOt-Bu (38.8 g, 404 mmol), to toluene (450 ml) and the mixture was reacted as in the synthesis method for Sub 1-1 to afford 130 g of the product Sub 1-19 (yield: 96.4%).

4. Synthesis Example: Sub 1-21

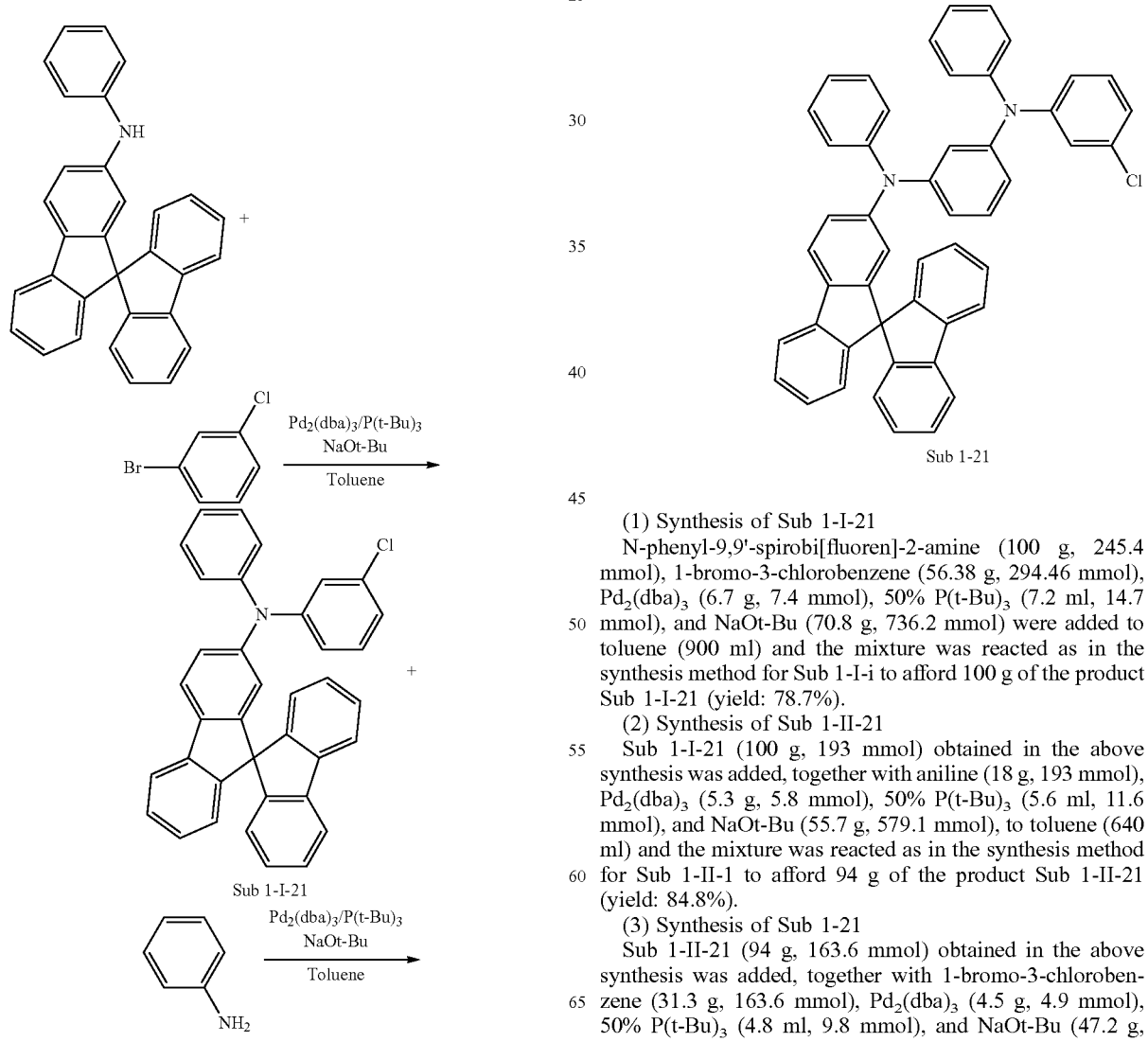

(1) Synthesis of Sub 1-I-21

N-phenyl-9,9'-spirobi[fluoren]-2-amine (100 g, 245.4 mmol), 1-bromo-3-chlorobenzene (56.38 g, 294.46 mmol), Pd$_2$(dba)$_3$ (6.7 g, 7.4 mmol), 50% P(t-Bu)$_3$ (7.2 ml, 14.7 mmol), and NaOt-Bu (70.8 g, 736.2 mmol) were added to toluene (900 ml) and the mixture was reacted as in the synthesis method for Sub 1-I-i to afford 100 g of the product Sub 1-I-21 (yield: 78.7%).

(2) Synthesis of Sub 1-II-21

Sub 1-I-21 (100 g, 193 mmol) obtained in the above synthesis was added, together with aniline (18 g, 193 mmol), Pd$_2$(dba)$_3$ (5.3 g, 5.8 mmol), 50% P(t-Bu)$_3$ (5.6 ml, 11.6 mmol), and NaOt-Bu (55.7 g, 579.1 mmol), to toluene (640 ml) and the mixture was reacted as in the synthesis method for Sub 1-II-1 to afford 94 g of the product Sub 1-II-21 (yield: 84.8%).

(3) Synthesis of Sub 1-21

Sub 1-II-21 (94 g, 163.6 mmol) obtained in the above synthesis was added, together with 1-bromo-3-chlorobenzene (31.3 g, 163.6 mmol), Pd$_2$(dba)$_3$ (4.5 g, 4.9 mmol), 50% P(t-Bu)$_3$ (4.8 ml, 9.8 mmol), and NaOt-Bu (47.2 g, 490.7 mmol), to toluene (545 ml) and the mixture was reacted as in the synthesis method for Sub 1-1 to afford 99.8 g of the product Sub 1-21 (yield: 89%).

5. Synthesis Example: Sub 1-40

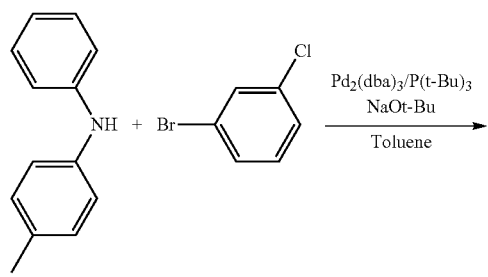

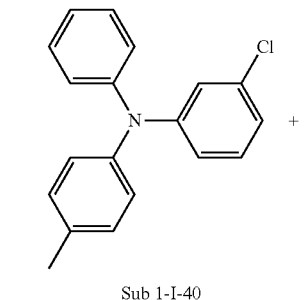

Sub 1-I-40

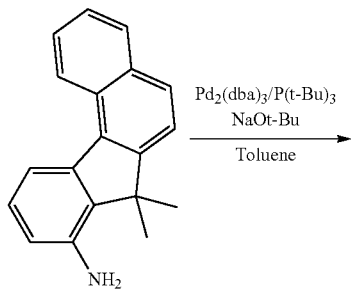

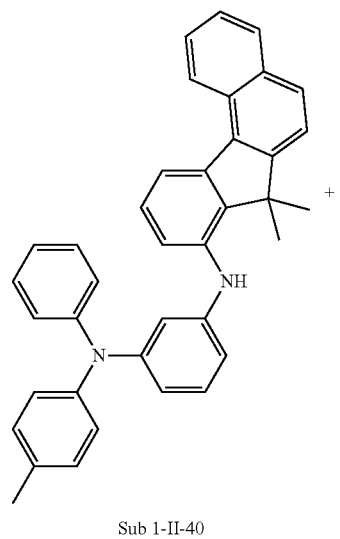

Sub 1-II-40

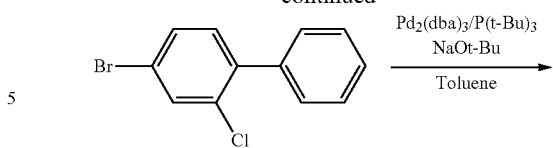

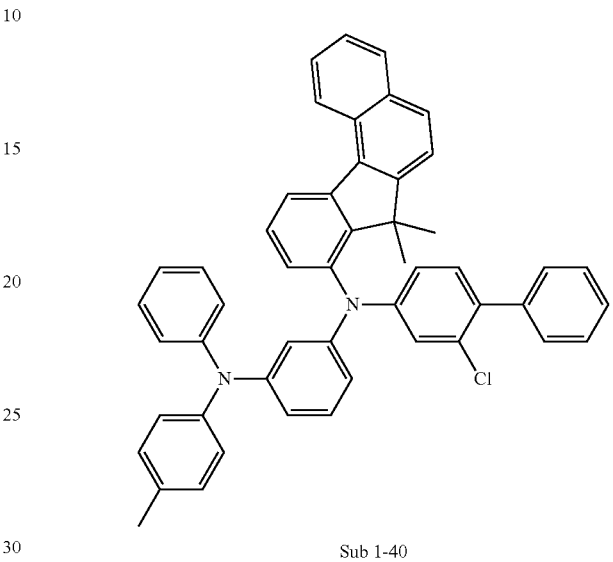

Sub 1-40

(1) Synthesis of Sub 1-I-40

4-Methyl-N-phenylaniline (100 g, 545.7 mmol), 1-bromo-3-chlorobenzene (125.4 g, 654.8 mmol), Pd$_2$(dba)$_3$ (15 g, 16.4 mmol), 50% P(t-Bu)$_3$ (16 ml, 32.7 mmol), and NaOt-Bu (157.3 g, 1637 mmol) were added to toluene (1800 ml) and the mixture was reacted as in the synthesis method for Sub 1-I-i to afford 130.2 g of the product Sub 1-I-40 (yield: 81.2%).

(2) Synthesis of Sub 1-II-40

Sub 1-I-40 (100 g, 340.4 mmol) obtained in the above synthesis was added, together with 7,7-dimethyl-7H-benzo[c]fluoren-8-amine (88.3 g, 340.4 mmol), Pd$_2$(dba)$_3$ (9.4 g, 10.2 mmol), 50% P(t-Bu)$_3$ (10 ml, 20.4 mmol), and NaOt-Bu (98.1 g, 1021 mmol), to toluene (1130 ml) and the mixture was reacted as in the synthesis method for Sub 1-I-i to afford 139.8 g of the product Sub 1-II-40 (yield: 79.5%).

(3) Synthesis of Sub 1-40

Sub 1-II-40 (100 g, 193.5 mmol) obtained in the above synthesis was added, together with, 2-bromo-4-chloro-1,1'-biphenyl (51.8 g, 193.5 mmol), Pd$_2$(dba)$_3$ (5.3 g, 5.8 mmol), 50% P(t-Bu)$_3$ (5.7 ml, 11.6 mmol), and NaOt-Bu (55.8 g, 581 mmol), to toluene (645 ml) and the mixture was reacted as in the synthesis method for Sub 1-1 to afford 97.9 g of the product Sub 1-40 (yield: 71.9%).

6. Synthesis Example: Sub 1-44

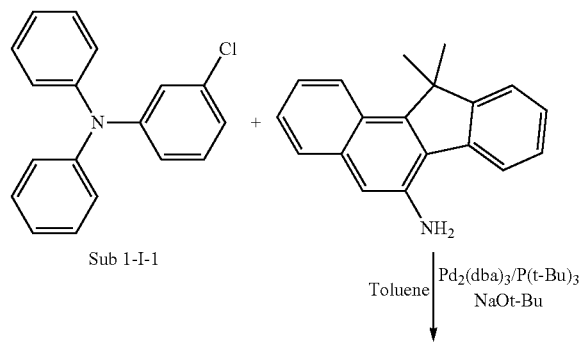

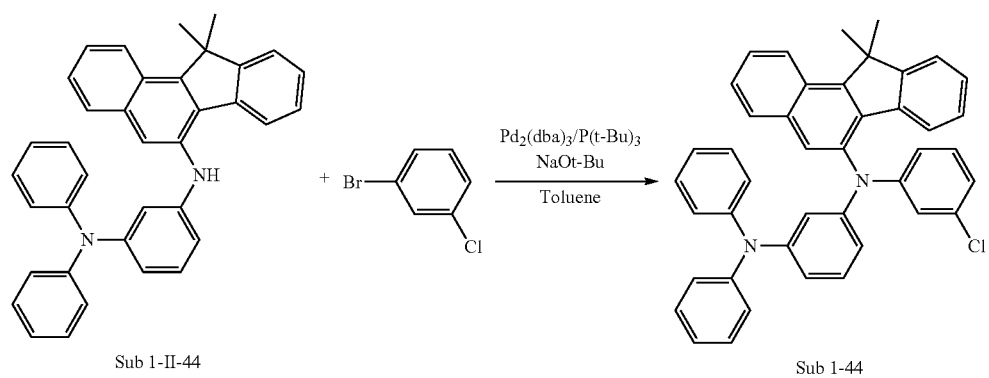

(1) Synthesis of Sub 1-II-44

Sub 1-I-1 (100 g, 357.4 mmol) obtained in the above synthesis was added, together with, 11,11-dimethyl-11H-benzo[a]fluoren-6-amine (92.7 g, 357.4 mmol), $Pd_2(dba)_3$ (9.8 g, 10.7 mmol), 50% $P(t-Bu)_3$ (10.5 ml, 21.5 mmol), and NaOt-Bu (103.1 g, 1072.3 mmol), to toluene (1190 ml) and the mixture was reacted as in the synthesis method for Sub 1-II-1 to afford 144.8 g of the product Sub 1-II-44 (yield: 80.6%).

(2) Synthesis of Sub 1-44

Sub 1-II-44 (100 g, 198.9 mmol) obtained in the above synthesis was added, together with 1-bromo-3-chlorobenzene (38.09 g, 198.9 mmol), $Pd_2(dba)_3$ (5.47 g, 5.97 mmol), 50% $P(t-Bu)_3$ (5.8 ml, 11.94 mmol), and NaOt-Bu (57.36 g, 596.82 mmol), to toluene (660 ml) and the mixture was reacted as in the synthesis method for Sub 1-1 to afford 115.2 g of the product Sub 1-44 (yield: 94.4%).

7. Synthesis Example: Sub 1-48

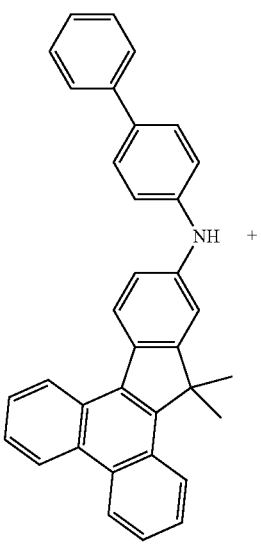

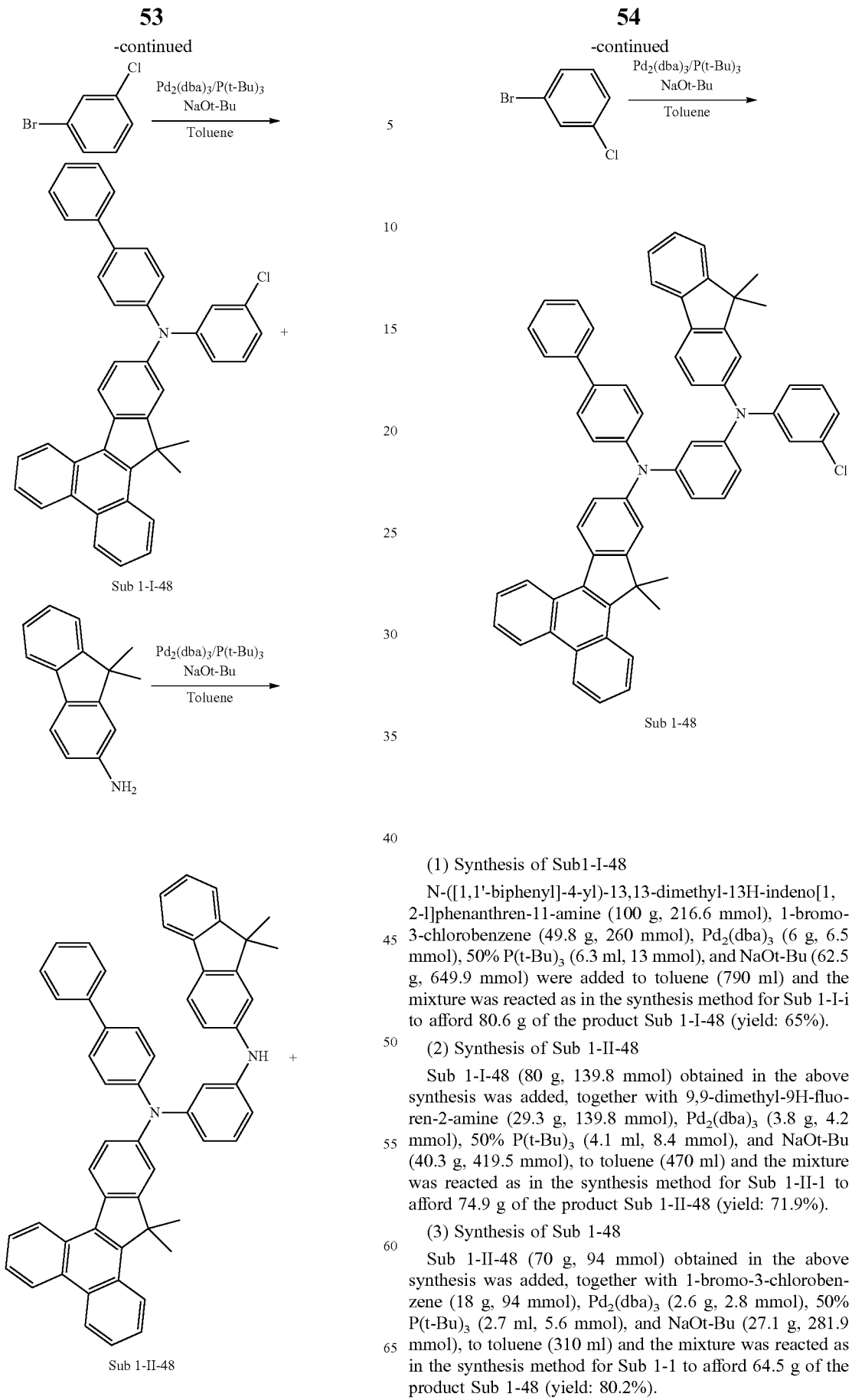

(1) Synthesis of Sub1-I-48

N-([1,1'-biphenyl]-4-yl)-13,13-dimethyl-13H-indeno[1,2-l]phenanthren-11-amine (100 g, 216.6 mmol), 1-bromo-3-chlorobenzene (49.8 g, 260 mmol), $Pd_2(dba)_3$ (6 g, 6.5 mmol), 50% P(t-Bu)$_3$ (6.3 ml, 13 mmol), and NaOt-Bu (62.5 g, 649.9 mmol) were added to toluene (790 ml) and the mixture was reacted as in the synthesis method for Sub 1-I-i to afford 80.6 g of the product Sub 1-I-48 (yield: 65%).

(2) Synthesis of Sub 1-II-48

Sub 1-I-48 (80 g, 139.8 mmol) obtained in the above synthesis was added, together with 9,9-dimethyl-9H-fluoren-2-amine (29.3 g, 139.8 mmol), $Pd_2(dba)_3$ (3.8 g, 4.2 mmol), 50% P(t-Bu)$_3$ (4.1 ml, 8.4 mmol), and NaOt-Bu (40.3 g, 419.5 mmol), to toluene (470 ml) and the mixture was reacted as in the synthesis method for Sub 1-II-1 to afford 74.9 g of the product Sub 1-II-48 (yield: 71.9%).

(3) Synthesis of Sub 1-48

Sub 1-II-48 (70 g, 94 mmol) obtained in the above synthesis was added, together with 1-bromo-3-chlorobenzene (18 g, 94 mmol), $Pd_2(dba)_3$ (2.6 g, 2.8 mmol), 50% P(t-Bu)$_3$ (2.7 ml, 5.6 mmol), and NaOt-Bu (27.1 g, 281.9 mmol), to toluene (310 ml) and the mixture was reacted as in the synthesis method for Sub 1-1 to afford 64.5 g of the product Sub 1-48 (yield: 80.2%).

8. Synthesis Example: Sub 1-66

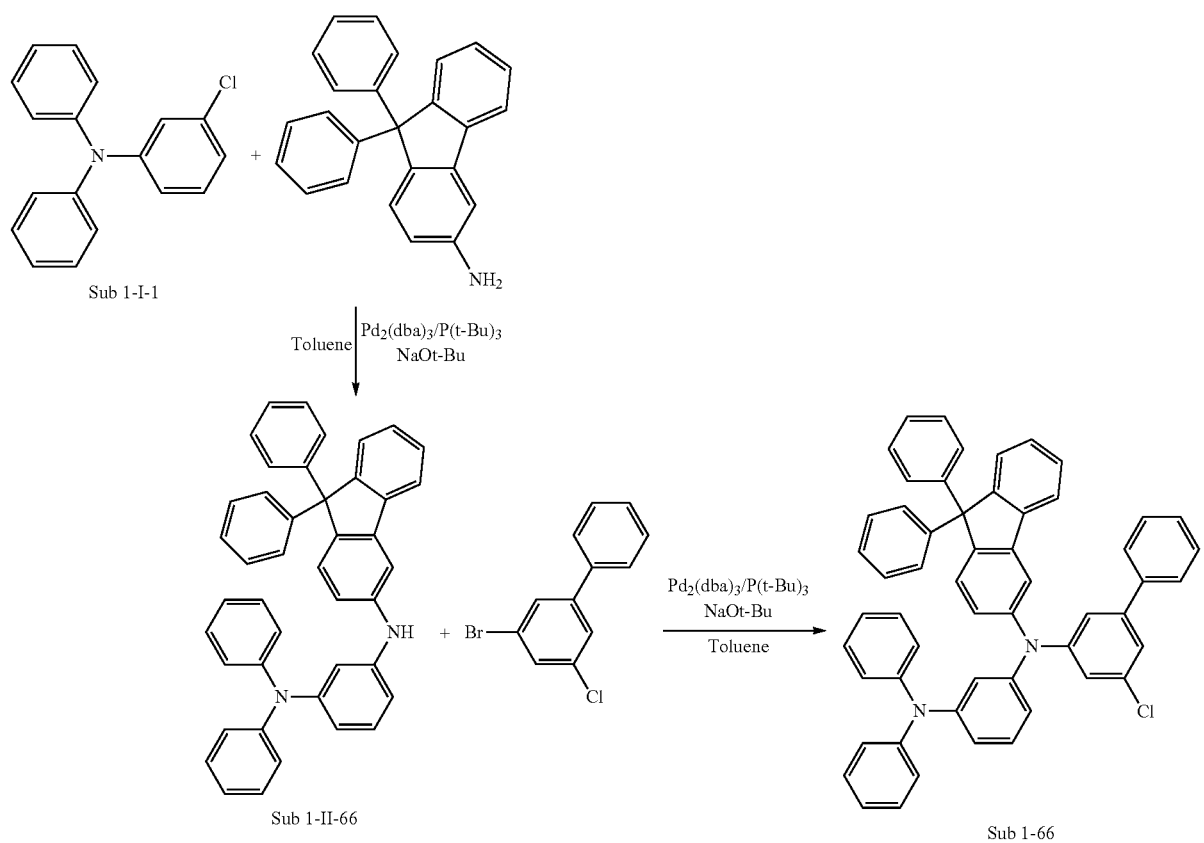

(1) Synthesis of Sub 1-II-66

Sub 1-I-1 (150 g, 536.2 mmol) obtained in the above synthesis was added, together with 9,9-diphenyl-9H-fluoren-3-amine (178.8 g, 536.2 mmol), Pd$_2$(dba)$_3$ (14.7 g, 16.1 mmol), 50% P(t-Bu)$_3$ (15.7 ml, 32.2 mmol), and NaOt-Bu (154.6 g, 1608.5 mmol), to toluene (1790 ml) and the mixture was reacted as in the synthesis method for Sub 1-II-1 to afford 280.2 g of the product Sub 1-II-66 (yield: 90.6%).

(2) Synthesis of Sub 1-66

Sub 1-II-66 (100 g, 173.4 mmol) obtained in the above synthesis was added, together with 3-bromo-5-chloro-1,1'-biphenyl (46.4 g, 173.4 mmol), Pd$_2$(dba)$_3$ (4.8 g, 5.2 mmol), 50% P(t-Bu)$_3$ (5.1 ml, 10.4 mmol), and NaOt-Bu (50 g, 520.2 mmol), to toluene (580 ml) and the mixture was reacted as in the synthesis method for Sub 1-1 to afford 99.4 g of the product Sub 1-66 (yield: 75.1%).

9. Synthesis Example: Sub 1-67

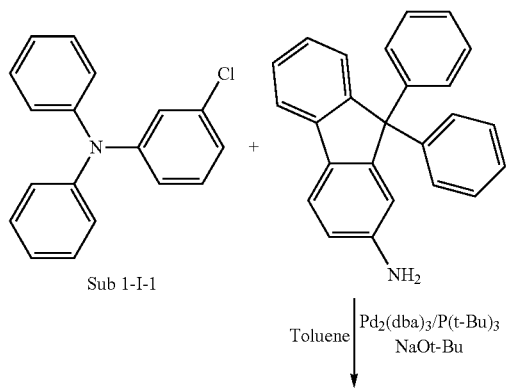

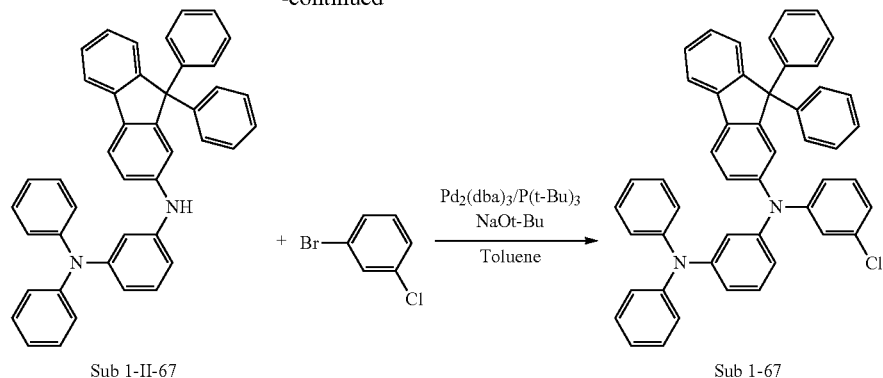

Sub 1-II-67 → Sub 1-67

(1) Synthesis of Sub 1-II-67

Sub 1-I-1 (100 g, 357.4 mmol) obtained in the above synthesis was added, together with 9,9-diphenyl-9H-fluoren-2-amine (119.2 g, 357.4 mmol), Pd$_2$(dba)$_3$ (9.8 g, 10.7 mmol), 50% P(t-Bu)$_3$ (10.5 ml, 21.5 mmol), and NaOt-Bu (103.1 g, 1072.3 mmol), to toluene (1190 ml) and the mixture was reacted as in the synthesis method for Sub 1-II-1 to afford 168.8 g of the product Sub 1-II-67 (yield: 81.9%).

(2) Synthesis of Sub 1-67

Sub 1-II-67 (100 g, 173.4 mmol) obtained in the above synthesis was added, together with 1-bromo-3-chlorobenzene (33.2 g, 173.4 mmol), Pd$_2$(dba)$_3$ (4.8 g, 5.2 mmol), 50% P(t-Bu)$_3$ (5.1 ml, 10.4 mmol), and NaOt-Bu (50 g, 520.2 mmol), to toluene (580 ml) and the mixture was reacted as in the synthesis method for Sub 1-1 to afford 109.8 g of the product Sub 1-67 (yield: 92.1%).

10. Synthesis Example: Sub 1-75

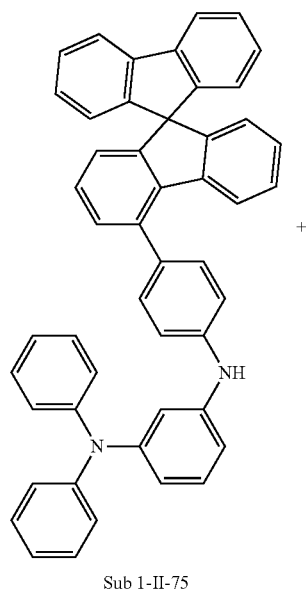

Sub 1-II-75

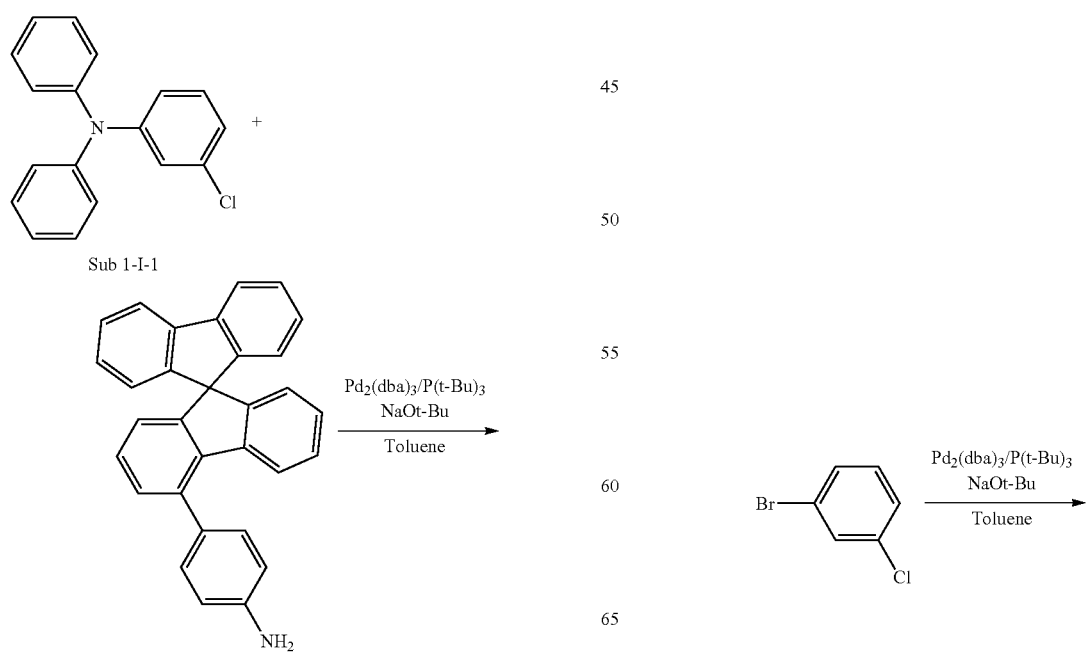

Sub 1-I-1

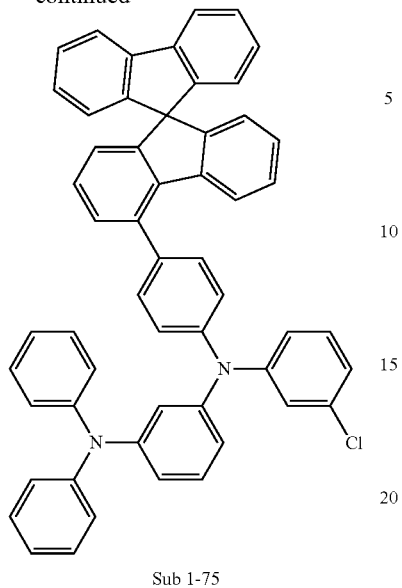

Sub 1-75

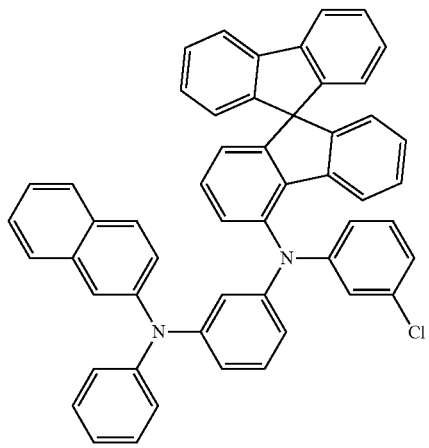

Sub 1-2

(1) Synthesis of Sub 1-II-75

Sub 1-I-1 (100 g, 357.4 mmol) obtained in the above synthesis was added, together with 4-(9,9'-spirobi[fluoren]-4-yl)aniline (145.66 g, 357.4 mmol), Pd$_2$(dba)$_3$ (9.8 g, 10.7 mmol), 50% P(t-Bu)$_3$ (10.5 ml, 21.5 mmol), and NaOt-Bu (103.1 g, 1072.3 mmol), to toluene (1190 ml) and the mixture was reacted as in the synthesis method for Sub 1-II-1 to afford 199.8 g of the product Sub 1-II-75 (yield: 85.9%).

(2) Synthesis of Sub 1-75

Sub 1-II-75 (100 g, 153.7 mmol) obtained in the above synthesis was added, together with 1-bromo-3-chlorobenzene (29.4 g, 153.7 mmol), Pd$_2$(dba)$_3$ (4.2 g, 4.6 mmol), 50% P(t-Bu)$_3$ (4.5 ml, 9.2 mmol), NaOt-Bu (44.3 g, 461 mmol), to toluene (510 ml) and the mixture was reacted as in the synthesis method for Sub 1-1 to afford 100 g of the product Sub 1-75 (yield: 85.5%).

Meanwhile, examples of Sub 1 include, but are not limited to, the following compounds, and FD-MS (Field Desorption-Mass Spectrometry) values of the compounds of Sub 1 are listed in Table 1, below.

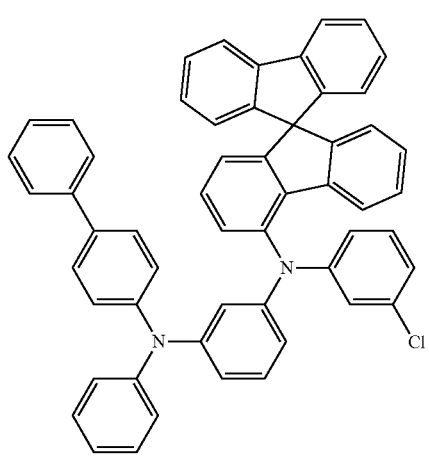

Sub 1-3

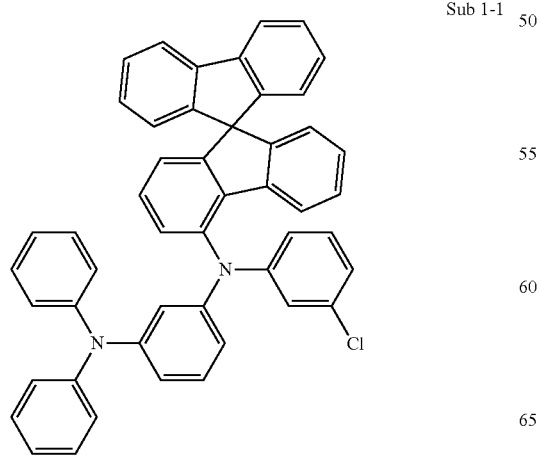

Sub 1-1

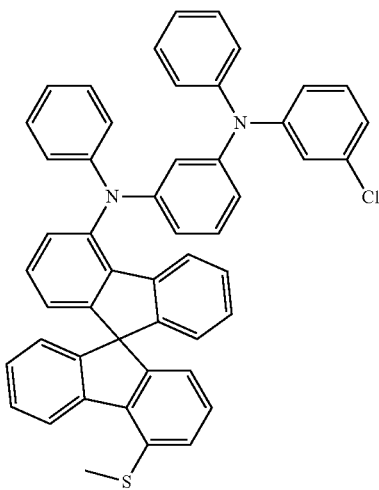

Sub 1-4

Sub 1-5
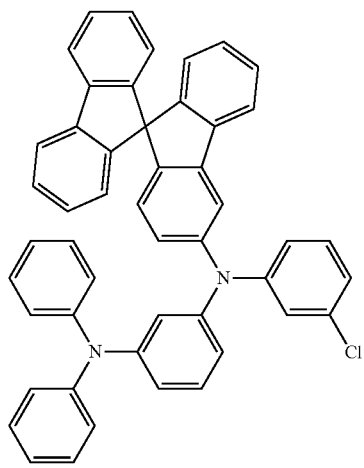
Sub 1-6
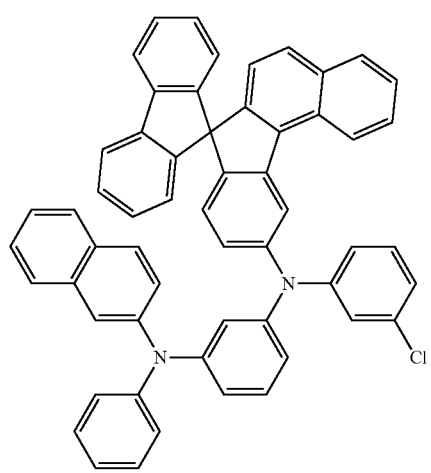
Sub 1-7
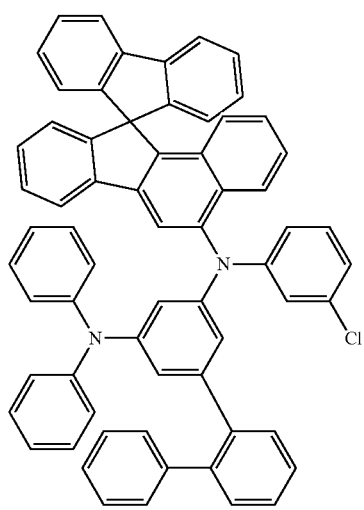
Sub 1-8
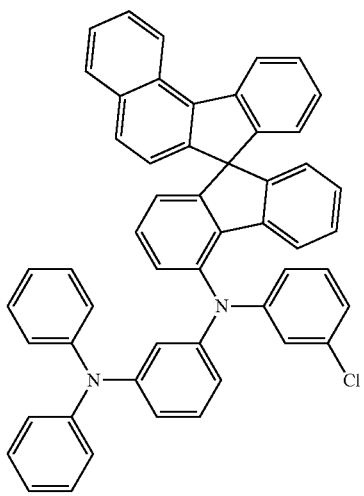
Sub 1-9
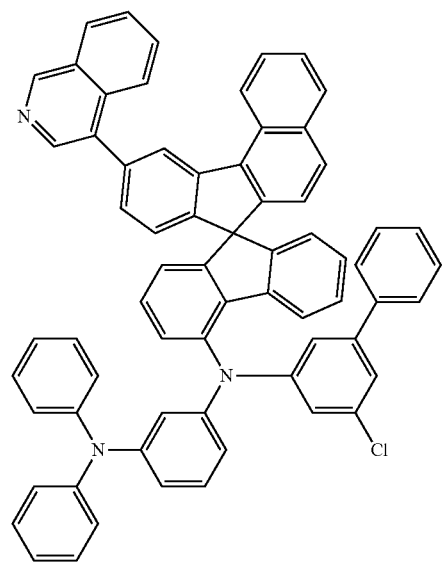
Sub 1-10
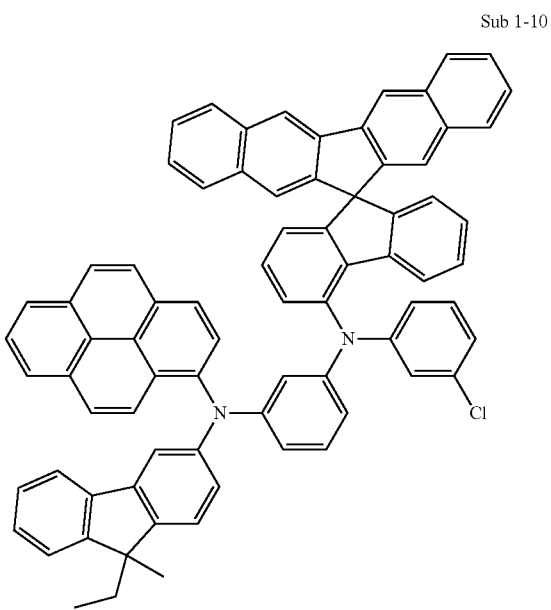

Sub 1-11
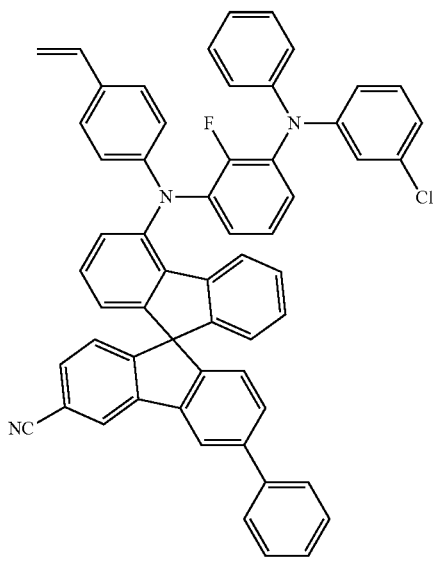
Sub 1-12
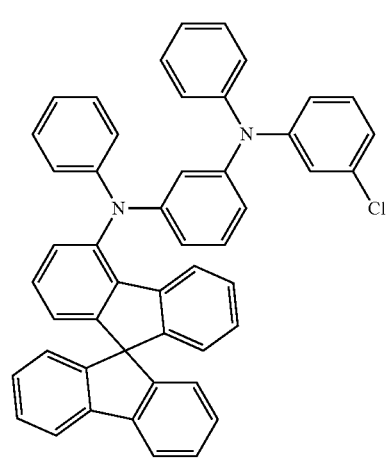
Sub 1-13
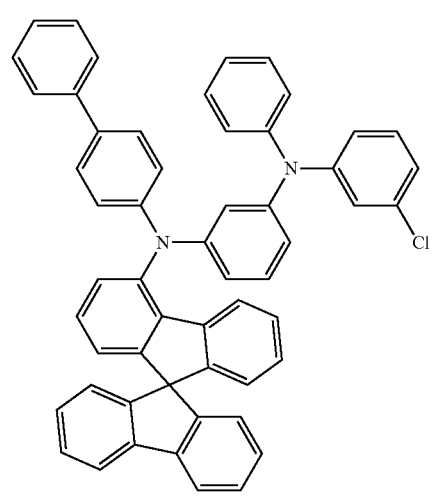
Sub 1-14
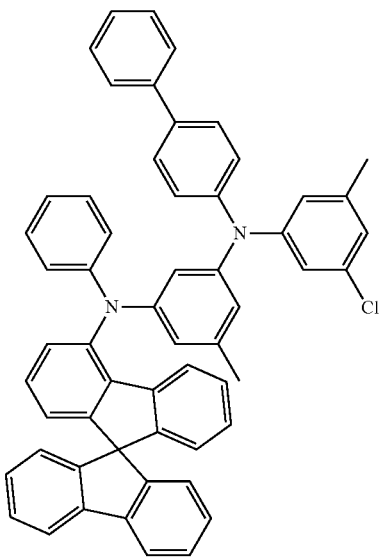
Sub 1-15
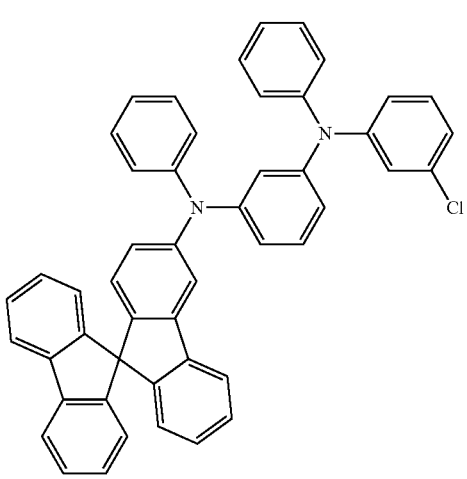
Sub 1-16
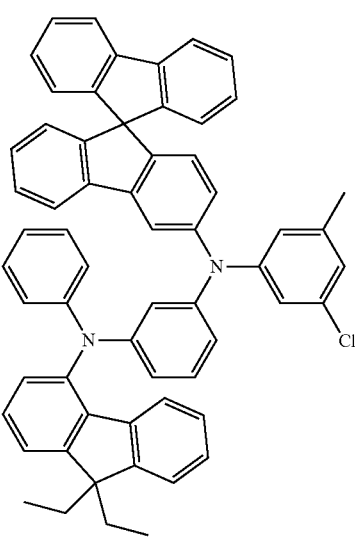

Sub 1-17
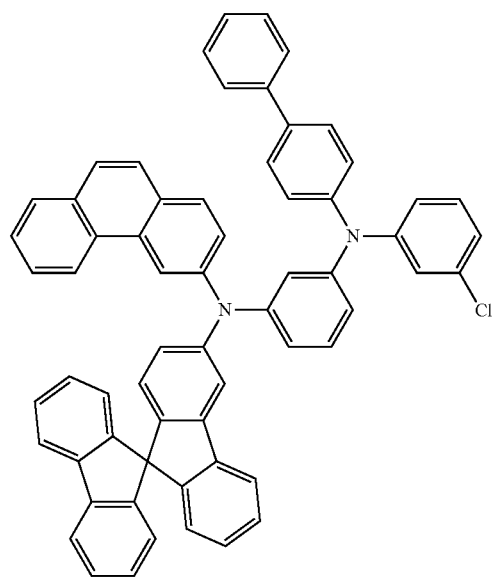
Sub 1-18
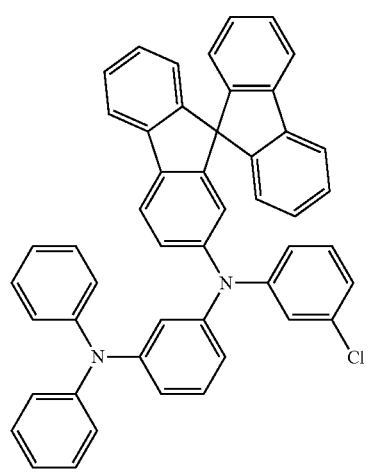
Sub 1-19
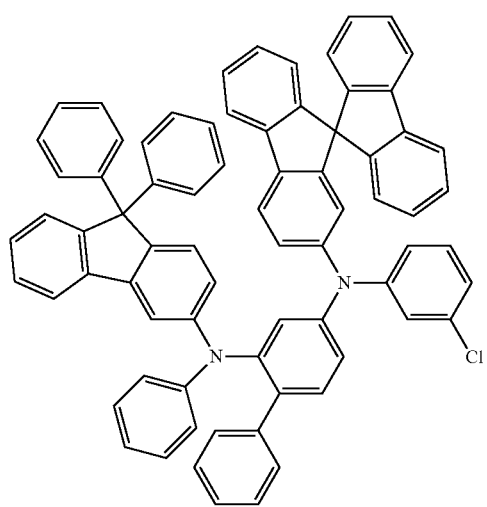
Sub 1-20
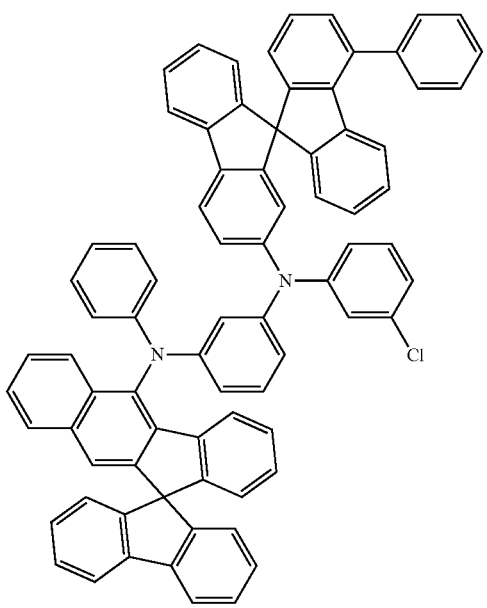
Sub 1-21
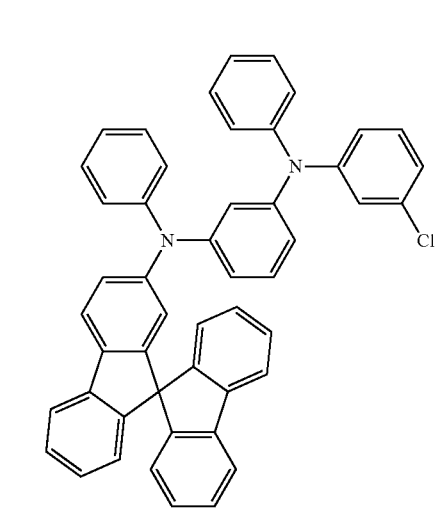

-continued
Sub 1-22
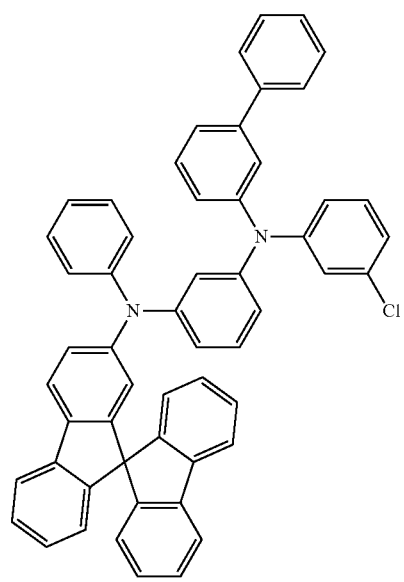
Sub 1-23
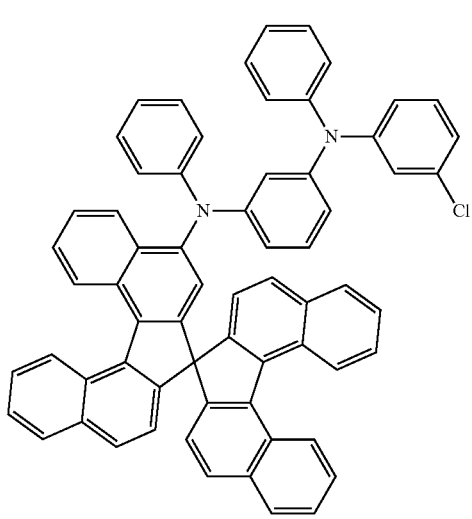
Sub 1-24
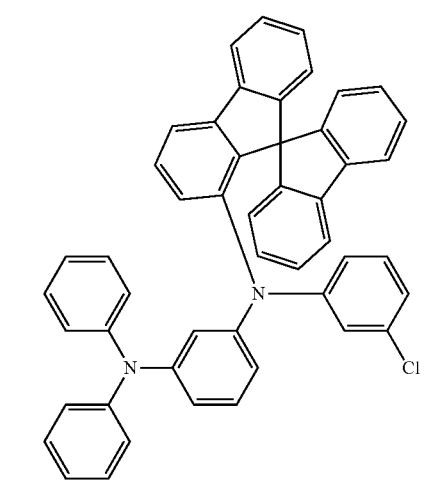
Sub 1-25
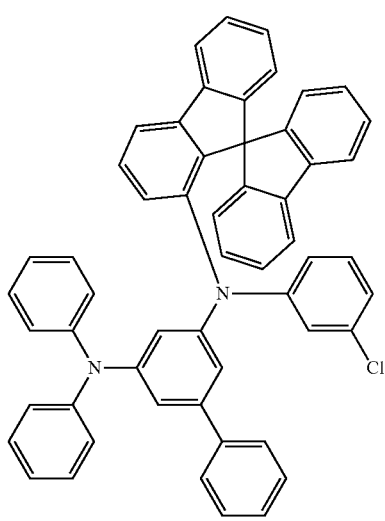
Sub 1-26
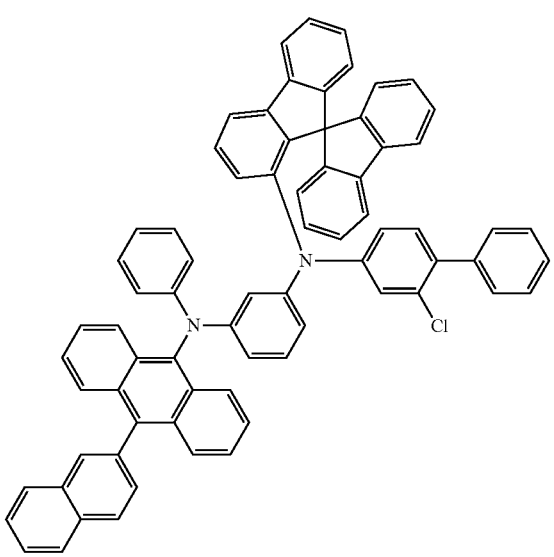
Sub 1-27
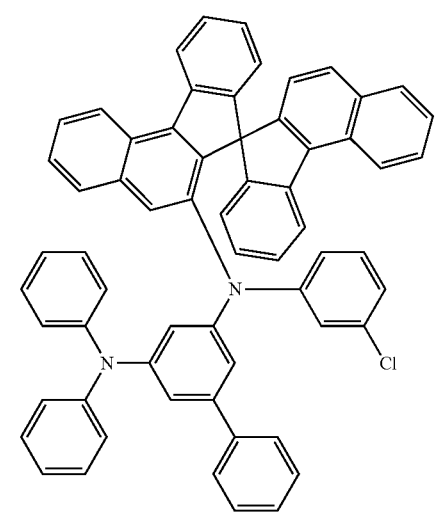

Sub 1-28
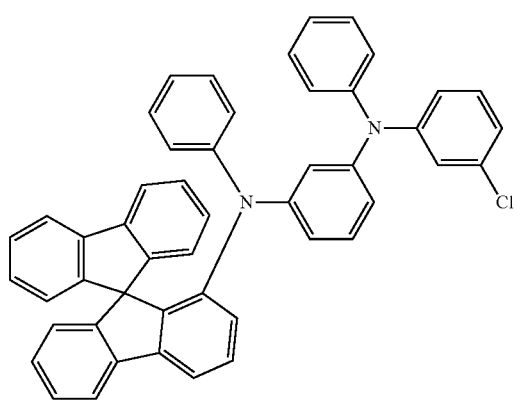
Sub 1-29
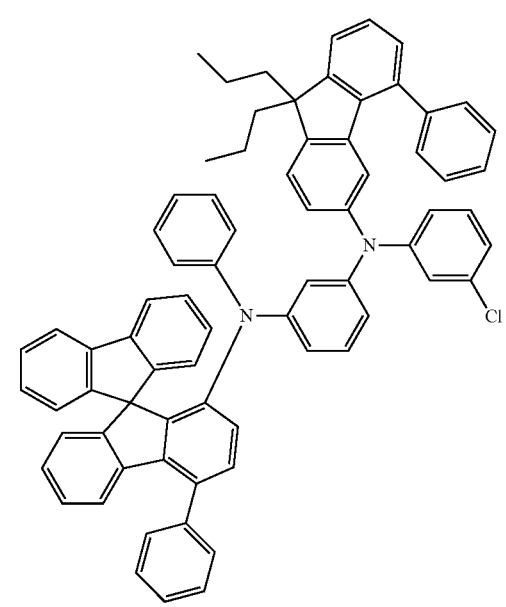
Sub 1-30
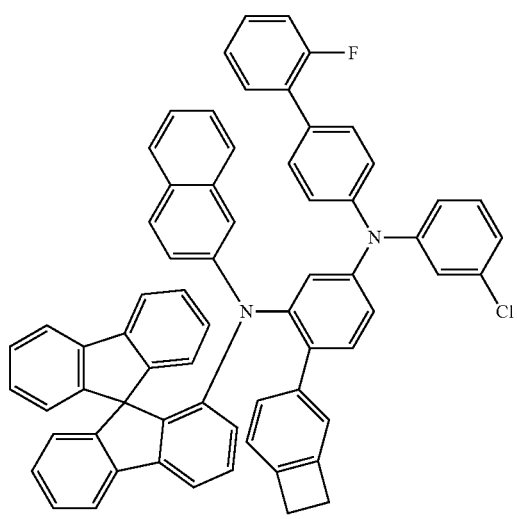
Sub 1-31
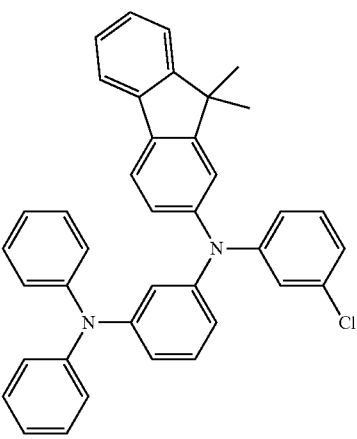
Sub 1-32
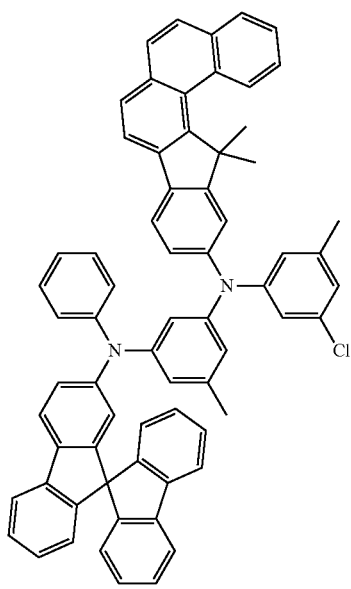
Sub 1-33
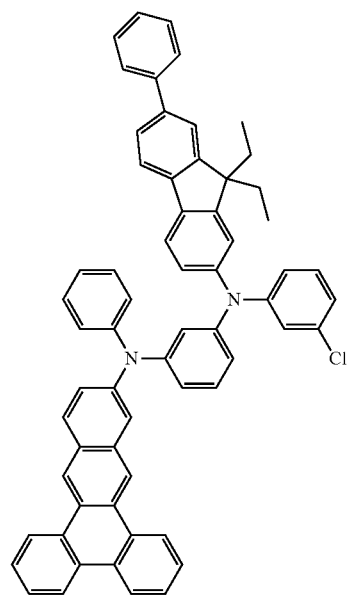

-continued
Sub 1-34
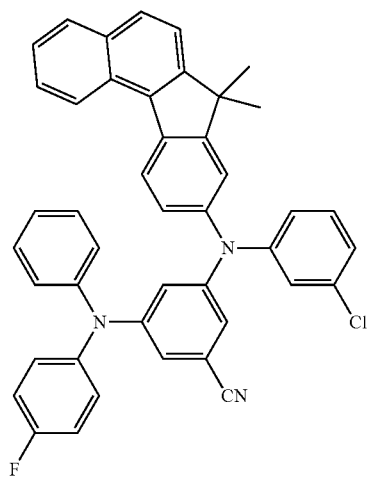
Sub 1-35
Sub 1-36
-continued
Sub 1-37
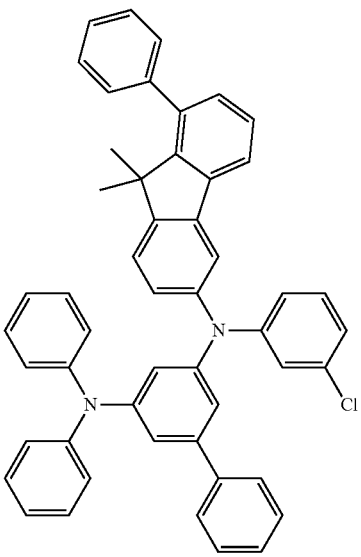
Sub 1-38
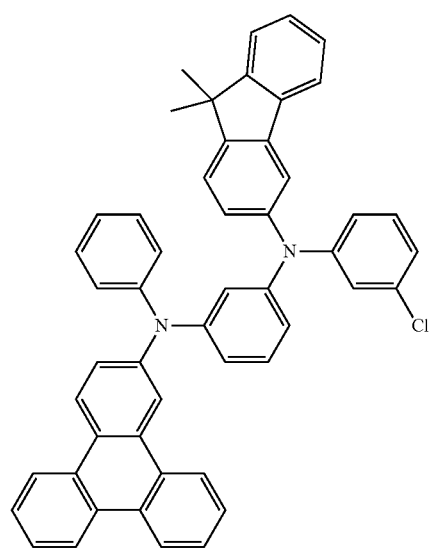
Sub 1-39
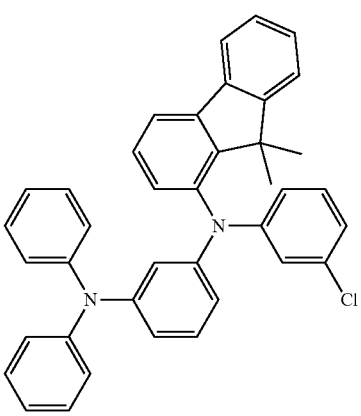

Sub 1-40
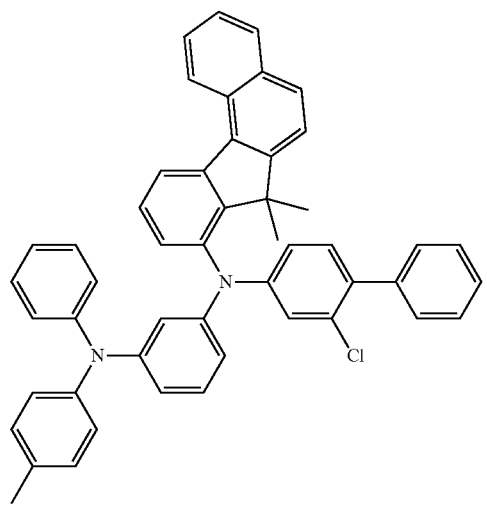
Sub 1-41
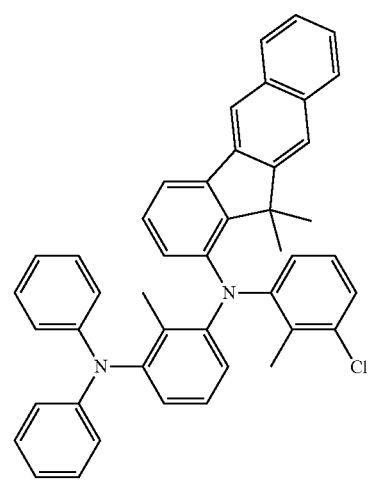
Sub 1-42
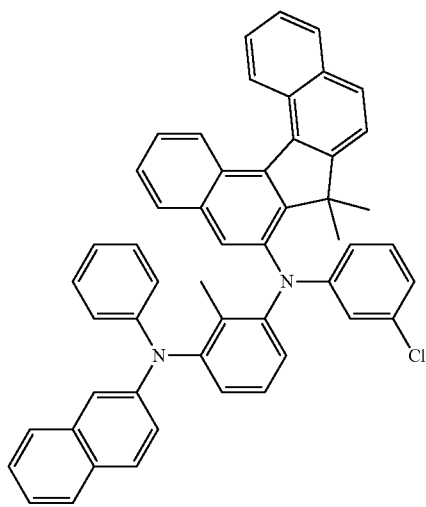
Sub 1-43
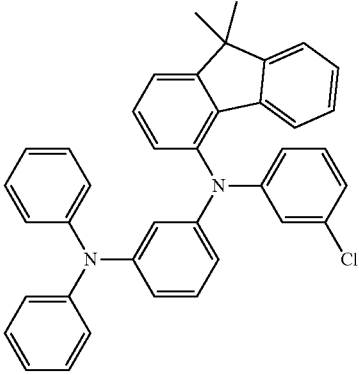
Sub 1-44
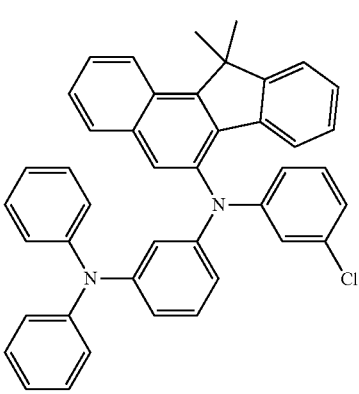
Sub 1-45
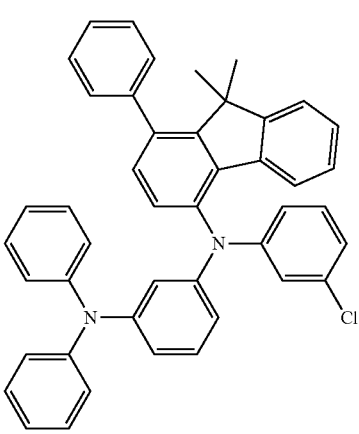
Sub 1-46

Sub 1-47
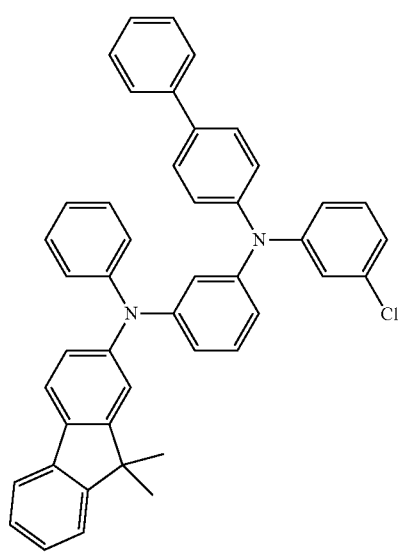
Sub 1-48
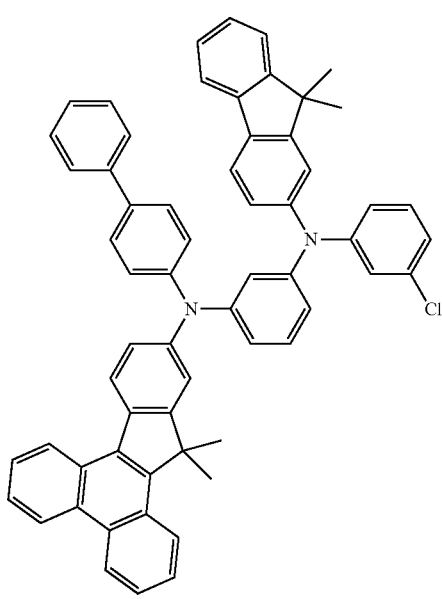
Sub 1-49
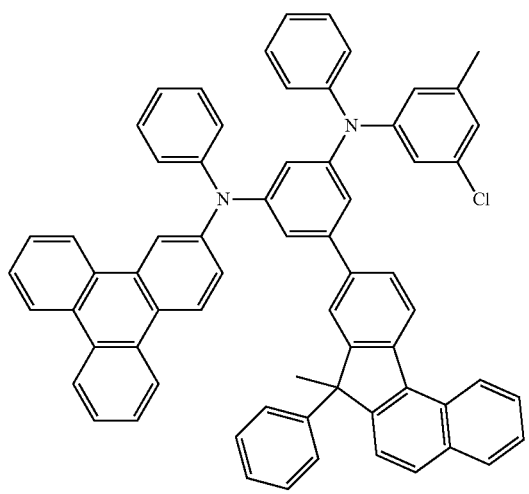
Sub 1-50
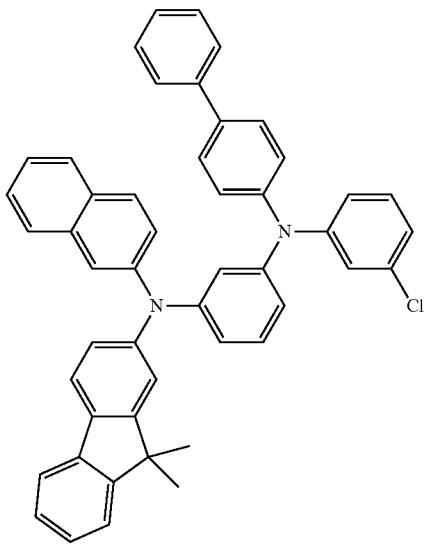
Sub 1-51
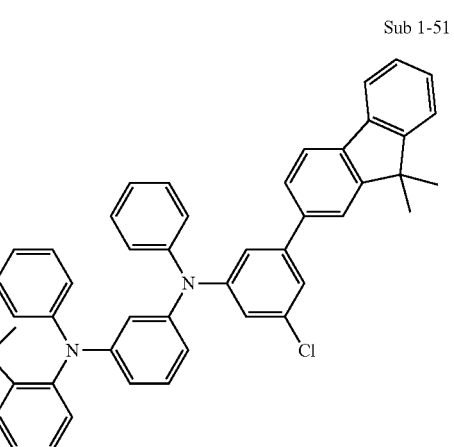
Sub 1-52
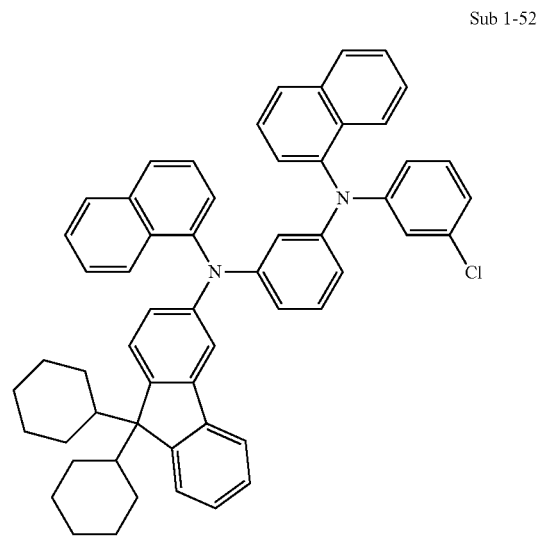

Sub 1-53
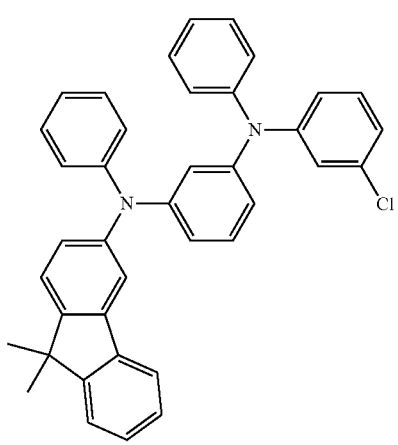
Sub 1-54
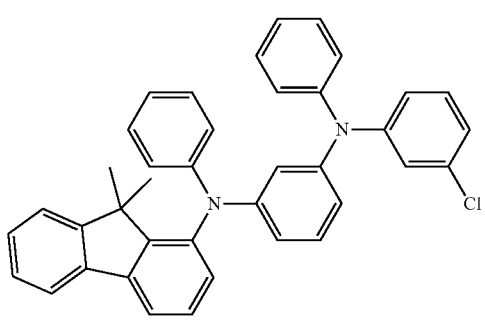
Sub 1-55
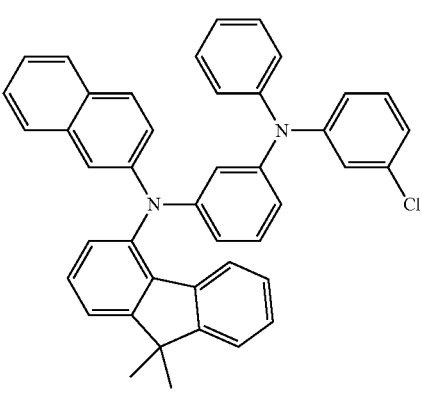
Sub 1-56
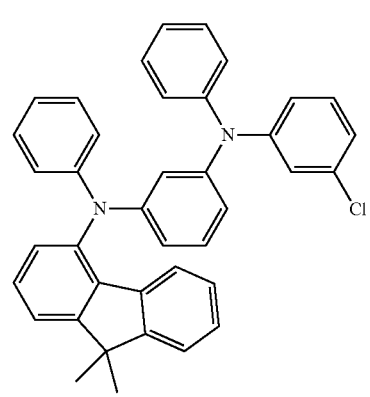
Sub 1-57
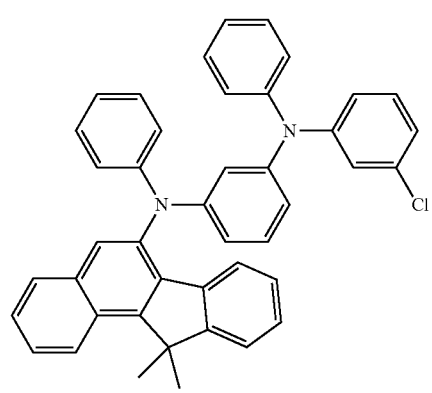
Sub 1-58
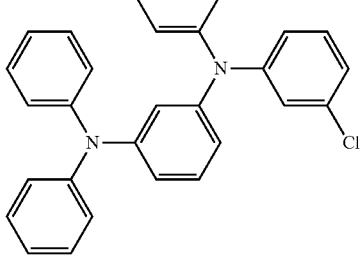
Sub 1-59
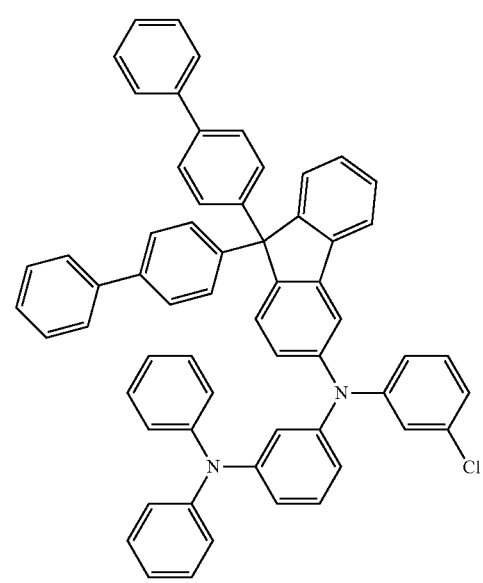

Sub 1-60
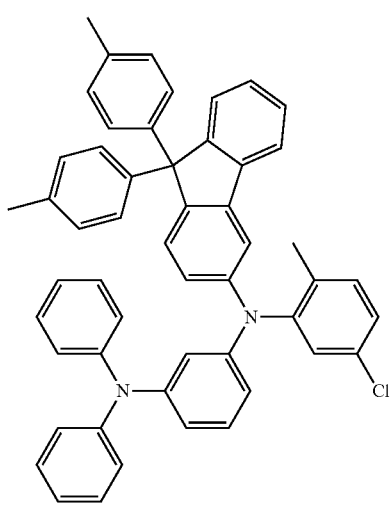
Sub 1-61
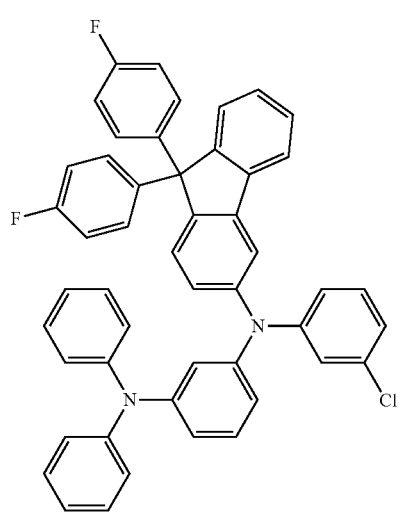
Sub 1-62
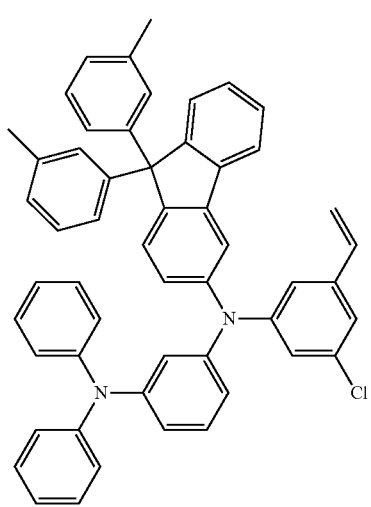
Sub 1-63
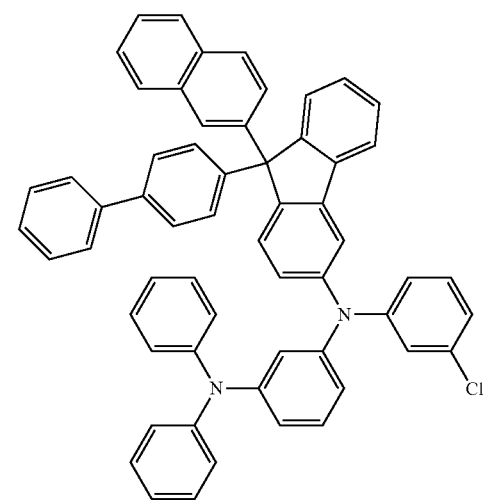
Sub 1-64
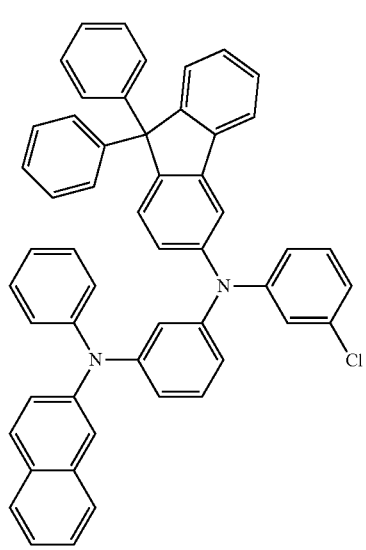
Sub 1-65
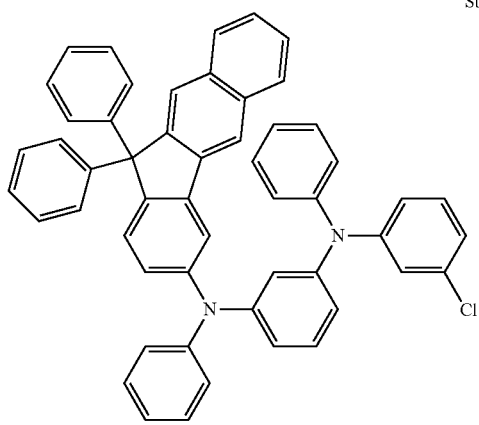

Sub 1-66
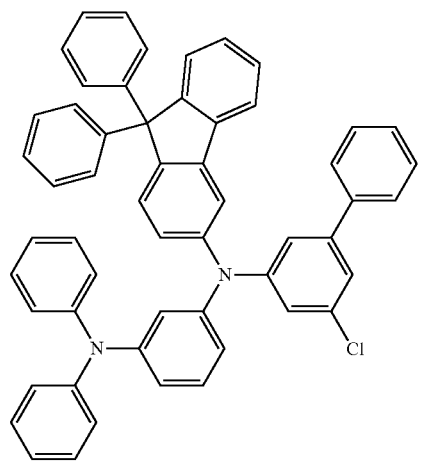
Sub 1-67
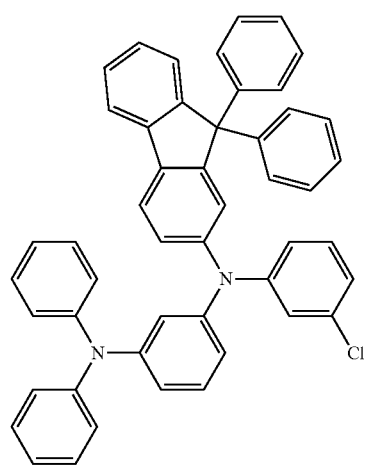
Sub 1-68
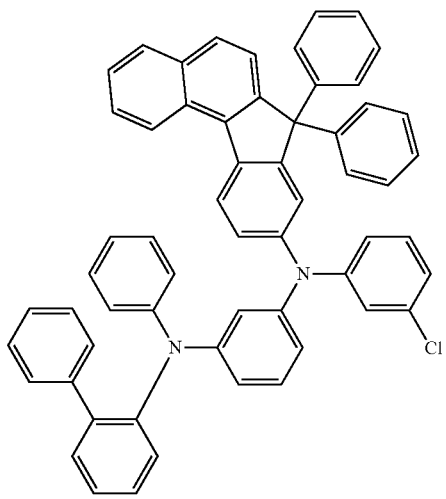
Sub 1-69
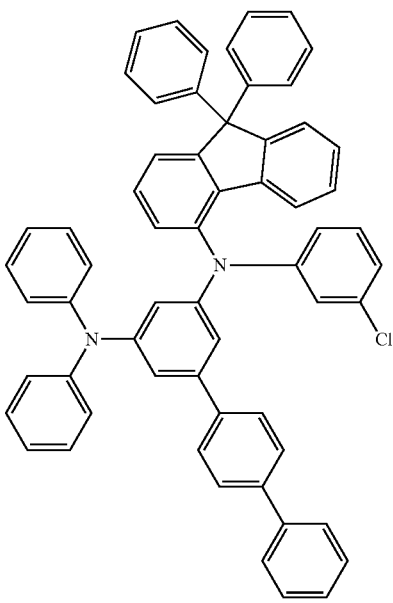
Sub 1-70
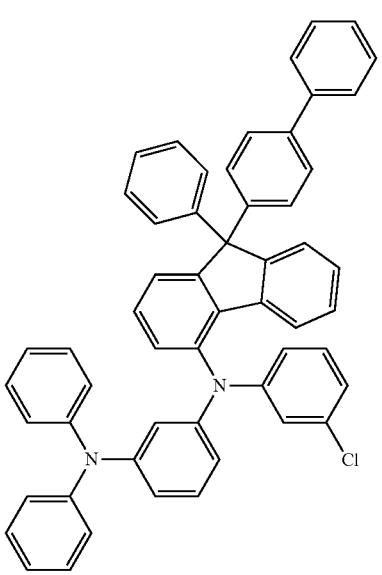

Sub 1-71
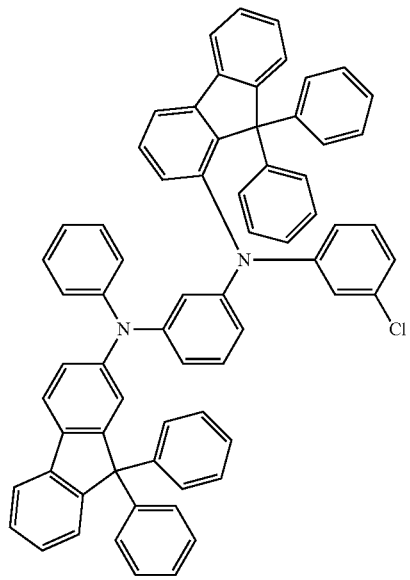
Sub 1-74
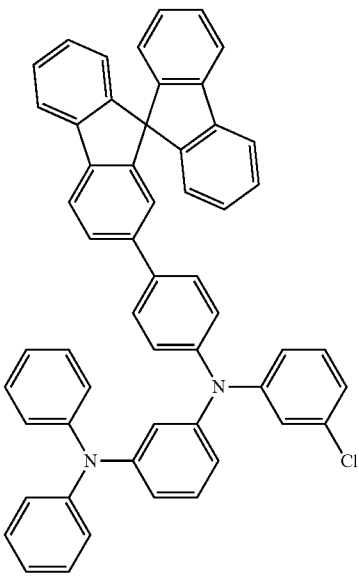
Sub 1-72
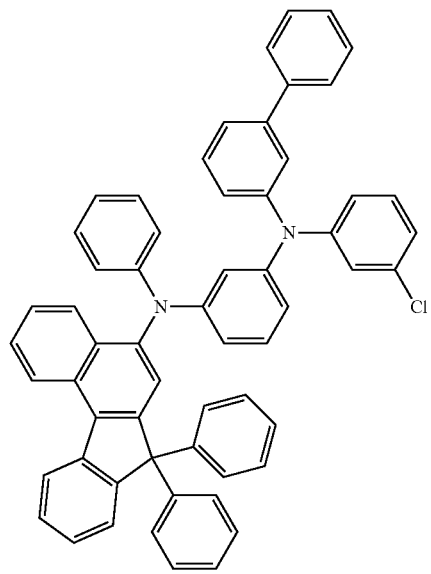
Sub 1-75
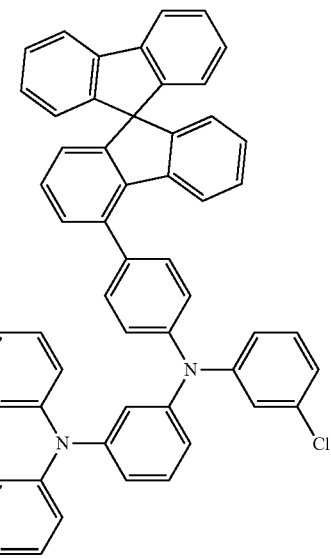
Sub 1-73
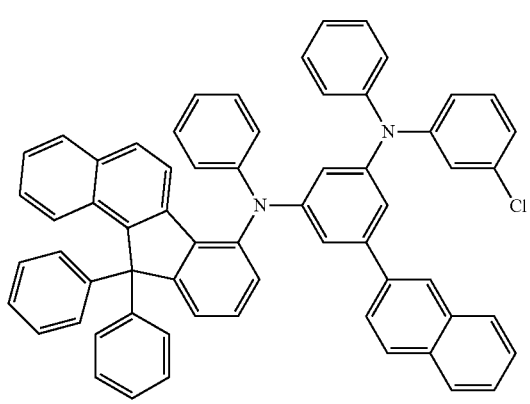
Sub 1-76
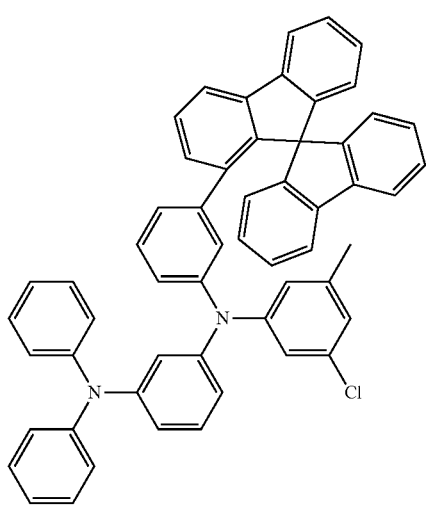

Sub 1-77
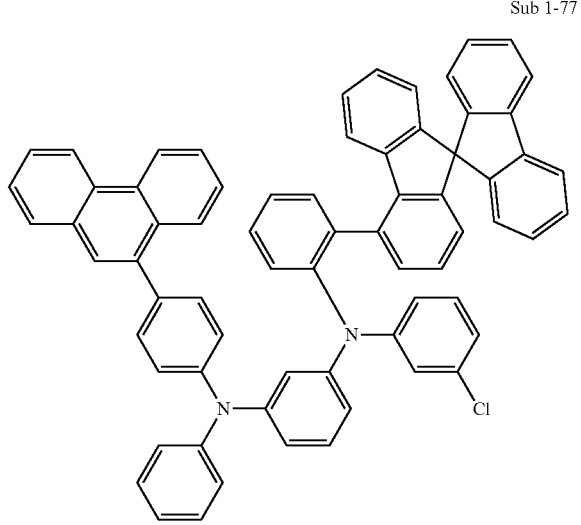
Sub 1-78
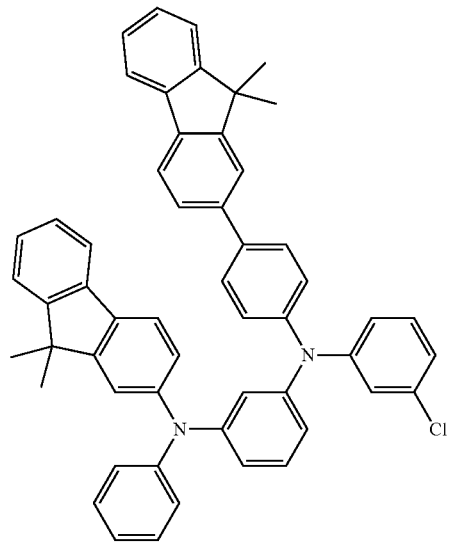
Sub 1-79
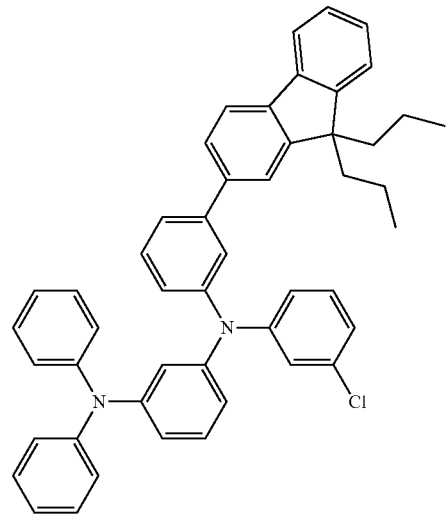
Sub 1-80
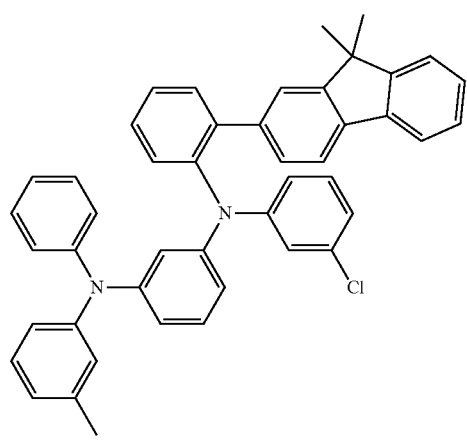
Sub 1-81
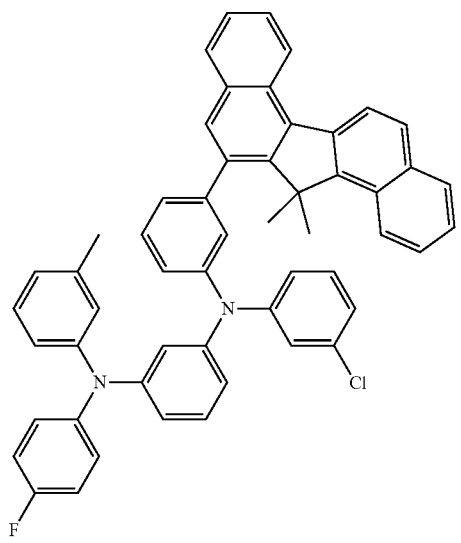
Sub 1-82
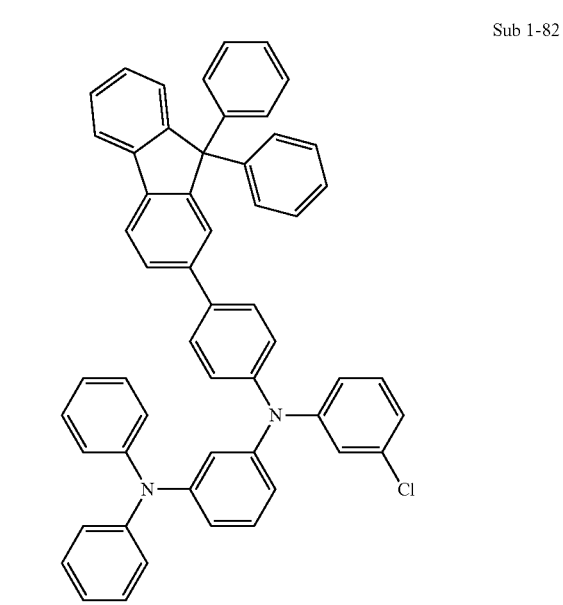

Sub 1-83

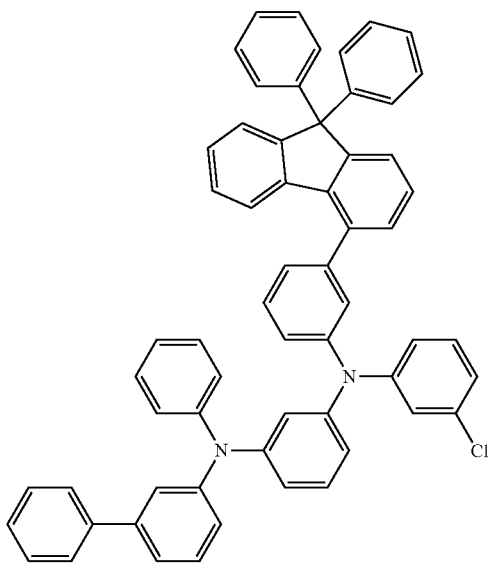

Sub 1-84

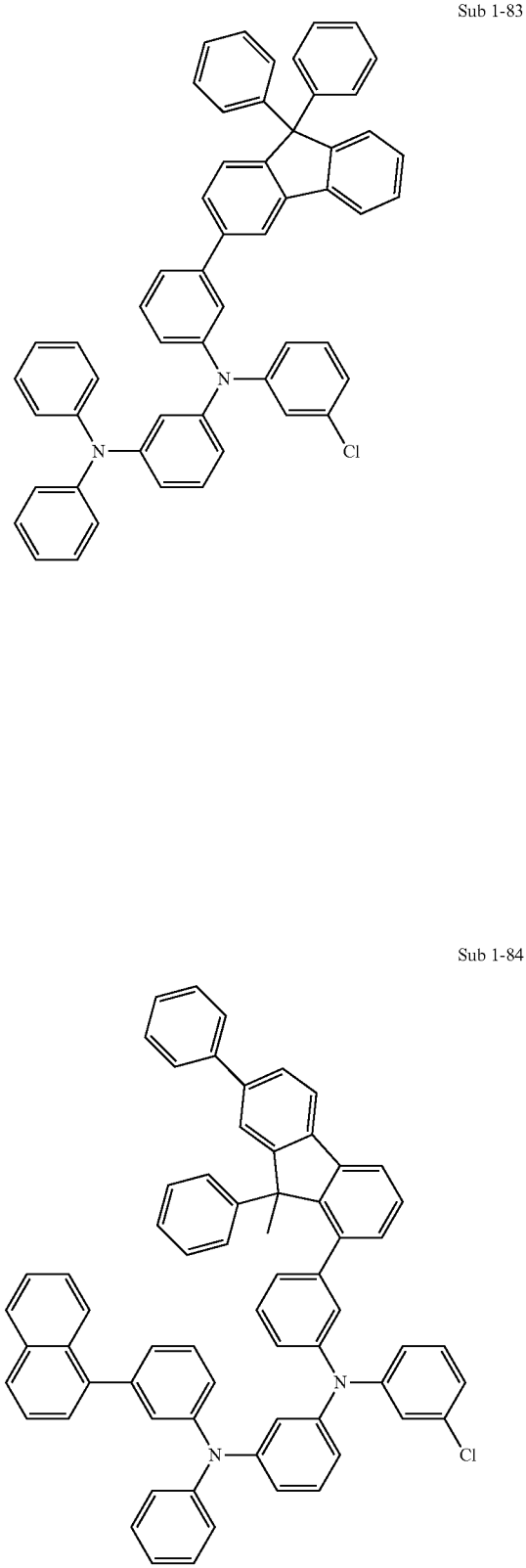

Sub 1-85

TABLE 1

| Compound | FD-MS | Compound | FD-MS |
|---|---|---|---|
| Sub 1-1 | m/z = 684.23 ($C_{49}H_{33}ClN_2$ = 685.27) | Sub 1-2 | m/z = 734.25 ($C_{53}H_{35}ClN_2$ = 735.33) |
| Sub 1-3 | m/z = 760.26 ($C_{55}H_{37}ClN_2$ = 761.37) | Sub 1-4 | m/z = 730.22 ($C_{50}H_{35}ClN_2S$ = 731.35) |
| Sub 1-5 | m/z = 684.23 ($C_{49}H_{33}ClN_2$ = 685.27) | Sub 1-6 | m/z = 784.26 ($C_{57}H_{37}ClN_2$ = 785.39) |
| Sub 1-7 | m/z = 886.31 ($C_{65}H_{43}ClN_2$ = 887.52) | Sub 1-8 | m/z = 734.25 ($C_{53}H_{35}ClN_2$ = 735.33) |
| Sub 1-9 | m/z = 937.32 ($C_{68}H_{44}ClN_3$ = 938.57) | Sub 1-10 | m/z = 1038.37 ($C_{77}H_{51}ClN_2$ = 1039.72) |
| Sub 1-11 | m/z = 829.27 ($C_{38}H_{37}ClFN_3$ = 830.40) | Sub 1-12 | m/z = 684.23 ($C_{49}H_{33}ClN_2$ = 685.27) |
| Sub 1-13 | m/z = 760.26 ($C_{55}H_{37}ClN_2$ = 761.37) | Sub 1-14 | m/z = 788.30 ($C_{57}H_{41}ClN_2$ = 789.42) |
| Sub 1-15 | m/z = 684.23 ($C_{49}H_{33}ClN_2$ = 685.27) | Sub 1-16 | m/z = 842.34 ($C_{61}H_{47}ClN_2$ = 843.51) |
| Sub 1-17 | m/z = 860.30 ($C_{63}H_{41}ClN_2$ = 861.49) | Sub 1-18 | m/z = 684.23 ($C_{49}H_{33}ClN_2$ = 685.27) |
| Sub 1-19 | m/z = 1000.36 ($C_{74}H_{49}ClN_2$ = 1001.67) | Sub 1-20 | m/z = 1048.36 ($C_{78}H_{49}ClN_2$ = 1049.71) |
| Sub 1-21 | m/z = 684.23 ($C_{49}H_{33}ClN_2$ = 685.27) | Sub 1-22 | m/z = 760.26 ($C_{55}H_{37}ClN_2$ = 761.37) |
| Sub 1-23 | m/z = 884.30 ($C_{65}H_{41}ClN_2$ = 885.51) | Sub 1-24 | m/z = 684.23 ($C_{49}H_{33}ClN_2$ = 685.27) |
| Sub 1-25 | m/z = 760.26 ($C_{55}H_{37}ClN_2$ = 761.37) | Sub 1-26 | m/z = 986.34 ($C_{73}H_{47}ClN_2$ = 987.64) |
| Sub 1-27 | m/z = 860.30 ($C_{63}H_{41}ClN_2$ = 861.49) | Sub 1-28 | m/z = 684.23 ($C_{49}H_{33}ClN_2$ = 685.27) |
| Sub 1-29 | m/z = 1008.42 ($C_{74}H_{57}ClN_2$ = 1009.73) | Sub 1-30 | m/z = 930.32 ($C_{67}H_{44}ClFN_2$ = 931.55) |

TABLE 1-continued

| Compound | FD-MS | Compound | FD-MS |
|---|---|---|---|
| Sub 1-31 | m/z = 562.22 ($C_{39}H_{31}ClN_2$ = 563.14) | Sub 1-32 | m/z = 928.36 ($C_{68}H_{49}ClN_2$ = 929.60) |
| Sub 1-33 | m/z = 866.34 ($C_{63}H_{47}ClN_2$ = 867.53) | Sub 1-34 | m/z = 655.22 ($C_{44}H_{31}ClFN_3$ = 656.20) |
| Sub 1-35 | m/z = 562.22 ($C_{39}H_{31}ClN_2$ = 563.14) | Sub 1-36 | m/z = 688.26 ($C_{49}H_{37}ClN_2$ = 689.30) |
| Sub 1-37 | m/z = 714.28 ($C_{51}H_{39}ClN_2$ = 715.34) | Sub 1-38 | m/z = 712.26 ($C_{51}H_{37}ClN_2$ = 713.32) |
| Sub 1-39 | m/z = 562.22 ($C_{39}H_{31}ClN_2$ = 563.14) | Sub 1-40 | m/z = 702.28 ($C_{50}H_{39}ClN_2$ = 703.33) |
| Sub 1-41 | m/z = 640.26 ($C_{45}H_{37}ClN_2$ = 641.26) | Sub 1-42 | m/z = 726.28 ($C_{52}H_{39}ClN_2$ = 727.35) |
| Sub 1-43 | m/z = 562.22 ($C_{39}H_{31}ClN_2$ = 563.14) | Sub 1-44 | m/z = 612.23 ($C_{43}H_{33}ClN_2$ = 613.20) |
| Sub 1-45 | m/z = 638.25 ($C_{45}H_{35}ClN_2$ = 639.24) | Sub 1-46 | m/z = 562.22 ($C_{39}H_{31}ClN_2$ = 563.14) |
| Sub 1-47 | m/z = 638.25 ($C_{45}H_{35}ClN_2$ = 639.24) | Sub 1-48 | m/z = 854.34 ($C_{62}H_{47}ClN_2$ = 855.52) |
| Sub 1-49 | m/z = 914.34 ($C_{67}H_{47}ClN_2$ = 915.58) | Sub 1-50 | m/z = 688.26 ($C_{49}H_{37}ClN_2$ = 689.30) |
| Sub 1-51 | m/z = 754.31 ($C_{54}H_{43}ClN_2$ = 755.40) | Sub 1-52 | m/z = 798.37 ($C_{57}H_{51}ClN_2$ = 799.50) |
| Sub 1-53 | m/z = 562.22 ($C_{39}H_{31}ClN_2$ = 563.14) | Sub 1-54 | m/z = 562.22 ($C_{39}H_{31}ClN_2$ = 563.14) |
| Sub 1-55 | m/z = 612.23 ($C_{43}H_{33}ClN_2$ = 613.20) | Sub 1-56 | m/z = 562.22 ($C_{39}H_{31}ClN_2$ = 563.14) |
| Sub 1-57 | m/z = 612.23 ($C_{43}H_{33}ClN_2$ = 613.20) | Sub 1-58 | m/z = 686.25 ($C_{49}H_{35}ClN_2$ = 687.28) |
| Sub 1-59 | m/z = 638.31 ($C_{61}H_{43}ClN_2$ = 839.48) | Sub 1-50 | m/z = 728.30 ($C_{52}H_{41}ClN_2$ = 729.36) |
| Sub 1-61 | m/z = 722.23 ($C_{49}H_{33}ClF_2N_2$ = 723.26) | Sub 1-62 | m/z = 740.30 ($C_{53}H_{41}ClN_2$ = 741.38) |
| Sub 1-63 | m/z = 812.30 ($C_{59}H_{41}ClN_2$ = 813.44) | Sub 1-64 | m/z = 736.26 ($C_{53}H_{37}ClN_2$ = 737.34) |
| Sub 1-65 | m/z = 736.26 ($C_{53}H_{37}ClN_2$ = 737.34) | Sub 1-66 | m/z = 762.28 ($C_{55}H_{39}ClN_2$ = 763.38) |
| Sub 1-67 | m/z = 686.25 ($C_{49}H_{35}ClN_2$ = 687.28) | Sub 1-68 | m/z = 812.30 ($C_{59}H_{41}ClN_2$ = 813.44) |
| Sub 1-69 | m/z = 838.31 ($C_{61}H_{43}ClN_2$ = 839.48) | Sub 1-70 | m/z = 762.28 ($C_{55}H_{39}ClN_2$ = 763.38) |
| Sub 1-71 | m/z = 926.34 ($C_{68}H_{47}ClN_2$ = 927.59) | Sub 1-72 | m/z = 812.30 ($C_{59}H_{41}ClN_2$ = 813.44) |
| Sub 1-73 | m/z = 862.31 ($C_{63}H_{43}ClN_2$ = 863.50) | Sub 1-74 | m/z = 760.26 ($C_{55}H_{37}ClN_2$ = 761.37) |
| Sub 1-75 | m/z = 760.26 ($C_{55}H_{37}ClN_2$ = 761.37) | Sub 1-76 | m/z = 774.28 ($C_{56}H_{39}ClN_2$ = 775.39) |
| Sub 1-77 | m/z = 936.33 ($C_{69}H_{45}ClN_2$ = 937.58) | Sub 1-78 | m/z = 754.31 ($C_{54}H_{43}ClN_2$ = 755.40) |
| Sub 1-79 | m/z = 694.31 ($C_{49}H_{43}ClN_2$ = 695.35) | Sub 1-80 | m/z = 652.26 ($C_{46}H_{37}ClN_2$ = 653.27) |
| Sub 1-61 | m/z = 770.29 ($C_{54}H_{40}ClFN_2$ = 771.38) | Sub 1-82 | m/z = 762.28 ($C_{55}H_{39}ClN_2$ = 763.38) |
| Sub 1-83 | m/z = 762.28 ($C_{55}H_{39}ClN_2$ = 763.38) | Sub 1-84 | m/z = 902.34 ($C_{66}H_{47}ClN_2$ = 903.57) |
| Sub 1-85 | m/z = 838.31 ($C_{61}H_{43}ClN_2$ = 839.48) | | |

II. Synthesis of Sub 2

Sub 2 in Reaction Scheme 1 was synthesized using the synthesis method disclosed in Korean Patent Number 10-1251451 (issued Apr. 5, 2013) to the present applicant. Sub 2 may be synthesized as illustrated in the following Reaction Scheme 3, with no limitations imparted thereto.

<Reaction Scheme 3>

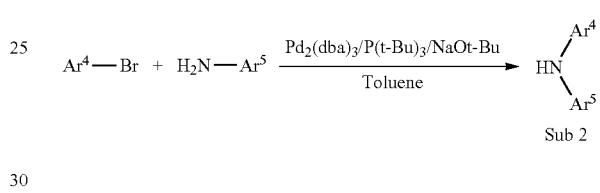

A concrete compound of Sub 2 is synthesized as in the following Synthesis Example:

1. Synthesis Example: Sub 2-1

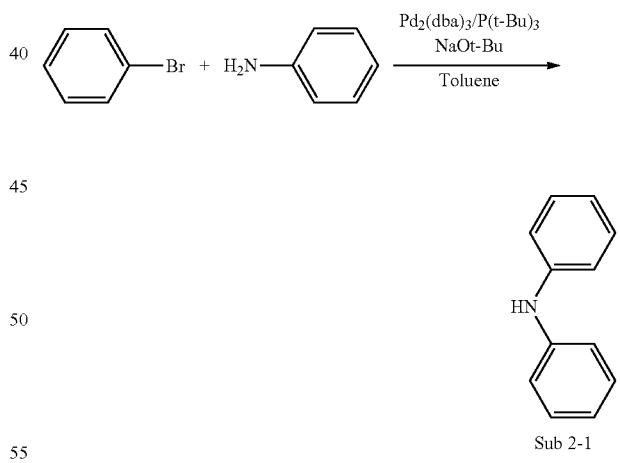

In a round-bottom flask, a solution of bromobenzene (40.7 g, 259.1 mmol) in toluene (1360 ml) was added with aniline (26.5 g, 285 mmol), $Pd_2(dba)_3$ (7.1 g, 7.8 mmol), 50% $P(t-Bu)_3$ (10.1 ml, 20.7 mmol), and NaOt-Bu (74.7 g, 777.3 mmol) and then stirred at 80° C. After completion of the reaction, extraction was performed with $CH_2Cl_2$ and water. The organic layer thus formed was dried over $MgSO_4$ and concentrated. The concentrate was purified by silica gel column chromatography, followed by recrystallization to afford 32.9 g of the product Sub 2-1 (yield: 75%).

2. Synthesis Example: Sub 2-2

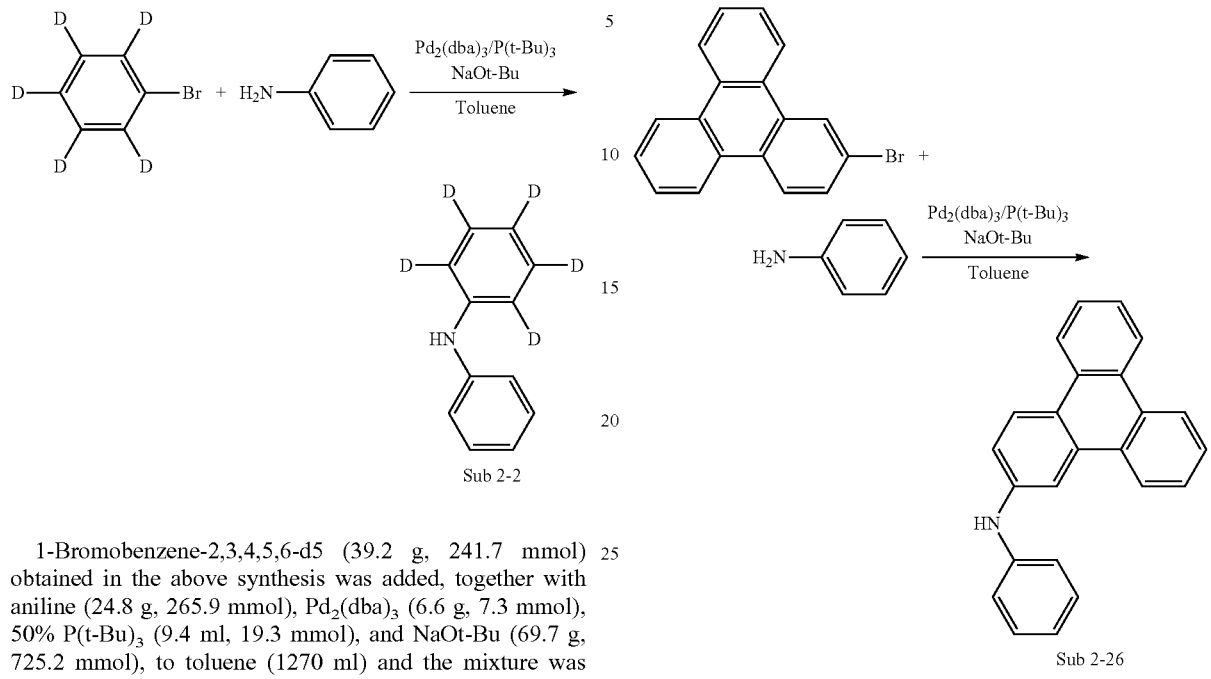

1-Bromobenzene-2,3,4,5,6-d5 (39.2 g, 241.7 mmol) obtained in the above synthesis was added, together with aniline (24.8 g, 265.9 mmol), Pd$_2$(dba)$_3$ (6.6 g, 7.3 mmol), 50% P(t-Bu)$_3$ (9.4 ml, 19.3 mmol), and NaOt-Bu (69.7 g, 725.2 mmol), to toluene (1270 ml) and the mixture was reacted as in the synthesis method for Sub 2-1 to afford 33.3 g of the product Sub 2-2 (yield: 79%).

3. Synthesis Example: Sub 2-10

4-Bromo-1,1'-biphenyl (32.5 g, 139.4 mmol) obtained in the above synthesis was added, together with aniline (14.3 g, 153.4 mmol), Pd$_2$(dba)$_3$ (3.8 g, 4.2 mmol), 50% P(t-Bu)$_3$ (5.4 ml, 11.2 mmol), and NaOt-Bu (40.2 g, 418.3 mmol), to toluene (730 ml) and the mixture was reacted as in the synthesis method for Sub 2-1 to afford 28.4 g of the product Sub 2-10 (yield: 83%).

4. Synthesis Example: Sub 2-26

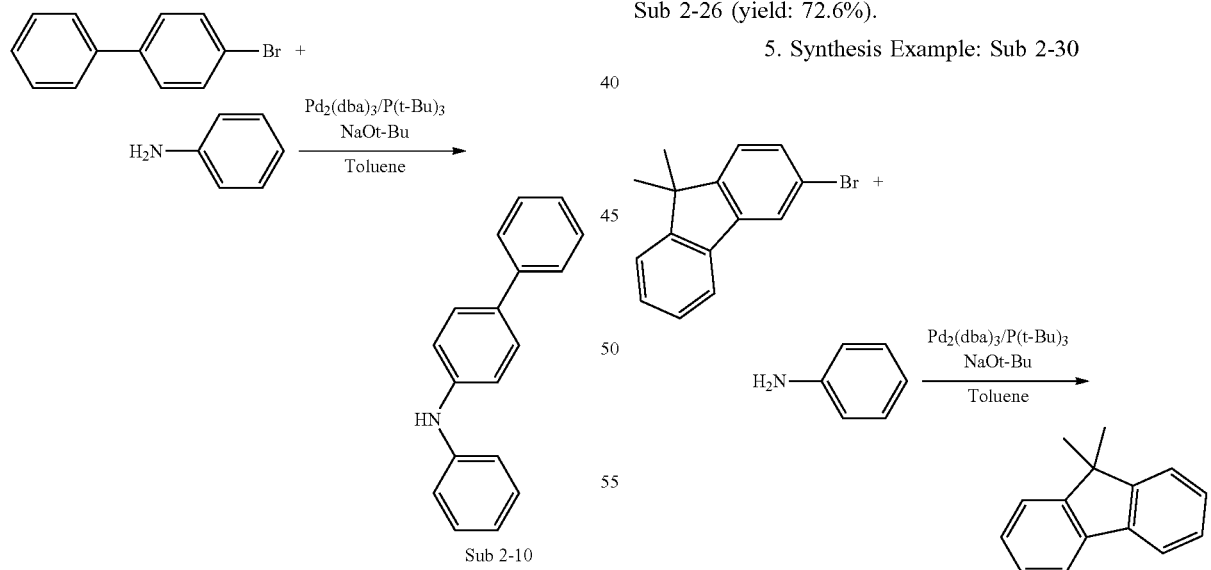

2-Bromotriphenylene (35.7 g, 116.2 mmol) obtained in the above synthesis was added, together with aniline (11.9 g, 127.8 mmol), Pd$_2$(dba)$_3$ (3.2 g, 3.5 mmol), 50% P(t-Bu)$_3$ (4.5 ml, 9.3 mmol), and NaOt-Bu (33.5 g, 348.6 mmol), to toluene (610 ml) and the mixture was reacted as in the synthesis method for Sub 2-1 to afford 27 g of the product Sub 2-26 (yield: 72.6%).

5. Synthesis Example: Sub 2-30

3-Bromo-9,9-dimethyl-9H-fluorene (36.2 g, 132.6 mmol) obtained in the above synthesis was added, together with aniline (13.6 g, 145.9 mmol), Pd$_2$(dba)$_3$ (3.6 g, 4.0 mmol), 50% P(t-Bu)$_3$ (5.2 ml, 10.6 mmol), and NaOt-Bu (38.2 g, 397.9 mmol), to toluene (700 ml) and the mixture was reacted as in the synthesis method for Sub 2-1 to afford 31.8 g of the product Sub 2-26 (yield: 84%).

6. Synthesis Example: Sub 2-33

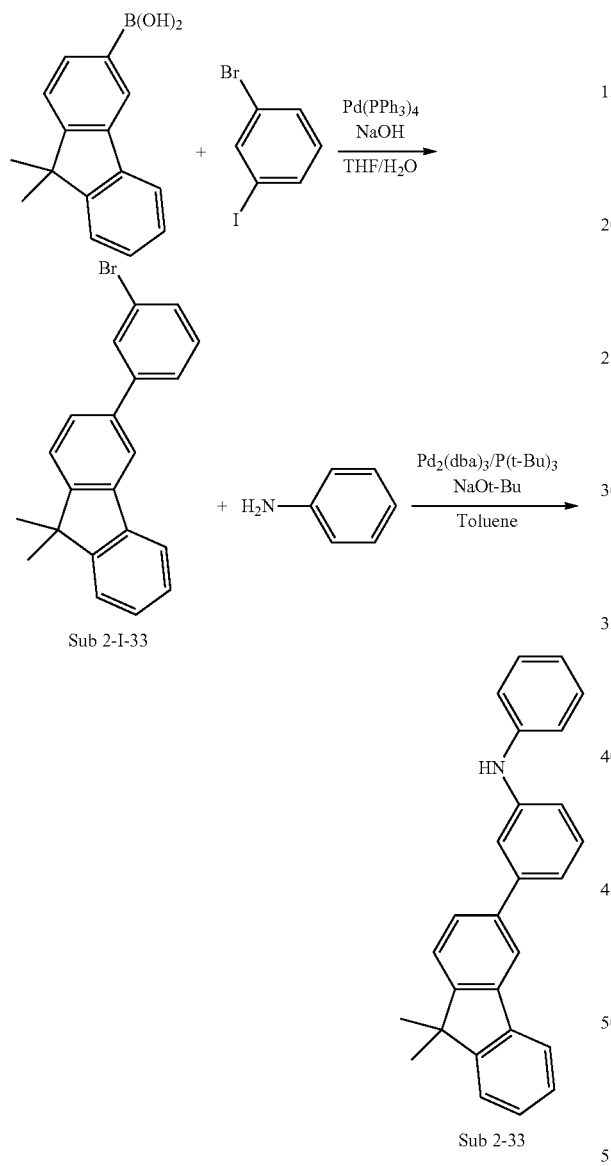

Sub 2-33

(1) Synthesis of Sub 2-I-33

To (9,9-dimethyl-9H-fluoren-3-yl)boronic acid (50 g, 210 mmol) were added 1-bromo-3-iodobenzene (59.4 g, 210 mmol), Pd(PPh3)4 (9.7 g, 8.4 mmol), NaOH (25.2 g, 630 mmol), THF (700 ml), and H2O (350 ml) and the mixture was stirred at 80° C. After completion of the reaction, extraction was performed with CH$_2$Cl$_2$ and water. The organic layer thus formed was dried over MgSO$_4$ and concentrated. The concentrate was purified by silica gel column chromatography, followed by recrystallization to afford 51.6 g of the product Sub 2-I-33 (yield: 70.4%).

(2) Synthesis of Sub 2-33

Sub 2-I-33 (30 g, 85.9 mmol) obtained in the above synthesis was added, together with aniline (8.8 g, 94.5 mmol), Pd$_2$(dba)$_3$ (2.4 g, 2.6 mmol), 50% P(t-Bu)$_3$ (3.3 ml, 6.9 mmol), and NaOt-Bu (24.8 g, 257.7 mmol), to toluene (450 ml) and the mixture was reacted as in the synthesis method for Sub 2-1 to afford 29.4 g of the product Sub 2-33 (yield: 94.7%).

7. Synthesis Example: Sub 2-41

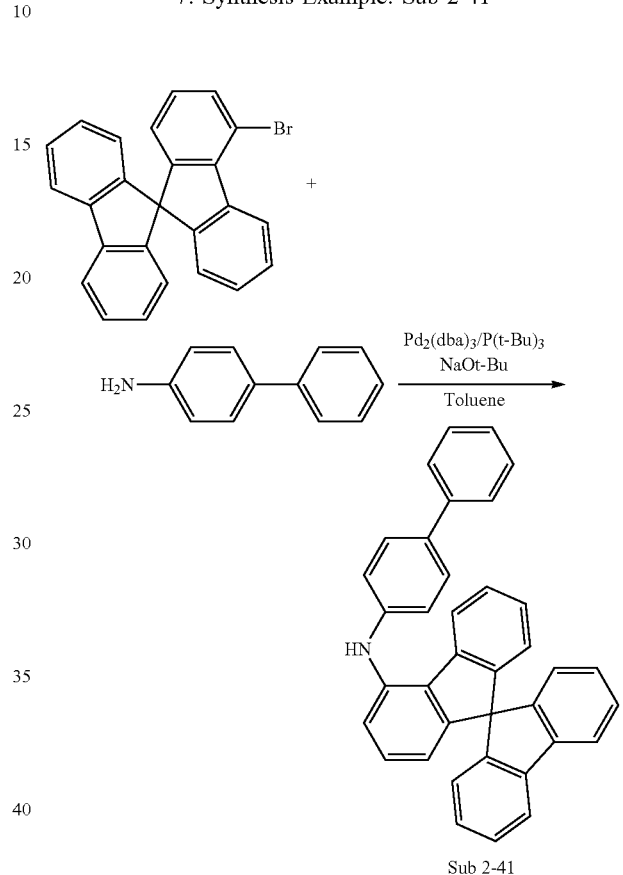

Sub 2-41

4-Bromo-9,9'-spirobi[fluorene] (34.8 g, 88.1 mmol) obtained in the above synthesis was added, together with [1,1'-biphenyl]-4-amine (16.4 g, 97 mmol), Pd$_2$(dba)$_3$ (2.4 g, 2.6 mmol), 50% P(t-Bu)$_3$ (3.4 ml, 7.1 mmol), and NaOt-Bu (25.4 g, 264.4 mmol), to toluene (460 ml) and the mixture was reacted as in the synthesis method for Sub 2-1 to afford 31 g of the product Sub 2-41 (yield: 72.7%).

Meanwhile, examples of Sub 2 include, but are not limited to, the following compounds, and FD-MS (Field Desorption-Mass Spectrometry) values of the compounds of Sub 2 are listed in Table 2, below.

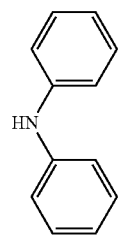

Sub 2-1

-continued
Sub 2-2
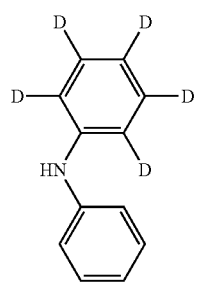
Sub 2-3
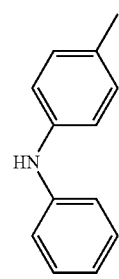
Sub 2-4
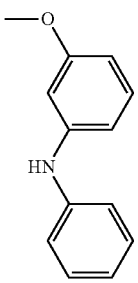
Sub 2-5
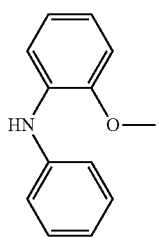
Sub 2-6
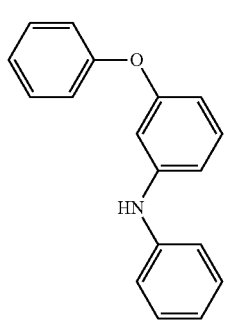
-continued
Sub 2-7
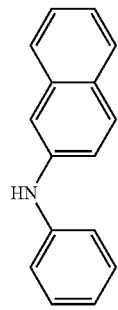
Sub 2-8
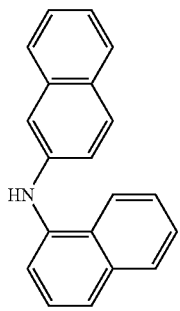
Sub 2-9
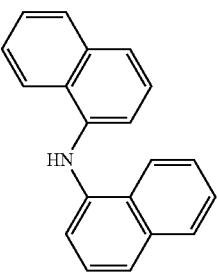
Sub 2-10
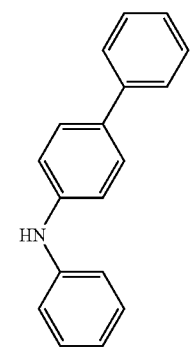
Sub 2-11
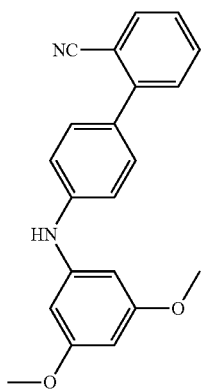

Sub 2-12
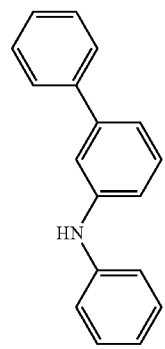
Sub 2-13
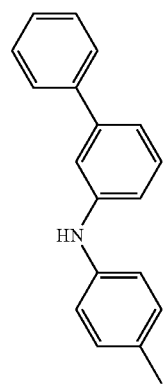
Sub 2-14
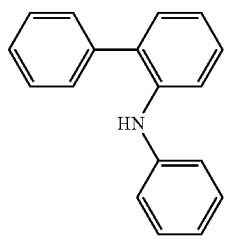
Sub 2-15
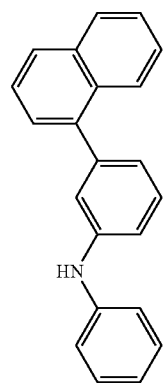
Sub 2-16
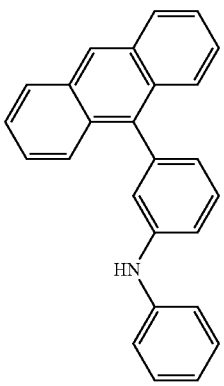
Sub 2-17
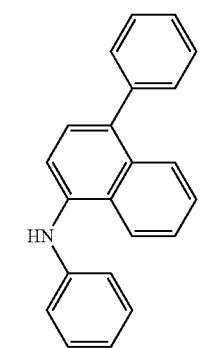
Sub 2-18
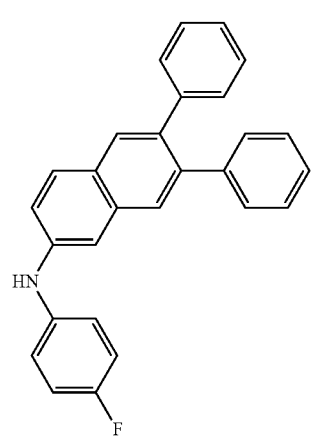
Sub 2-19
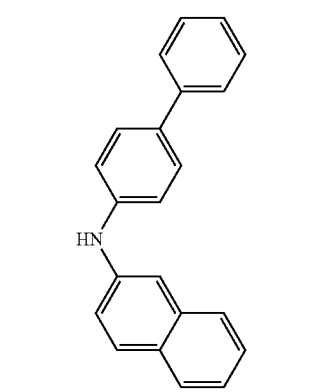

Sub 2-20
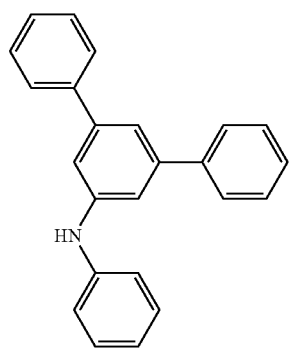
Sub 2-21
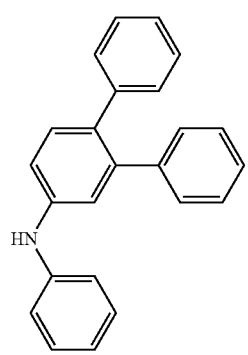
Sub 2-22
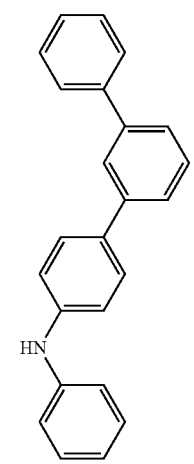
Sub 2-23
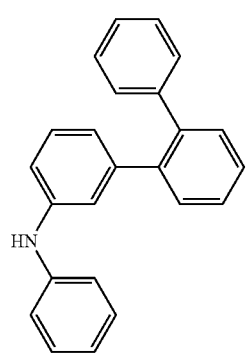
Sub 2-24
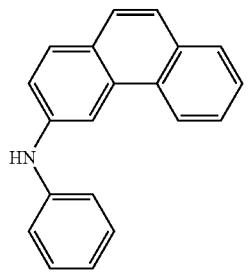
Sub 2-25
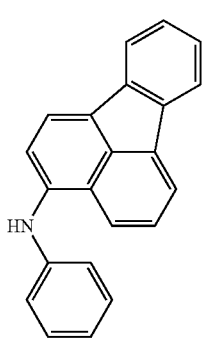
Sub 2-26
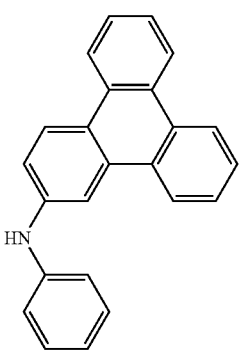
Sub 2-27
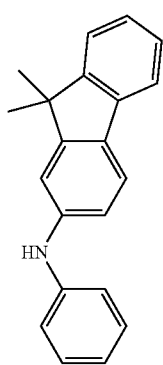

-continued
Sub 2-28
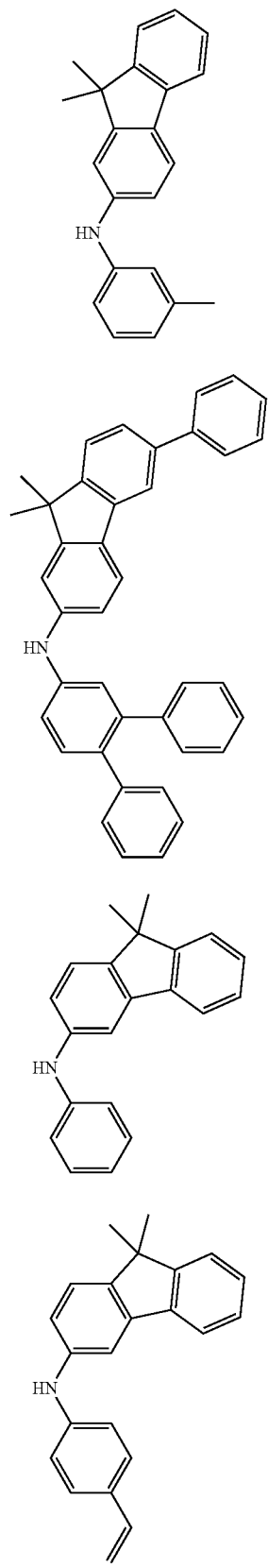
Sub 2-29
Sub 2-30
Sub 2-31
-continued
Sub 2-32
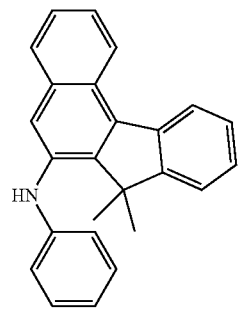
Sub 2-33
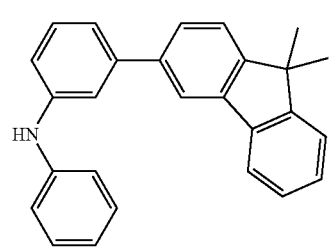
Sub 2-34
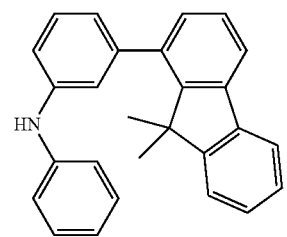
Sub 2-35
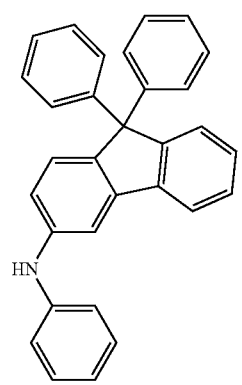

Sub 2-36

Sub 2-37

Sub 2-38

Sub 2-39

Sub 2-40

Sub 2-41

Sub 2-42

Sub 2-43

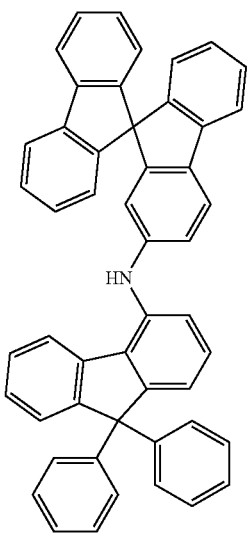

TABLE 2

| Compound | FD-MS | Compound | FD-MS |
|---|---|---|---|
| Sub 2-1 | m/z = 169.09 ($C_{12}H_{11}N$ = 169.23) | Sub 2-2 | m/z = 174.12 ($C_{12}H_6D_5N$ = 174.26) |
| Sub 2-10 | m/z = 245.12 ($C_{18}H_{15}N$ = 245.33) | Sub 2-12 | m/z = 245.12 ($C_{18}H_{15}N$ = 245.33) |
| Sub 2-26 | m/z = 319.14 ($C_{24}H_{17}N$ = 319.41) | Sub 2-30 | m/z = 285.15 ($C_{21}H_{19}N$ = 285.39) |
| Sub 2-32 | m/z = 335.17 ($C_{25}H_{21}N$ = 335.45) | Sub 2-33 | m/z = 361.18 ($C_{27}H_{23}N$ = 361.49) |
| Sub 2-41 | m/z = 483.20 ($C_{37}H_{25}N$ = 483.61) | Sub 2-43 | m/z = 647.26 ($C_{50}H_{33}N$ = 647.82) |

III. Product Synthesis

In a round-bottom flask, a solution of Sub1 (1 equivalent) in toluene was stirred together with Sub2 (1 equivalent), Pd$_2$(dba)$_3$ (0.03 equivalents), (t-Bu)3P (0.06 equivalents), and NaOt-Bu (3 equivalents) at 135° C. for 3 hours. After completion of the reaction, extraction was performed with CH$_2$Cl$_2$ and water. The organic layer thus formed was dried over MgSO$_4$ and concentrated. The concentrate was purified by silica gel column chromatography, followed by recrystallization to afford the final product.

1. Synthesis Example: P-7

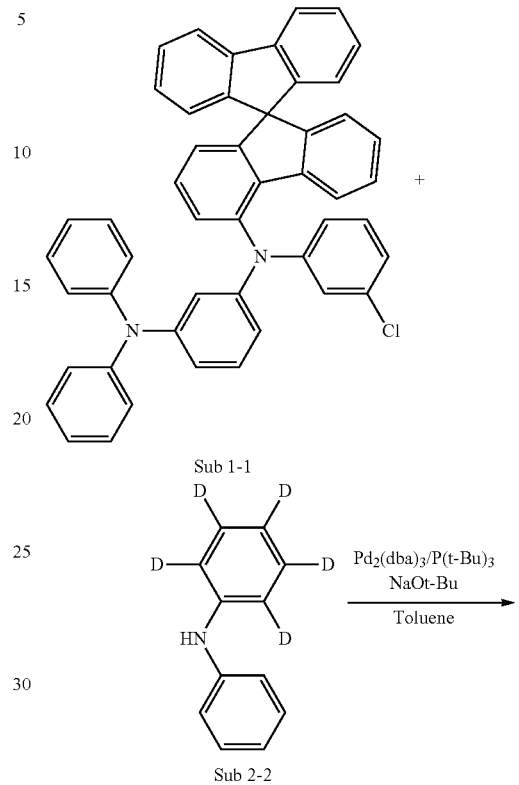

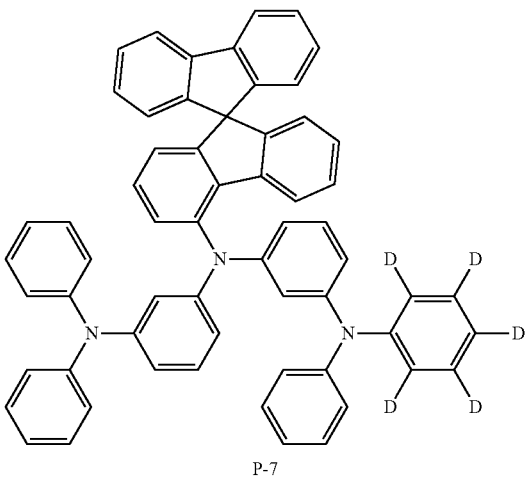

P-7

In a round-bottom flask, a solution of Sub 1-1 (20 g, 29.1 mmol) obtained in the above synthesis in toluene (100 ml) was added with Sub 2-2 (5.1 g, 29.1 mmol), Pd$_2$(dba)$_3$ (0.8 g, 0.87 mmol), 50% P(t-Bu)$_3$ (0.9 ml, 1.7 mmol), and NaOt-Bu (8.4 g, 87.5 mmol) and then stirred at 130° C. After completion of the reaction, extraction was performed with CH$_2$Cl$_2$ and water. The organic layer thus formed was dried over MgSO$_4$ and concentrated. The concentrate was purified by silica gel column chromatography, followed by recrystallization to afford 20 g of the product P-7 (yield: 83.3%).

2. Synthesis Example: P-8

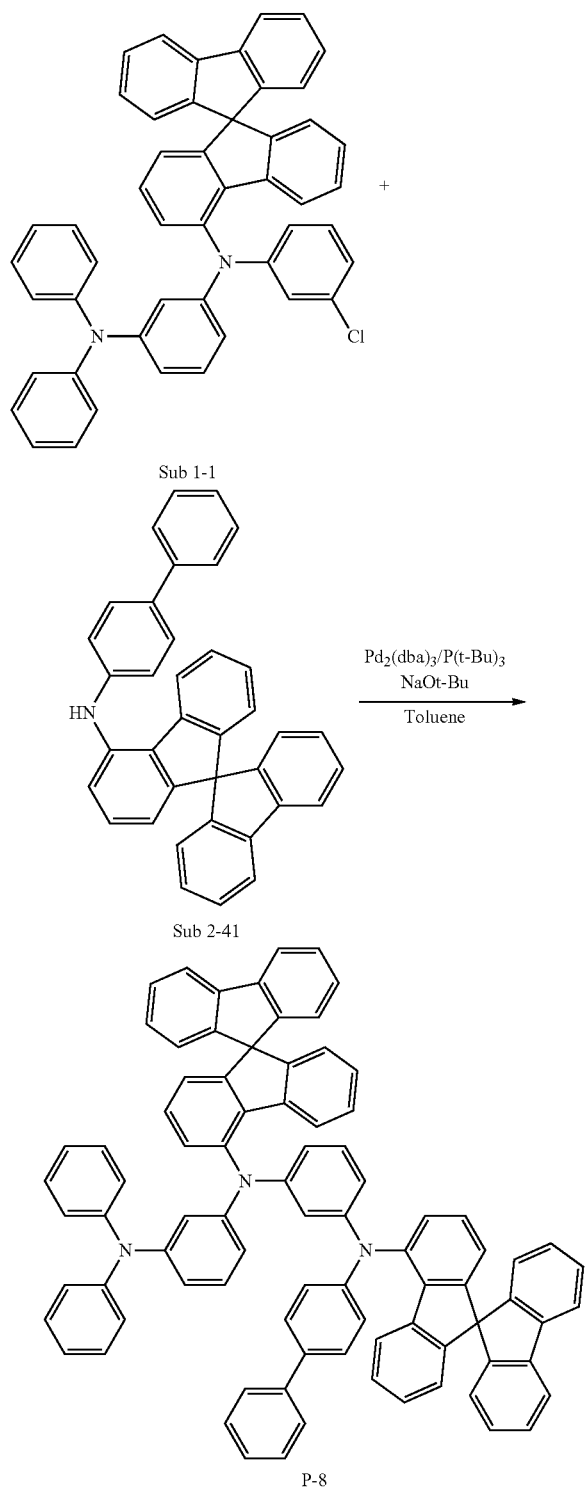

3. Synthesis Example: P-16

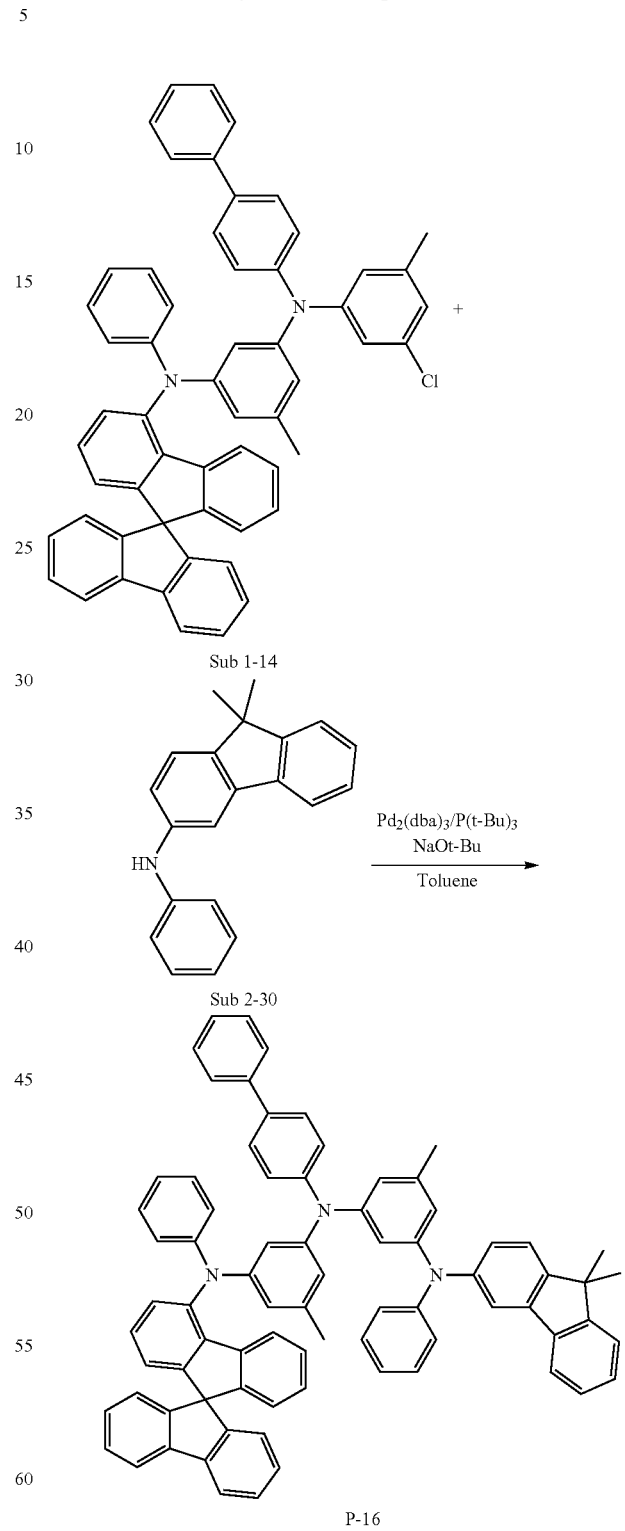

Sub 1-1 (20 g, 29.1 mmol) obtained in the above synthesis was added, together with Sub 2-41 (14.1 g, 29.1 mmol), Pd$_2$(dba)$_3$ (0.8 g, 0.87 mmol), 50% P(t-Bu)$_3$ (0.9 ml, 1.7 mmol), and NaOt-Bu (8.4 g, 87.5 mmol), to toluene (100 ml) and the mixture was reacted as in the synthesis method for P-7 to afford 28 g of the product P-8 (yield: 84.8%).

Sub 1-14 (10 g, 12.6 mmol) obtained in the above synthesis was added, together with Sub 2-30 (3.6 g, 12.6 mmol), Pd$_2$ (dba)$_3$ (0.35 g, 0.38 mmol), 50% P (t-Bu)$_3$ (0.4 ml, 0.76 mmol), and NaOt-Bu (3.6 g, 38 mmol), to toluene (42 ml) and the mixture was reacted as in the synthesis method for P-7 to afford 11 g of the product P-16 (yield: 83.6%).

4. Synthesis Example: P-59

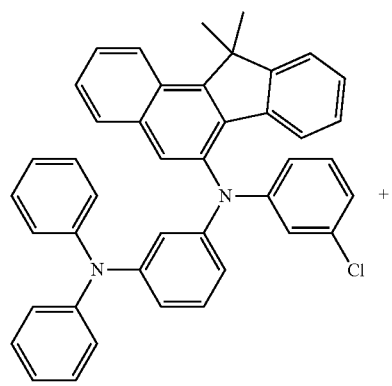
Sub 1-44

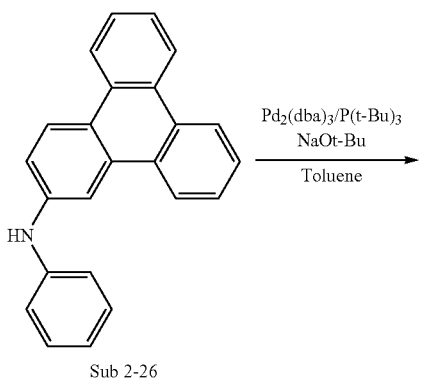
Sub 2-26

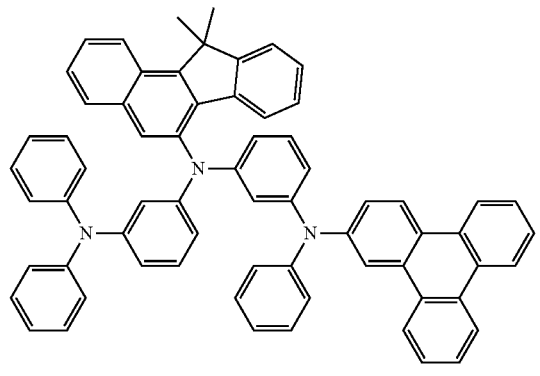
P-59

Sub 1-44 (20 g, 32.6 mmol) obtained in the above synthesis was added, together with Sub 2-26 (10.4 g, 32.6 mmol), Pd$_2$(dba)$_3$ (0.89 g, 0.97 mmol), 50% P(t-Bu)$_3$ (1.0 ml, 1.95 mmol), and NaOt-Bu (9.4 g, 97.8 mmol), to toluene (108 ml) and the mixture was reacted as in the synthesis method for P-7 to afford 21 g of the product P-59 (yield: 71.8%).

5. Synthesis Example: P-63

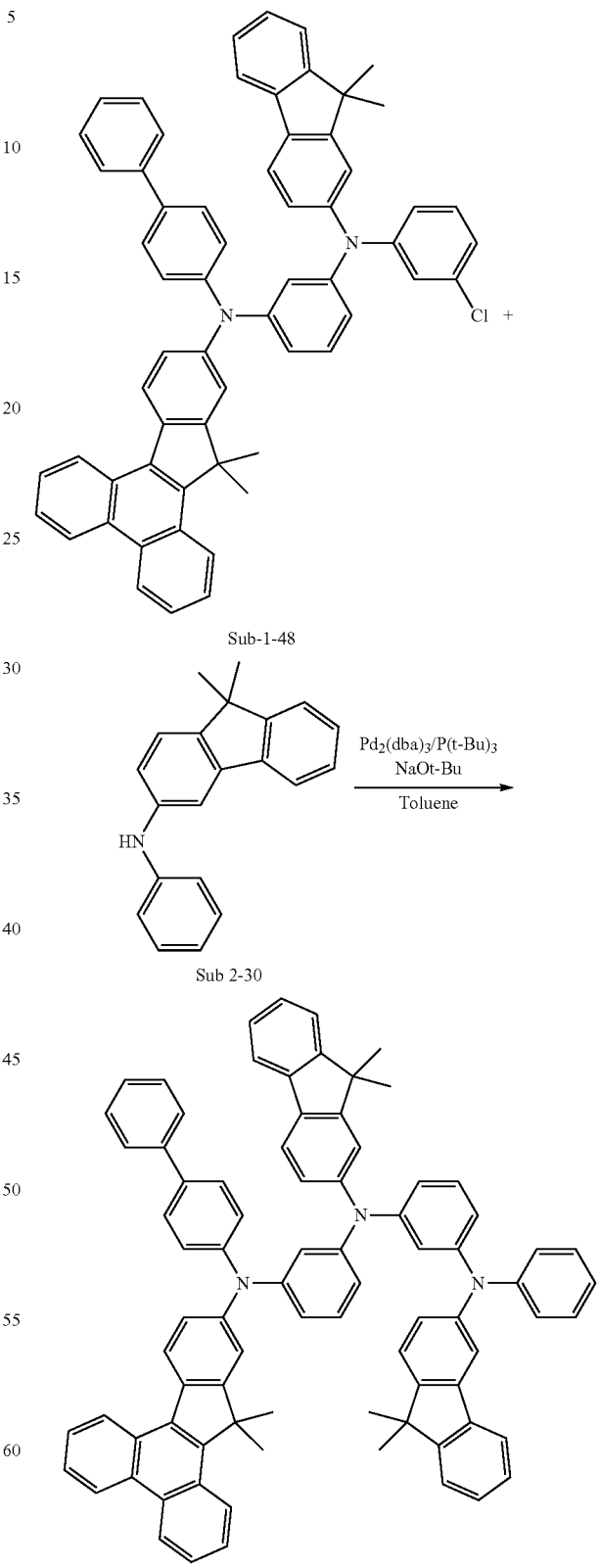

Sub 1-48 (30 g, 35 mmol) obtained in the above synthesis was added, together with Sub 2-30 (10 g, 35 mmol), Pd₂(dba)₃ (1 g, 1.05 mmol), 50% P(t-Bu)₃ (1.0 ml, 2.1 mmol), and NaOt-Bu (10 g, 105 mmol), to toluene (116 ml) and the mixture was reacted as in the synthesis method for P-7 to afford 38 g of the product P-63 (yield: 98.1%).

mmol), Pd₂(dba)₃ (1.1 g, 1.3 mmol), 50% P(t-Bu)₃ (1.3 ml, 2.6 mmol), and NaOt-Bu (12.6 g, 130 mmol), to toluene (145 ml) and the mixture was reacted as in the synthesis method for P-7 to afford 40 g of the product P-85 (yield: 90.5%).

6. Synthesis Example: P-85

7. Synthesis Example: P-94

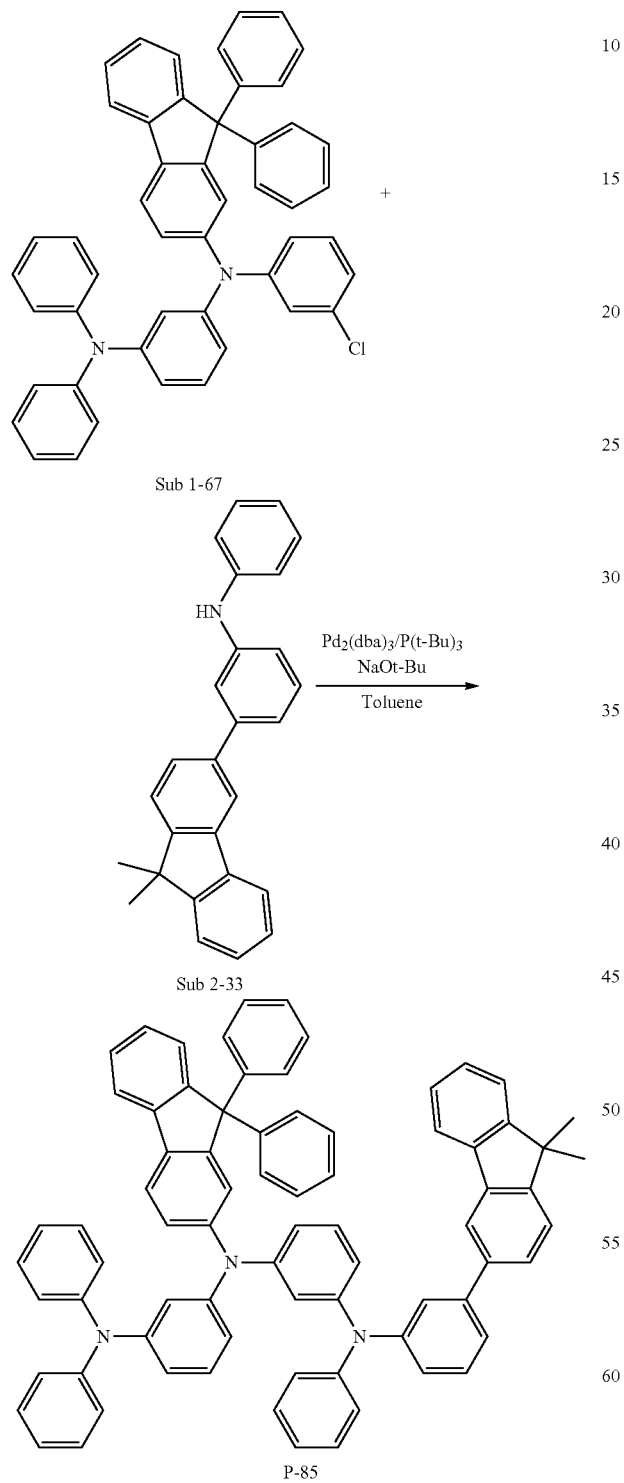

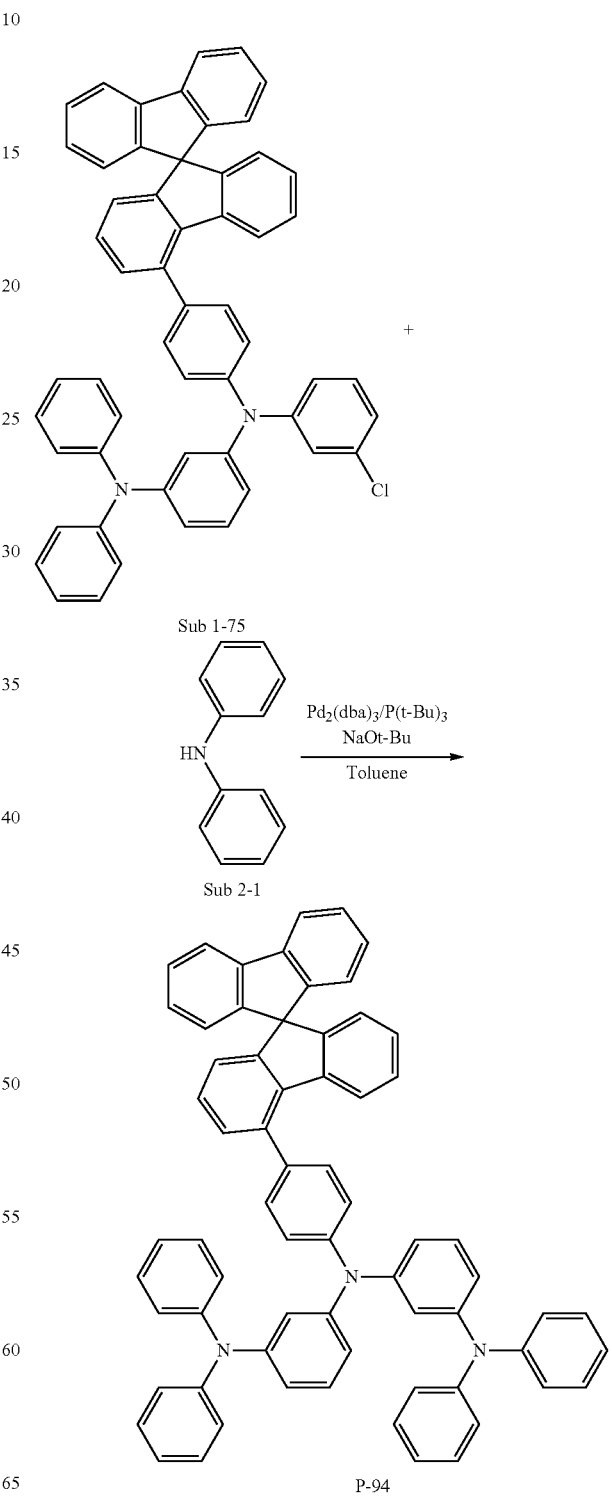

Sub 1-67 (30 g, 43.6 mmol) obtained in the above synthesis was added, together with Sub 2-33 (15.8 g, 43.6

Sub 1-75 (27 g, 35.4 mmol) obtained in the above synthesis was added, together with Sub 2-1 (6 g, 35.4 mmol), Pd$_2$(dba)$_3$ (0.97 g, 1.1 mmol), 50% P(t-Bu)$_3$ (1.0 ml, 2.1 mmol), and NaOt-Bu (10 g, 106 mmol), to toluene (118 ml) and the mixture was reacted as in the synthesis method for P-7 to afford 30 g of the product P-94 (yield: 94.6%).

The compounds P-1 to P-104 of the present disclosure synthesized according to the Synthesis Examples were measured to have FD-MS values listed in Table 3, below.

TABLE 3

| Compound | FD-MS | Compound | FD-MS |
|---|---|---|---|
| P-1 | m/z = 817.35 (C$_{61}$H$_{43}$N$_3$ = 818.04) | P-4 | m/z = 893.38 (C$_{67}$H$_{47}$N$_3$ = 894.13) |
| P-7 | m/z = 822.38 (C$_{61}$H$_{38}$D$_5$N$_3$ = 823.07) | P-8 | m/z = 1131.46 (C$_{86}$H$_{57}$N$_3$ = 1132.42) |
| P-15 | m/z = 893.38 (C$_{67}$H$_{47}$N$_3$ = 894.13) | P-16 | m/z = 1037.47 (C$_{78}$H$_{59}$N$_3$ = 1038.35) |
| P-18 | m/z = 817.35 (C$_{61}$H$_{43}$N$_3$ = 818.04) | P-41 | m/z = 695.33 (C$_{51}$H$_{41}$N$_3$ = 695.91) |
| P-43 | m/z = 771.36 (C$_{57}$H$_{45}$N$_3$ = 772.01) | P-45 | m/z = 811.39 (C$_{60}$H$_{49}$N$_3$ = 812.07) |
| P-59 | m/z = 895.39 (C$_{67}$H$_{49}$N$_3$ = 896.15) | P-62 | m/z = 771.36 (C$_{57}$H$_{45}$N$_3$ = 772.01) |
| P-63 | m/z = 1103.52 (C$_{83}$H$_{65}$N$_3$ = 1104.45) | P-73 | m/z = 819.36 (C$_{61}$H$_{45}$N$_3$ = 820.05) |
| P-85 | m/z = 1011.46 (C$_{76}$H$_{57}$N$_3$ = 1012.31) | P-94 | m/z = 893.38 (C$_{67}$H$_{47}$N$_3$ = 894.13) |
| P-97 | m/z = 887.42 (C$_{66}$H$_{53}$N$_3$ = 888.17) | P-104 | m/z = 1047.46 (C$_{79}$H$_{57}$N$_3$ = 1048.35) |

As described above, synthesis of the compounds represented by Chemical Formula 1 was explained in exemplary synthesis examples. However, because the synthesis of all the compounds is based on the Buchwald-Hartwig cross coupling reaction, it should be readily understood to a person skilled in the art that the reaction can be proceeded even if substituents defined in Chemical Formula 1 (X, Ar$^1$ to Ar$^5$, L, R$^1$ to R$^4$, m, n, o, and p) other than the substituents given in the Synthesis Examples are bound to the core framework. For example, the Sub 1→final product reaction in Reaction Scheme 1, and the starting material→Sub 1-I reaction, the Sub 1-I→Sub 1-II reaction, and the Sub 1-II-→Sub 1 reaction in Reaction Scheme 2 are all based on the Buchwald-Hartwig cross coupling reaction. These reactions might proceed even though unspecified substituents are bound to the framework.

For materials used as starting materials, the following synthesis methods were employed.

The compound of Chemical Formula 1-1 wherein the linker L was a halogen was synthesized using the synthesis methods disclosed in Korean Patent Numbers 10-1520955 (issued May 11, 2015), 10-1530885 (issued Jun. 17, 2015), 10-1530886 (Jun. 17, 2015), and 10-1614740 (issued Apr. 18, 2016), Korean Patent Application Numbers 2013-0056221 (filed May 20, 2013), 2015-0035780 (filed Mar. 16, 2015), and 2015-0083505 (filed Jun. 12, 2015), all issued to the present applicant. In the case where the linker L of Chemical Formula 1-1 was NH2, the compound was synthesized by the Copper-mediated amination reaction (Org. Lett. 2014, 16, 2114) from the synthesized halogen substituent.

Evaluation for Fabrication of Organic Electric Element

[Example 1] Blue Organic Electroluminescent Diode (Auxiliary Light-Emitting Layer)

An organic electroluminescent diode was fabricated by a typical method using the compound of the present disclosure as a material for an auxiliary light-emitting layer. First, 4,4',4"-Tris[2-naphthyl(phenyl)amino]triphenylamine (hereinafter, abbreviated as "2-TNATA") was vacuum deposited on an ITO layer (anode) formed on a glass substrate to form a hole injection layer 60 nm thick which was then overlaid with NPB by vacuum deposition to form a hole transport layer 60 nm thick. Subsequently, the compound P-1 of the present disclosure was vacuum deposited to a thickness of 20 nm on the hole transport layer to form an auxiliary light-emitting layer which was then covered with a mixture of 9,10-di(naphthalen-2-yl)anthracene as a host and BD-052X (Idemitsu kosan) as a dopant at a weight ratio of 96:4 by vacuum deposition to form a 30-nm-thick light-emitting layer. On the light-emitting layer, (1,1'-biphenyl)-4-oleito)bis(2-methyl-8-quinolinoleito)aluminum (hereinafter, abbreviated as "BAlq") was vacuum deposited to form a 10-nm-thick hole blocking layer which was then overlaid with tris(8-quinolinol) aluminum (hereinafter abbreviated as Alq$_3$) by vacuum deposition to form an electron transport layer 40 nm thick, on which an electron injection layer of the alkaline metal halide LiF was deposited at a thickness of 0.2 nm and then covered with a 150-nm-thick Al layer as a cathode to fabricate an organic electroluminescent diode.

[Examples 2 to 40] Blue Organic Electroluminescent Diodes (Auxiliary Light-Emitting Layer)

Organic electroluminescent diodes were fabricated in the same manner as in Example 1, with the exception of using, instead of the compound P-1 of the present disclosure, the compounds P-2 to P-94 of the present disclosure, listed in Table 4, below.

[Comparative Example 1] Blue Organic Electroluminescent Diode (Auxiliary Light-Emitting Layer)

An organic electroluminescent diode was fabricated in the same manner as in Example 1, with the exception that the auxiliary light-emitting layer was not formed.

[Comparative Examples 2 AND 3] Blue Organic Electroluminescent Diodes (Auxiliary Light-Emitting Layer)

Organic electroluminescent diodes were fabricated in the same manner as in Example 1, with the exception of using, instead of the compound P-1 of the present disclosure, the following comparative compound 1 or 2, listed in Table 4, below.

<Comparative Compound 1>

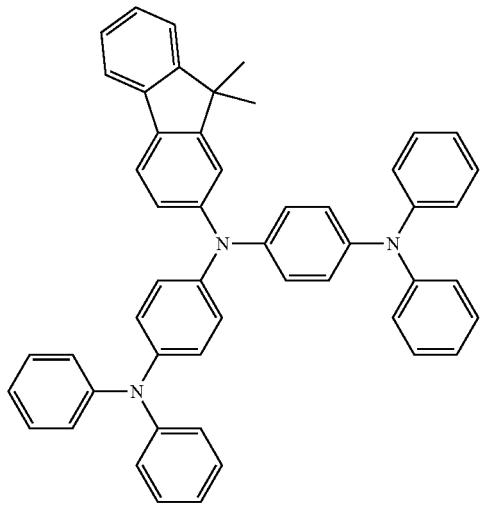 [SMILES: CC1(C)c2ccccc2-c2ccc(N(c3ccc(N(c4ccccc4)c4ccccc4)cc3)c3ccc(N(c4ccccc4)c4ccccc4)cc3)cc21]

<Comparative Compound 2>

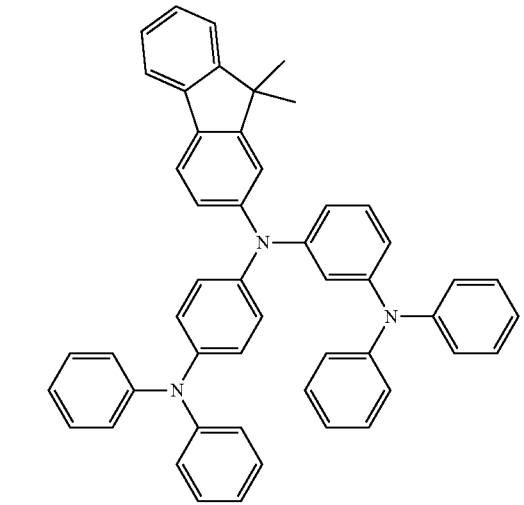 [SMILES: CC1(C)c2ccccc2-c2ccc(N(c3ccc(N(c4ccccc4)c4ccccc4)cc3)c3cccc(N(c4ccccc4)c4ccccc4)c3)cc21]

The organic electroluminescent diodes fabricated in Examples 1 to 40 and Comparative Examples 1 to 3 were measured for electroluminescence properties by PR-650 of Photo Research Inc. while a forward bias DC voltage was applied thereto. T95 lifetime was measured at the reference brightness of 500 cd/m$^2$, using a lifetime tester from McScience Inc. The measurements are listed in Table 4, below.

TABLE 4

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| Comparative Example(1) | — | 5.7 | 13.5 | 500 | 3.7 | 63.0 | 0.15 | 0.12 |
| Comparative Example(2) | Comparative Compound 1 | 5.9 | 12.5 | 500 | 4.0 | 77.4 | 0.14 | 0.12 |
| Comparative Example(3) | Comparative Compound2 | 5.7 | 11.6 | 500 | 4.3 | 83.6 | 0.14 | 0.12 |
| Example(1) | Compound(P-1) | 5.3 | 6.2 | 500 | 8.0 | 144.8 | 0.14 | 0.12 |
| Example(2) | Compound(P-2) | 5.3 | 6.4 | 500 | 7.9 | 141.8 | 0.14 | 0.11 |
| Example(3) | Compound(P-3) | 5.4 | 6.4 | 500 | 7.9 | 138.6 | 0.14 | 0.12 |
| Example(4) | Compound(P-4) | 5.3 | 6.2 | 500 | 8.1 | 145.7 | 0.14 | 0.11 |
| Example(5) | Compound(P-5) | 5.3 | 6.4 | 500 | 7.9 | 139.4 | 0.14 | 0.11 |
| Example(6) | Compound(P-6) | 5.4 | 6.7 | 500 | 7.5 | 134.8 | 0.14 | 0.11 |
| Example(7) | Compound(P-7) | 5.4 | 6.5 | 500 | 7.7 | 138.0 | 0.14 | 0.11 |
| Example(8) | Compound(P-9) | 5.3 | 6.6 | 500 | 7.6 | 136.0 | 0.14 | 0.12 |
| Example(9) | Compound(P-14) | 5.3 | 7.0 | 500 | 7.1 | 132.3 | 0.14 | 0.11 |
| Example(10) | Compound(P-15) | 5.3 | 6.9 | 500 | 7.2 | 130.2 | 0.14 | 0.11 |
| Example(11) | Compound(P-18) | 5.3 | 7.0 | 500 | 7.1 | 131.0 | 0.14 | 0.12 |
| Example(12) | Compound(P-19) | 5.4 | 7.2 | 500 | 6.9 | 127.3 | 0.14 | 0.12 |
| Example(13) | Compound(P-21) | 5.4 | 7.5 | 500 | 6.7 | 129.1 | 0.14 | 0.12 |
| Example(14) | Compound(P-25) | 5.4 | 6.9 | 500 | 7.2 | 123.6 | 0.14 | 0.11 |
| Example(15) | Compound(P-26) | 5.3 | 7.0 | 500 | 7.2 | 124.4 | 0.14 | 0.12 |
| Example(16) | Compound(P-29) | 5.5 | 7.5 | 500 | 6.6 | 120.3 | 0.14 | 0.11 |
| Example(17) | Compound(P-33) | 5.5 | 8.0 | 500 | 6.3 | 119.5 | 0.14 | 0.12 |
| Example(18) | Compound(P-37) | 5.4 | 8.3 | 500 | 6.0 | 117.0 | 0.14 | 0.11 |
| Example(19) | Compound(P-41) | 5.5 | 8.6 | 500 | 5.8 | 112.0 | 0.14 | 0.12 |
| Example(20) | Compound(P-42) | 5.5 | 8.8 | 500 | 5.7 | 108.9 | 0.14 | 0.12 |
| Example(21) | Compound(P-43) | 5.5 | 8.7 | 500 | 5.8 | 112.0 | 0.14 | 0.12 |
| Example(22) | Compound(P-44) | 5.5 | 9.1 | 500 | 5.5 | 104.8 | 0.14 | 0.12 |
| Example(23) | Compound(P-45) | 5.5 | 9.2 | 500 | 5.4 | 106.7 | 0.14 | 0.12 |
| Example(24) | Compound(P-49) | 5.5 | 8.7 | 500 | 5.7 | 112.6 | 0.14 | 0.12 |
| Example(25) | Compound(P-50) | 5.4 | 9.4 | 500 | 5.3 | 111.2 | 0.14 | 0.12 |
| Example(26) | Compound(P-53) | 5.6 | 9.4 | 500 | 5.3 | 100.4 | 0.14 | 0.12 |
| Example(27) | Compound(P-57) | 5.4 | 8.0 | 500 | 6.2 | 118.6 | 0.14 | 0.11 |
| Example(28) | Compound(P-59) | 5.4 | 8.9 | 500 | 5.6 | 112.8 | 0.14 | 0.11 |
| Example(29) | Compound(P-60) | 5.5 | 8.2 | 500 | 6.1 | 117.4 | 0.14 | 0.11 |
| Example(30) | Compound(P-61) | 5.5 | 9.2 | 500 | 5.4 | 111.5 | 0.14 | 0.12 |
| Example(31) | Compound(P-62) | 5.5 | 9.2 | 500 | 5.4 | 108.5 | 0.14 | 0.11 |

TABLE 4-continued

| | Compound | Voltage (V) | Current Density (mA/cm2) | Brightness (cd/m2) | Efficiency (cd/A) | Lifetime T(95) | CIE x | CIE y |
|---|---|---|---|---|---|---|---|---|
| Example(32) | Compound(P-68) | 5.4 | 9.2 | 500 | 5.4 | 112.0 | 0.14 | 0.11 |
| Example(33) | Compound(P-69) | 5.5 | 9.8 | 500 | 5.1 | 101.2 | 0.14 | 0.12 |
| Example(34) | Compound(P-71) | 5.4 | 8.8 | 500 | 5.7 | 113.2 | 0.14 | 0.11 |
| Example(35) | Compound(P-72) | 5.5 | 8.8 | 500 | 5.7 | 113.8 | 0.14 | 0.12 |
| Example(36) | Compound(P-73) | 5.6 | 9.6 | 500 | 5.2 | 102.8 | 0.14 | 0.11 |
| Example(37) | Compound(P-82) | 5.6 | 9.9 | 500 | 5.1 | 101.1 | 0.14 | 0.12 |
| Example(38) | Compound(P-84) | 5.5 | 9.5 | 500 | 5.2 | 100.3 | 0.14 | 0.12 |
| Example(39) | Compound(P-89) | 5.4 | 9.4 | 500 | 5.3 | 110.1 | 0.14 | 0.11 |
| Example(40) | Compound(P-94) | 5.6 | 9.8 | 500 | 5.1 | 103.2 | 0.14 | 0.12 |

As is understood from the data of Table 4, the blue organic electroluminescent diodes fabricated using the materials of the present disclosure as auxiliary light-emitting layer materials in organic electroluminescent diodes were found to operate at lower driving voltages and significantly improve in emission efficiency and lifespan, compared to those fabricated in the Comparative Examples where no auxiliary light-emitting layers were formed or the comparative compound 1 or 2 was used.

In addition, different results were obtained according to the positions at which the amine moieties are bonded to the linker phenyl groups.

of holes to the light-emitting layer and in the ability to block electrons, increasing the emission efficiency and the lifespan.

Particularly, the compound in which spirofluorene is located at position 4 has a far deeper HOMO energy level and allows more holes to easily and rapidly migrate to the light-emitting layer than any of the other compounds of the present disclosure, thus increasing a charge balance between holes and electrons in the light-emitting layer and bringing about the highest improvement in driving voltage, emission efficiency, and lifespan.

TABLE 5

| Compound | Comparative Compound 1 | Comparative Compound 2 | Inventive Compound P-41 |
|---|---|---|---|
| Structure | 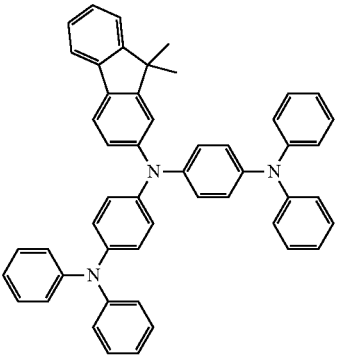 | 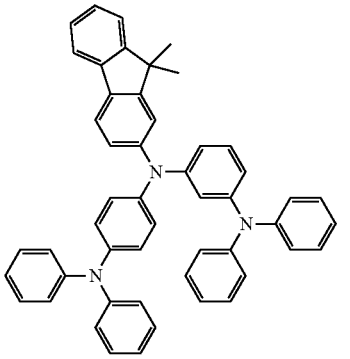 | 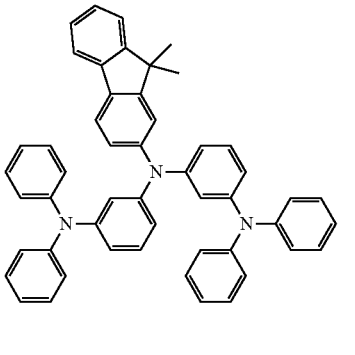 |
| HOMO (eV) | 4.4706 | 4.5312 | 4.7797 |
| LUMO (eV) | 0.8421 | 0.8314 | 0.8106 |
| Eg (eV) | 3.6285 | 3.6998 | 3.9691 |
| T1(eV) | 2.694 | 2.747 | 2.911 |

Better properties were detected in the comparative compound 2 in which one of the amine moieties is bonded at the meta position to one of the linker phenyl groups than the comparative compound 1 in which both of the amine moieties are bonded at the para positions to the respective linker phenyl groups. The compounds of the present disclosure in which both of the amine moieties are bonded at the meta positions to the respective linker phenyl groups were observed to far further improve in driving voltage, emission efficiency, and lifespan than the comparative compounds. In our opinion, these results are attributed to the fact that deeper HOMO energy levels and higher T1 values are generated with the bonding of more amine moieties at the meta positions on the linker phenyl group, whereby an improvement can be brought about in the smooth transport Although properties of diodes having the compounds of the present disclosure applied to the auxiliary light-emitting layers thereof are described in the evaluation results of diode fabrication, the compounds of the present disclosure may be applied to the hole transport layer and both the hole transport layer and the auxiliary light-emitting layer.

The above description is merely illustrative of the present disclosure, and those skilled in the art will appreciate that various modifications can be made without departing from the essential features of the present disclosure. Accordingly, the embodiments disclosed herein are not intended to limit the present invention but to describe the present invention, and the spirit and scope of the present invention are not limited by these embodiments. The scope of protection of the present invention should be interpreted by the following claims, and all descriptions within the equivalent scope should be construed as being included in the scope of the present invention.

The invention claimed is:

1. A compound represented by the following Chemical Formula 1:

<Chemical Formula 1>

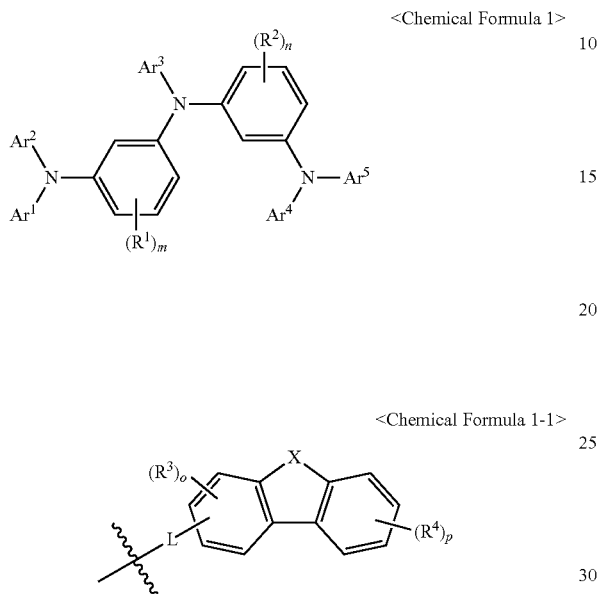

<Chemical Formula 1-1> wherein,
1) $Ar^1$ to $Ar^5$, which are same or different, are each independently one selected from the group consisting of a $C_6$-$C_{60}$ aryl group; a substituent represented by Chemical Formula 1-1; a fluorenyl group; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; and a $C_6$-$C_{30}$ aryloxy group,
with a proviso that at least one of $Ar^1$ to $Ar^5$ is a substituent represented by Chemical Formula 1-1,
2) $R^1$ to $R^4$ are each independently on selected from the group consisting of hydrogen; deuterium; a $C_6$-$C_{60}$ aryl group; a fluorenyl group; a $C_2$-$C_{60}$ hetero ring group bearing at least one hetero atom of O, N, S, Si, and P as a ring member; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; and a $C_6$-$C_{30}$ aryloxy group, wherein multiple $R^3$'s or multiple $R^4$'s can combine with each other to form an aromatic or a heteroaromatic ring,
3) m, n, and p are each independently an integer of 0 to 4, with a proviso that when m, n, and p are each 2 or greater, the multiple $R^1$'s, $R^2$'s, and $R^4$'s can each be same or different,
4) o is an integer of 0 to 3, with a proviso that when o is 2 or greater, the $R^3$'s are same or different,
5) X is selected to be $C(R^a)(R^b)$,
wherein $R^a$ and $R^b$ are each independently one selected from the group consisting of a $C_6$-$C_{60}$ aryl group; a fluorenyl group; a $C_2$-$C_{60}$ hetero ring group bearing at least one hetero atom of O, N, S, Si, and P as a ring member; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_2$-$C_{20}$ alkoxyl group; a $C_6$-$C_{30}$ aryloxy group; and a $C_6$-$C_{60}$ arylene group and $R^a$ and $R^b$ can optionally combine with each other to form a spiro compound with the carbon atom bonded thereto,
6) L is one selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ hetero ring group bearing at least one hetero atom of O, N, S, Si, and P as a ring member;

wherein the aryl group, the fluorenyl group, the arylene group, the hetero ring group, the fused ring group, the alkyl group, the alkenyl group, the alkoxy group, and the aryloxy group may each be further substituted with one or more substituents, and each of the one or more substituents is selected from the group consisting of deuterium; halogen; a $C_1$-$C_{20}$ alkyl group or $C_6$-$C_{20}$ aryl group-substituted or unsubstituted silane group; a siloxane group; a $C_1$-$C_{20}$ alkylthio group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a deuterium-substituted $C_6$-$C_{20}$ aryl group; a fluorenyl group; a $C_2$-$C_{20}$ hetero ring group; a $C_3$-$C_{20}$ cycloalkyl group; a $C_7$-$C_{20}$ arylalkyl group; and a $C_8$-$C_{20}$ arylalkenyl group, wherein the substituents may combine with each other to form a ring wherein the term "ring" refers to a $C_3$-$C_{60}$ aliphatic ring, a $C_6$-$C_{60}$ aromatic ring, a $C_2$-$C_{60}$ hetero ring, or a fused ring group consisting of a combination thereof whether it is saturated or unsaturated.

2. The compound of claim 1, wherein Chemical Formula 1 is expressed as one of the following Chemical Formulas 2 to 7:

<Chemical Formula 2>

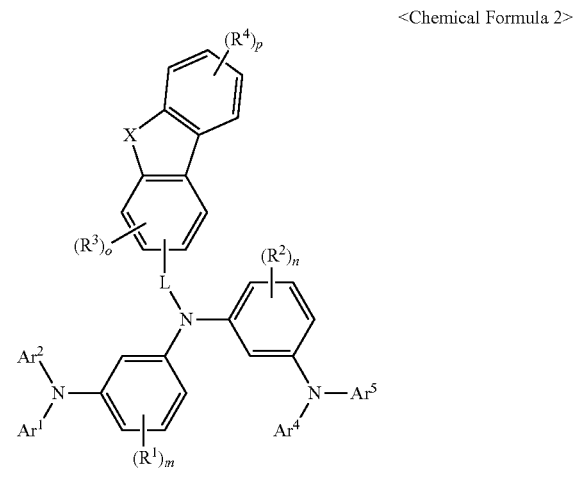

<Chemical Formula 3>
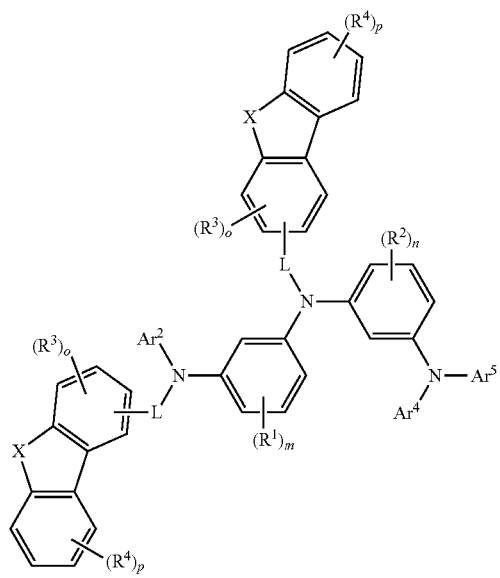
<Chemical Formula 4>
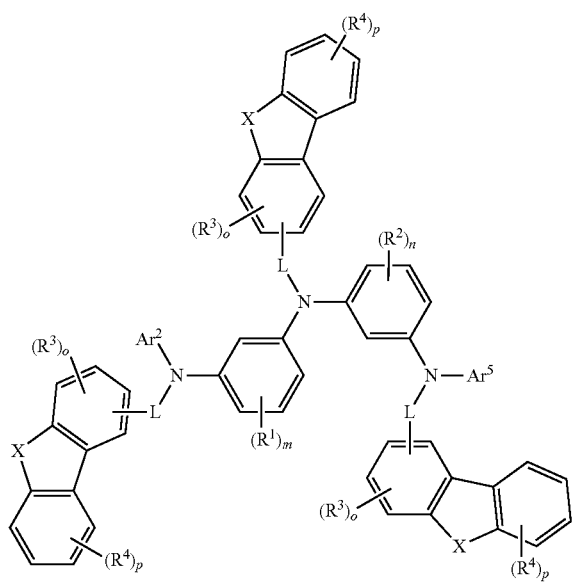
<Chemical Formula 5>
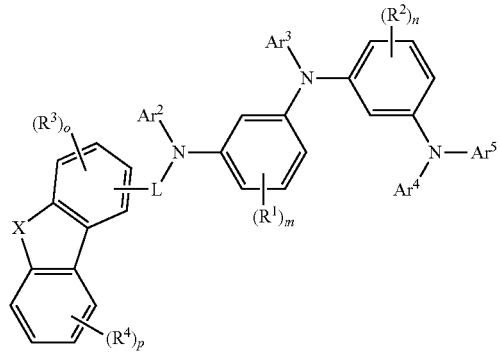
<Chemical Formula 6>
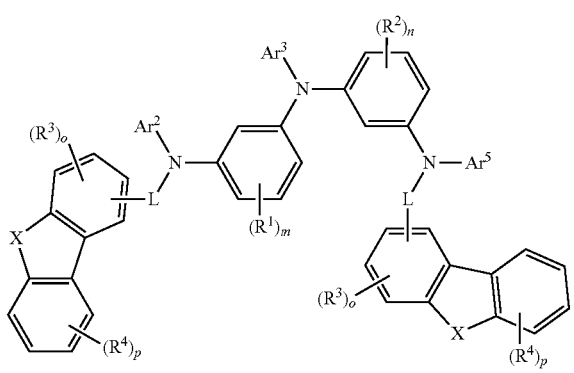
<Chemical Formula 7>
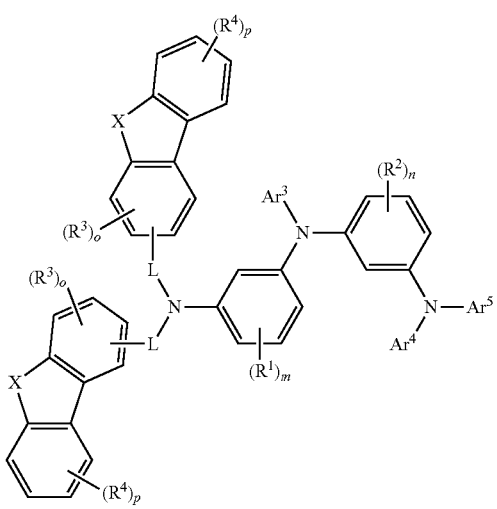
wherein X, Ar¹ to Ar⁵, L, R¹ to R⁴, m, n, o, and p are as defined for X, Ar¹ to Ar⁵, L, R¹ to R⁴, m, n, o, and p in Chemical Formula 1.
3. The compound of claim 1, wherein L is a single bond.
4. The compound of claim 1, being any one of the compounds represented as follows:

123 124
P-1 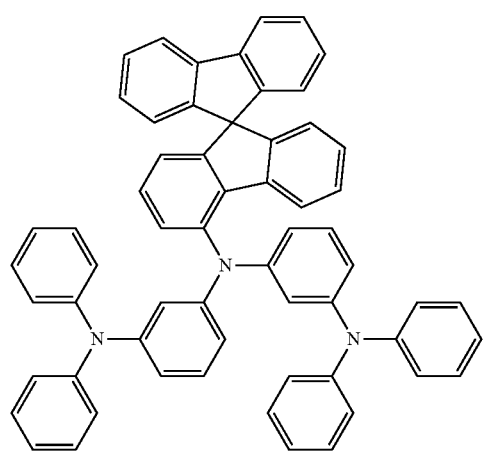 P-2 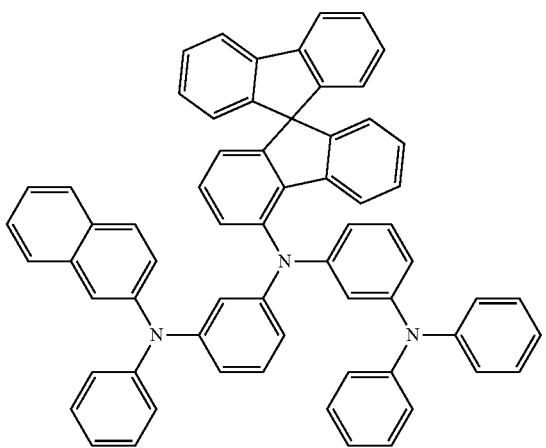
P-3 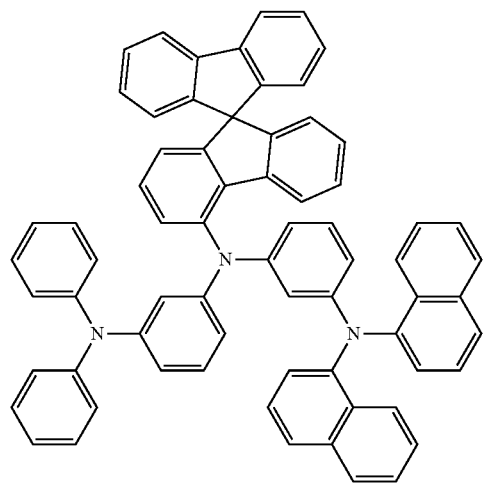 P-4 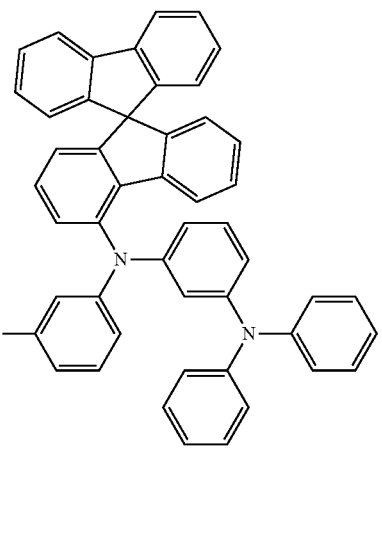
P-5 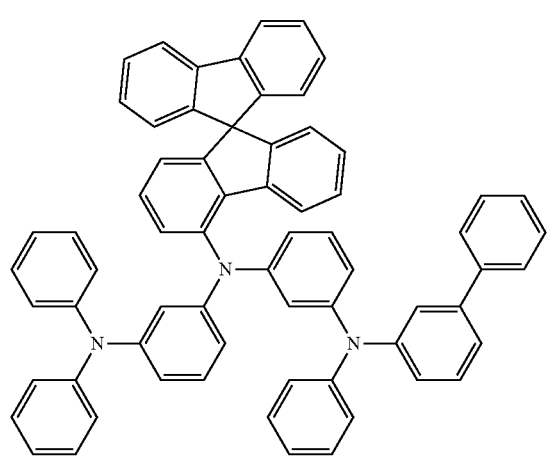 P-6 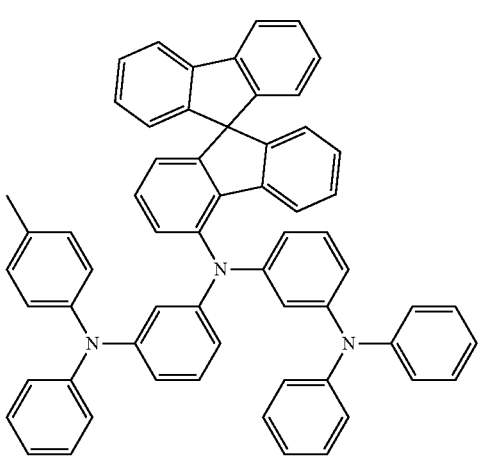

-continued
P-7
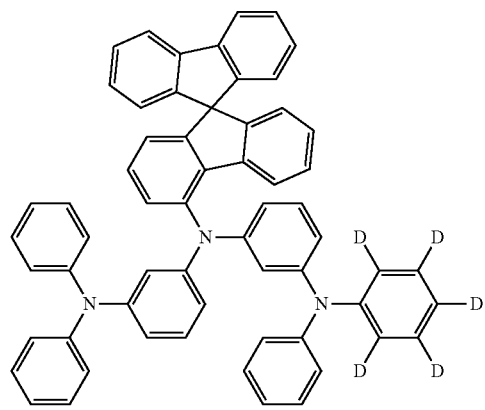
P-8
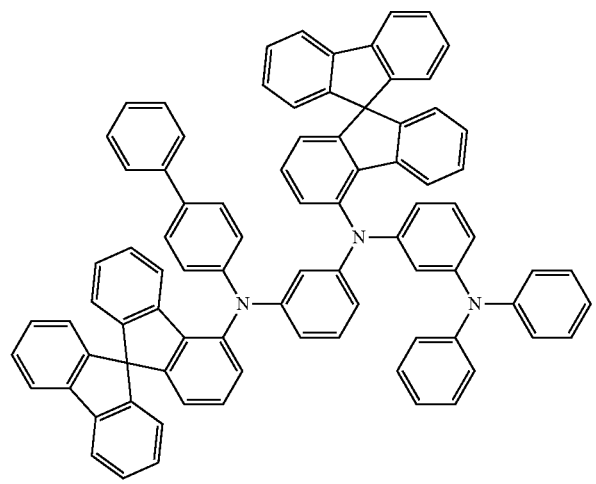
P-9
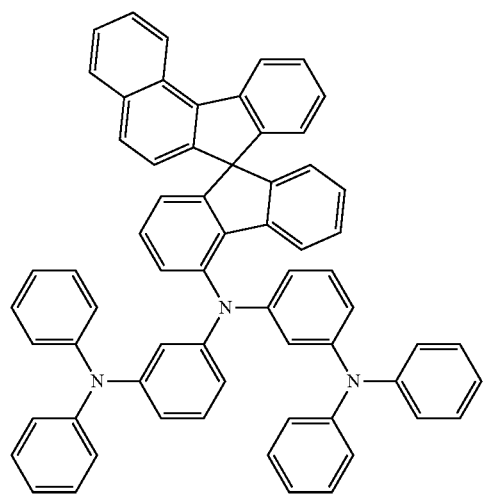
P-10
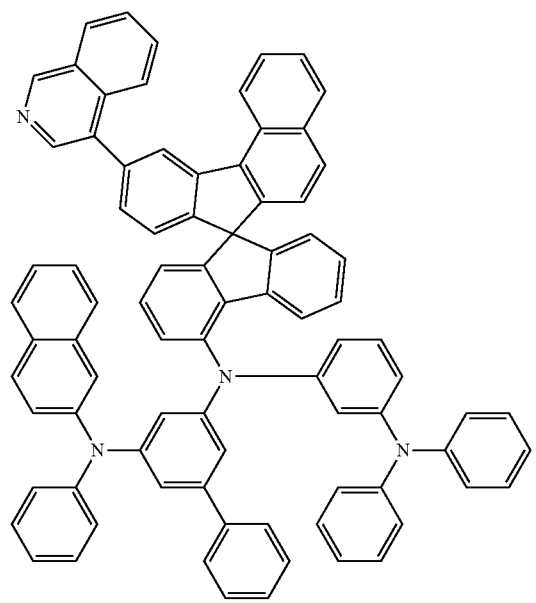
P-11
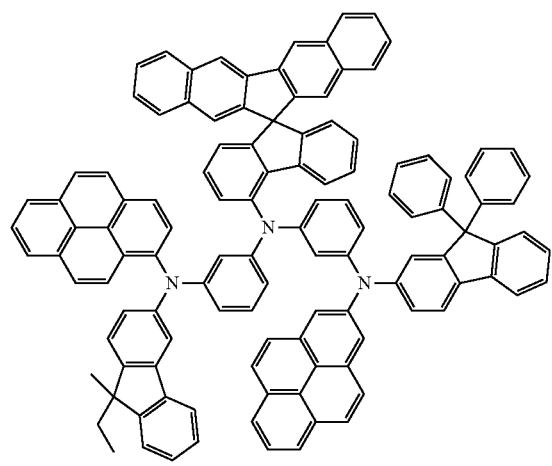
P-12
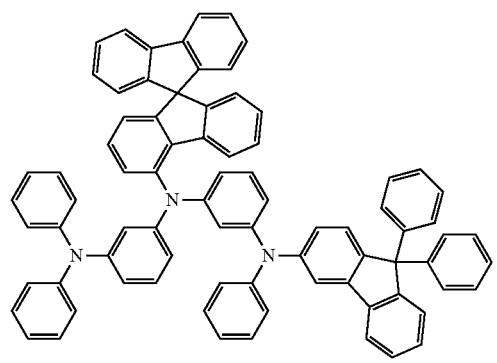

-continued
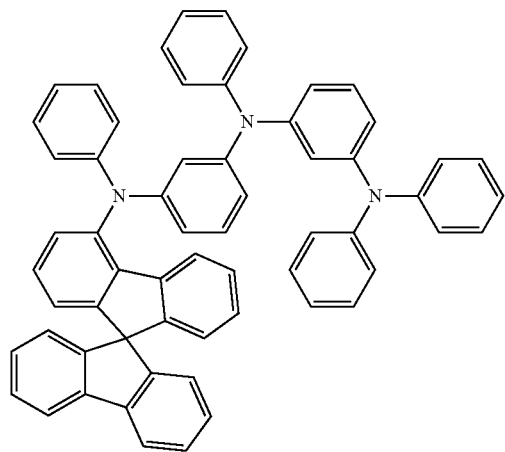
P-14
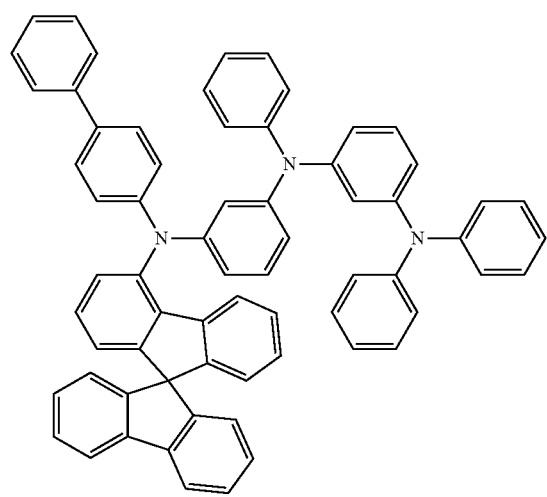
P-15
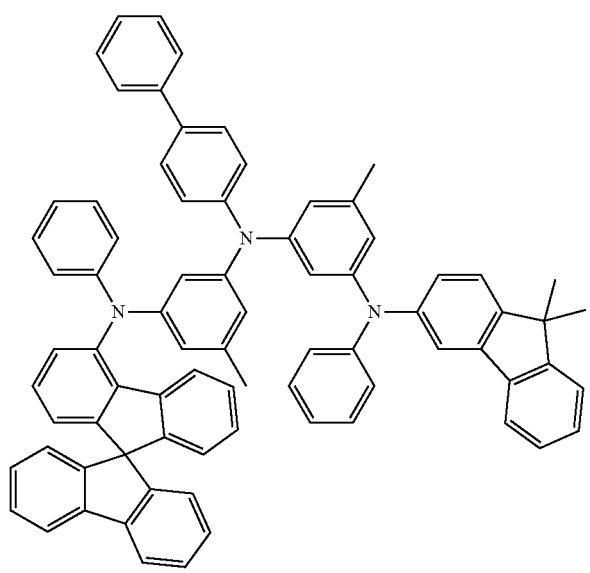
P-16
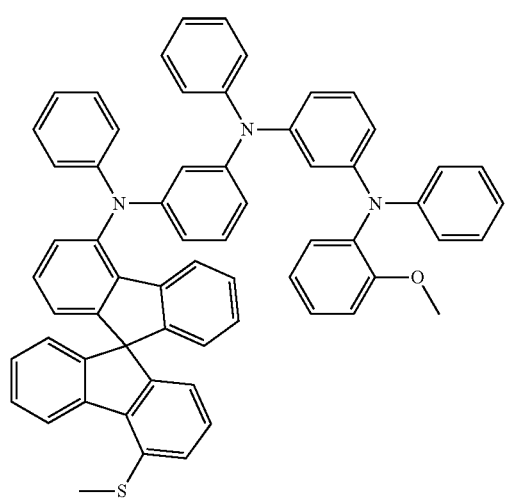
P-17
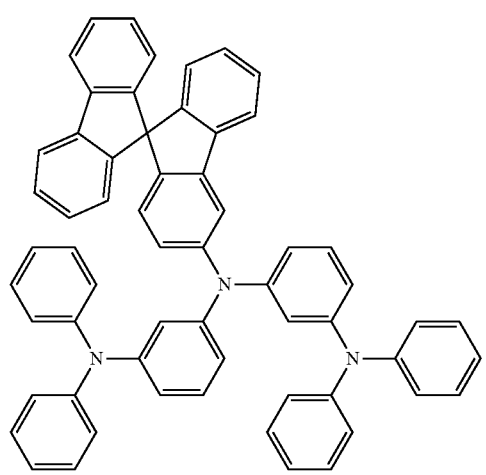
P-18

-continued
P-19
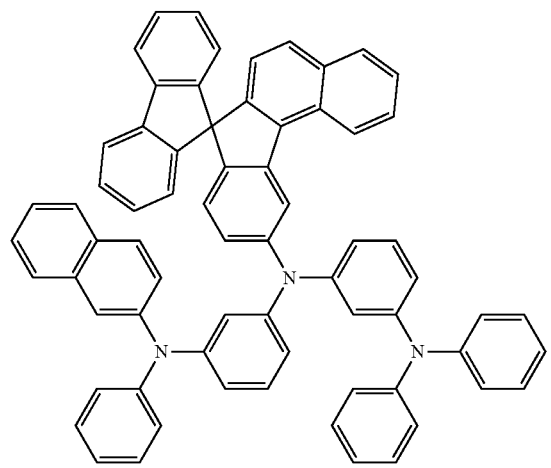
P-20
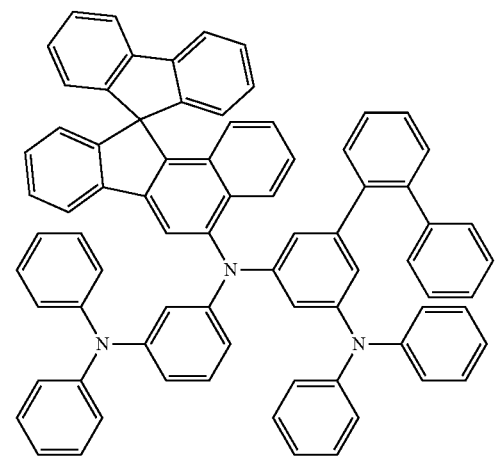
P-21
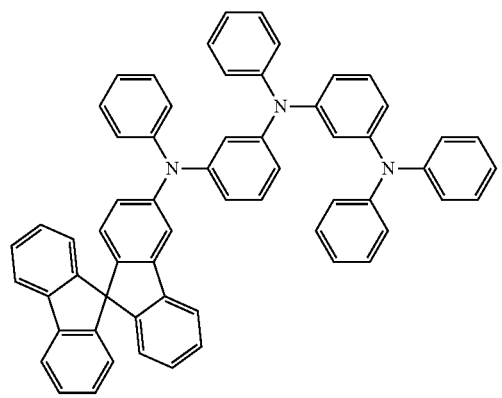
P-22
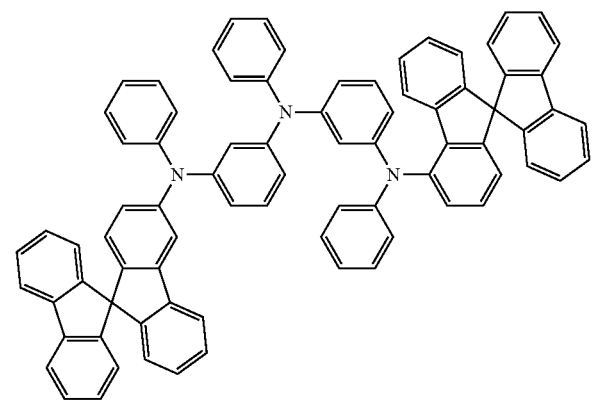
P-23
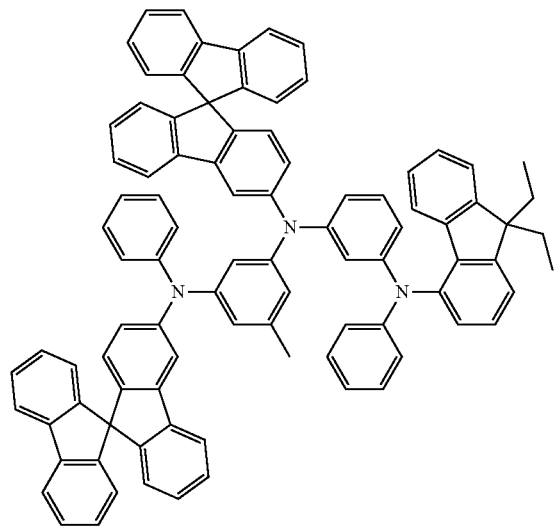
P-24
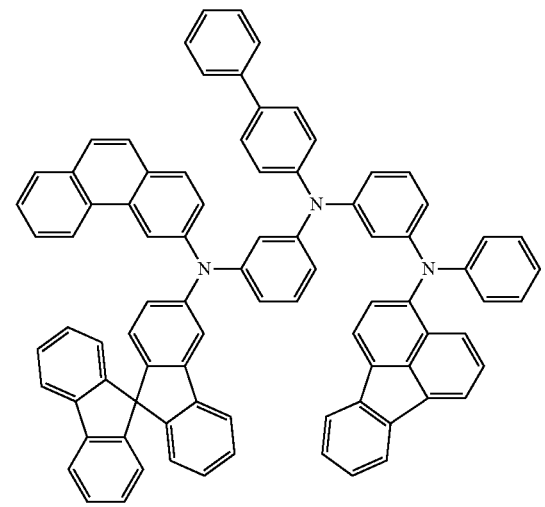

-continued
P-25
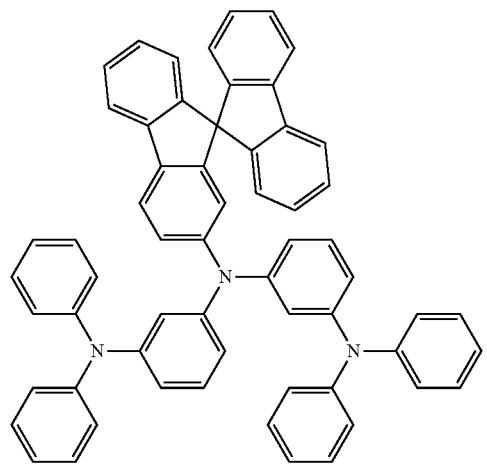
P-26
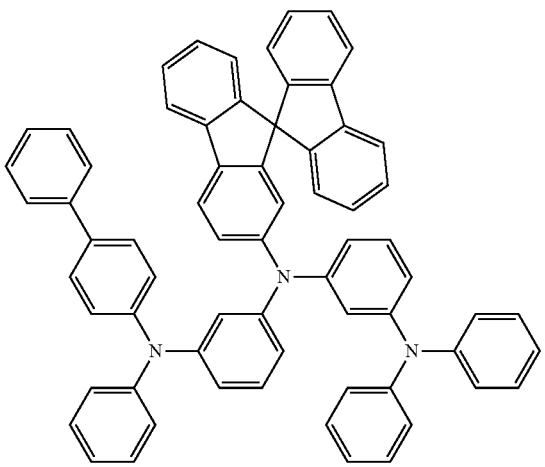
P-27
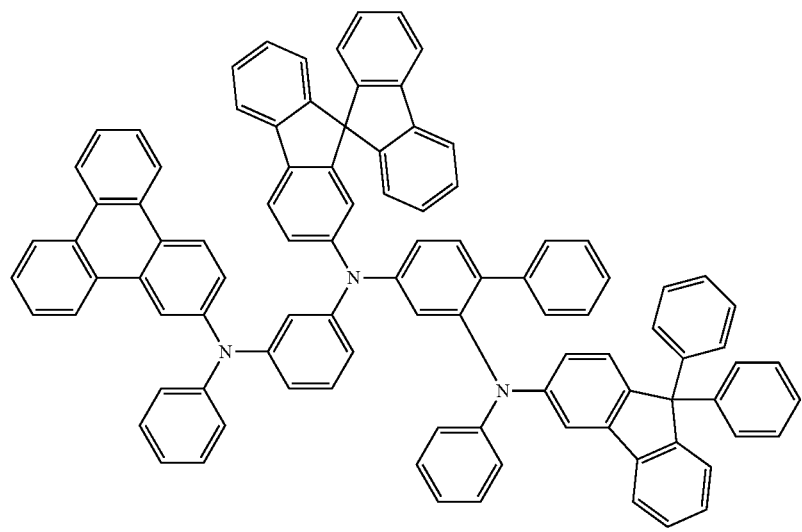
P-28
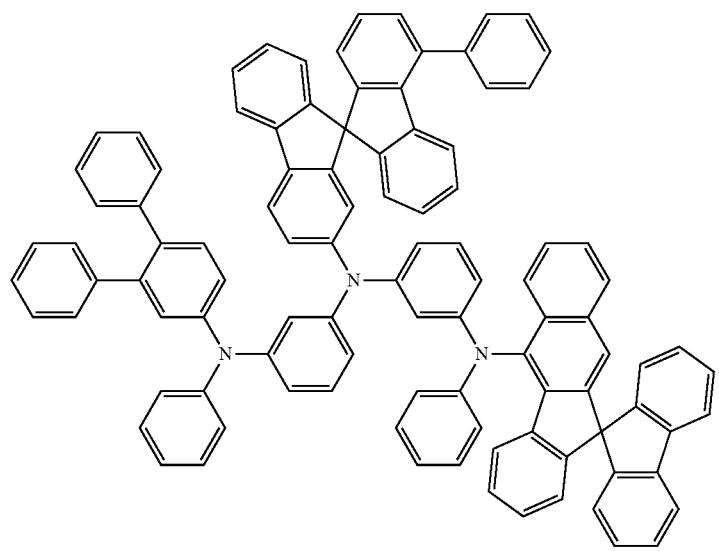

-continued
P-29
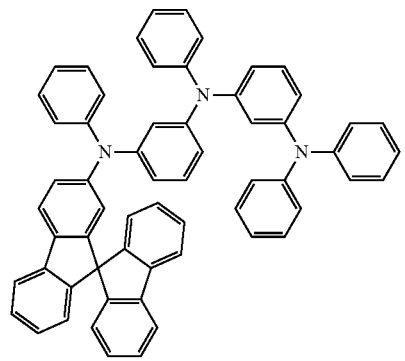
P-30
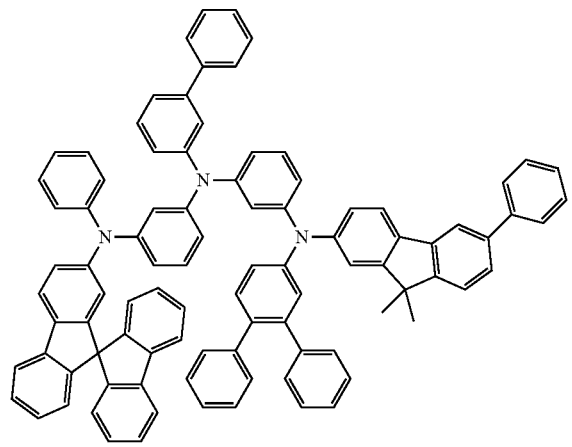
P-31
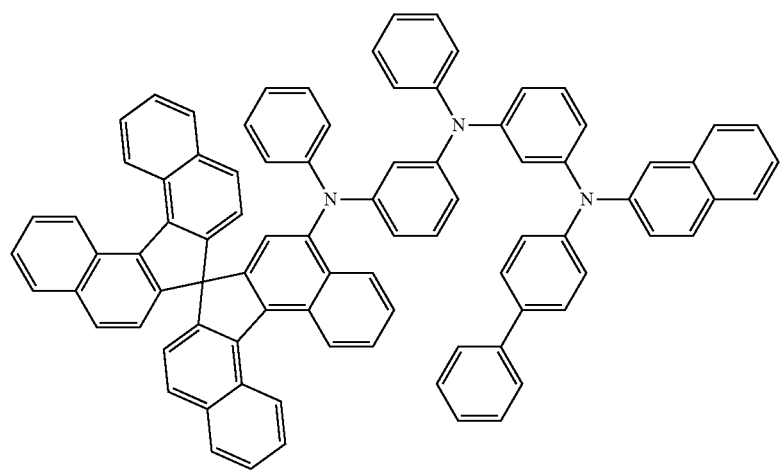
P-32
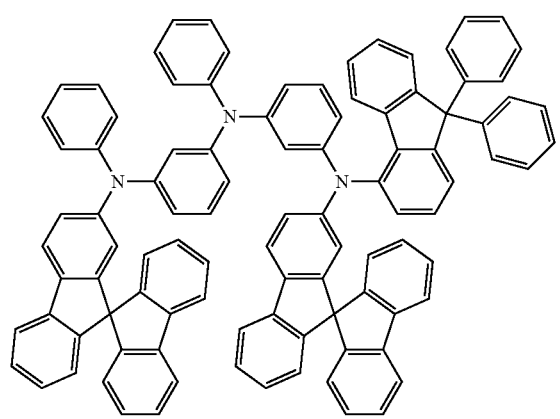
P-33
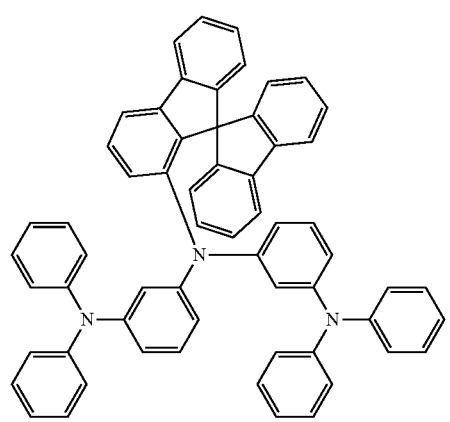

-continued
P-34
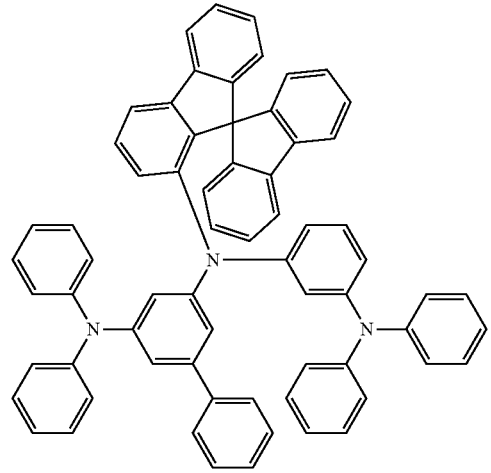
P-35
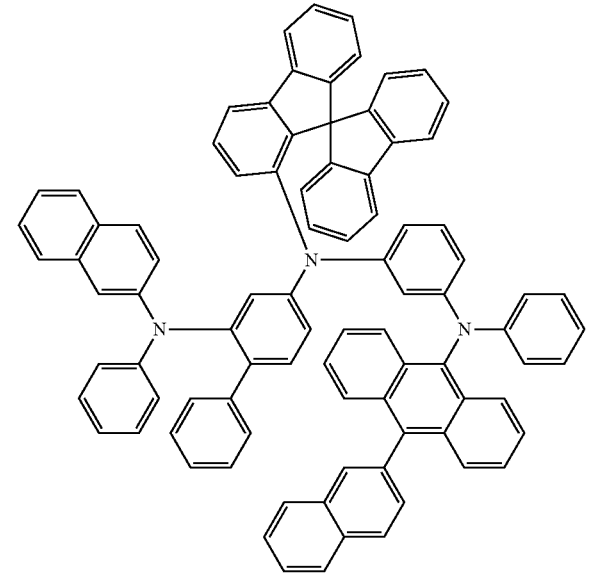
P-36
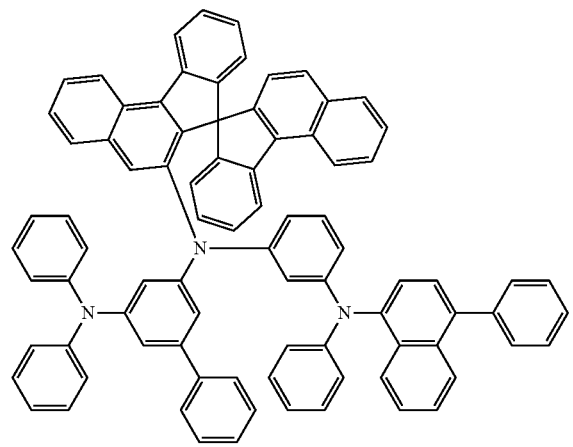
P-37
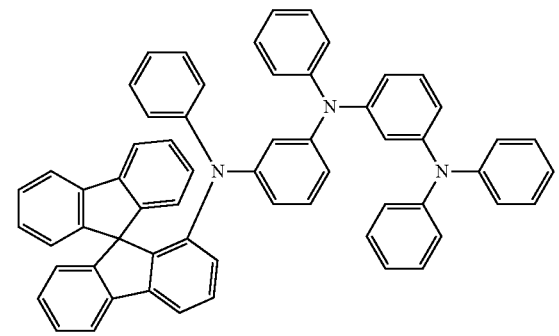
P-38
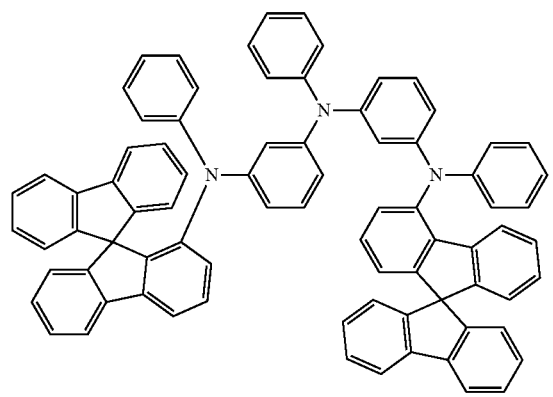
P-39
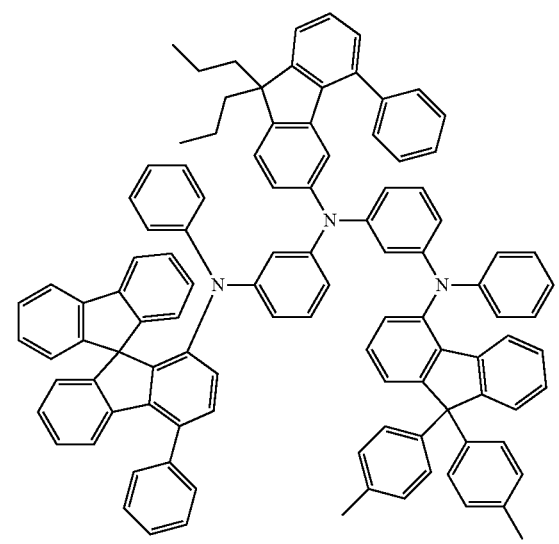

-continued
P-40
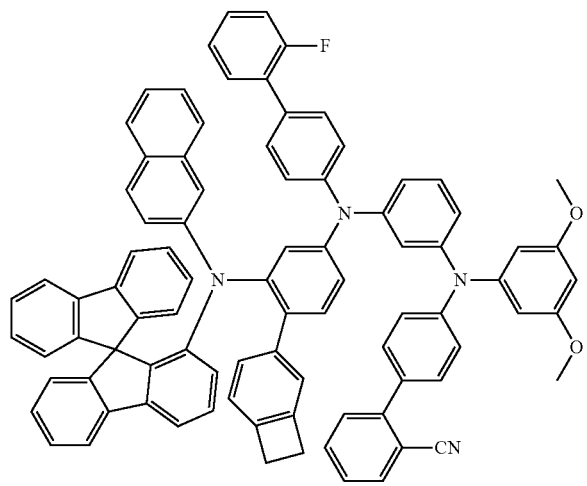
P-41
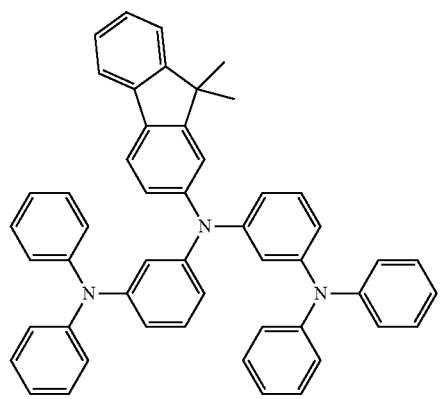 [SMILES: CC1(C)c2ccccc2-c2ccc(N(c3cccc(N(c4ccccc4)c4ccccc4)c3)c3cccc(N(c4ccccc4)c4ccccc4)c3)cc21]
P-42
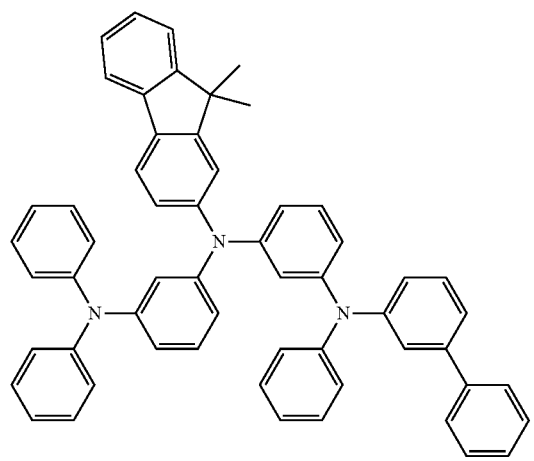
P-43
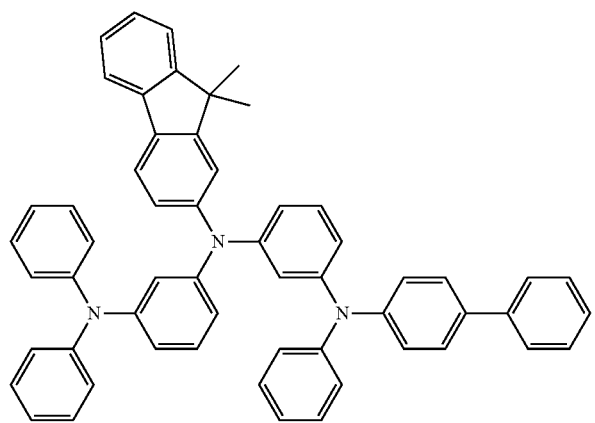
P-44
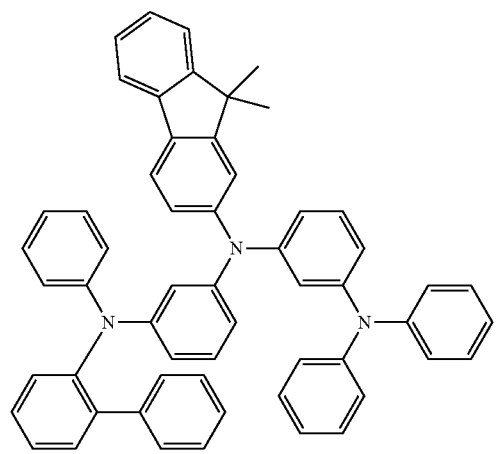
P-45
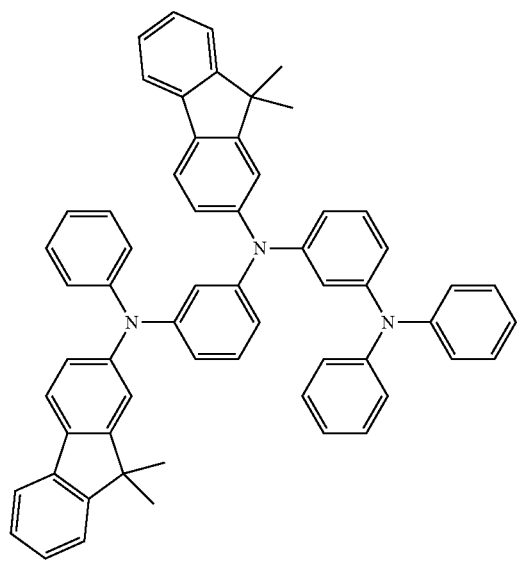

-continued
P-46
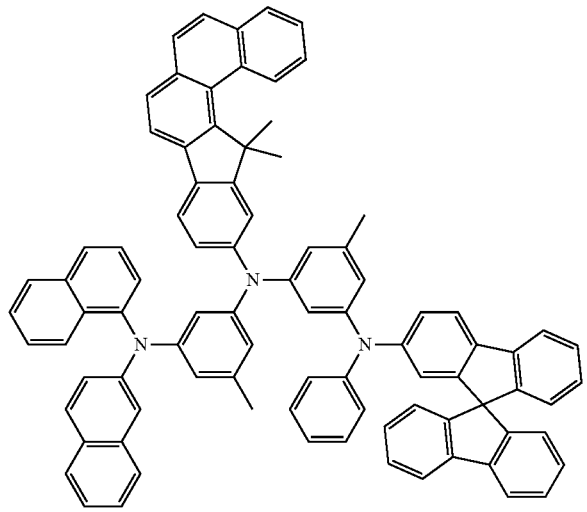
P-47
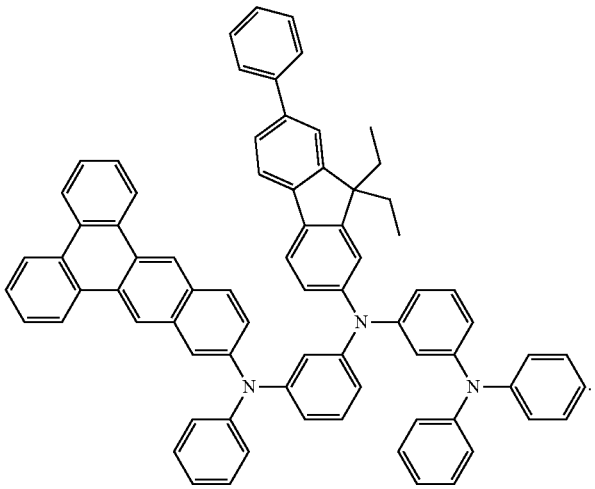
P-49
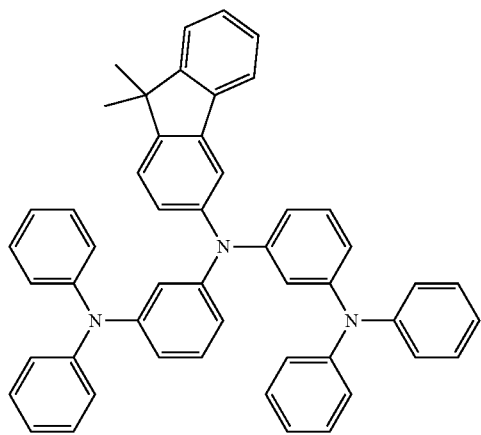
P-50
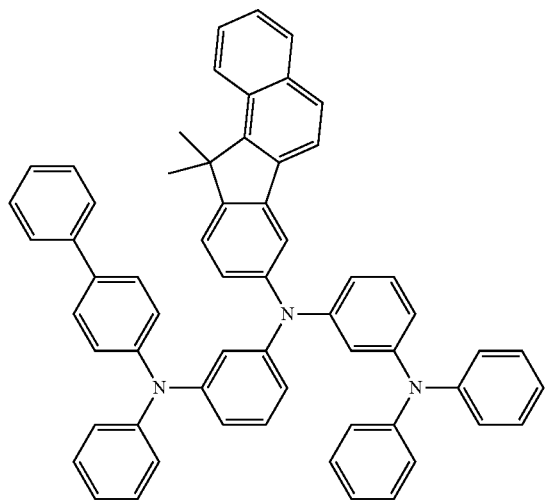
P-51
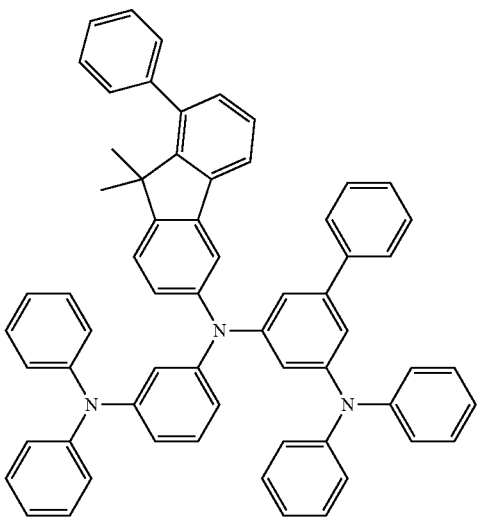

P-52
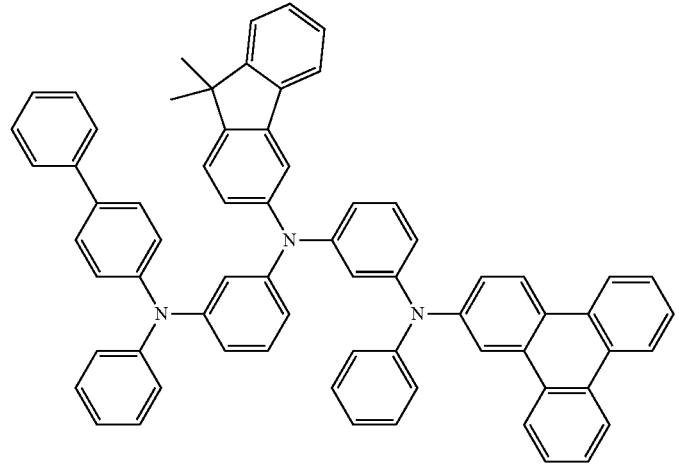
P-53
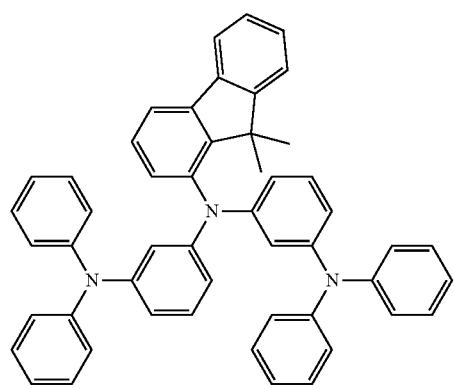
P-54
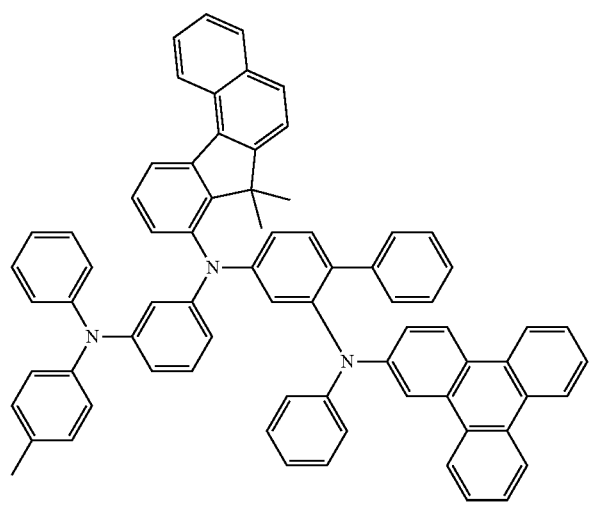
P-55
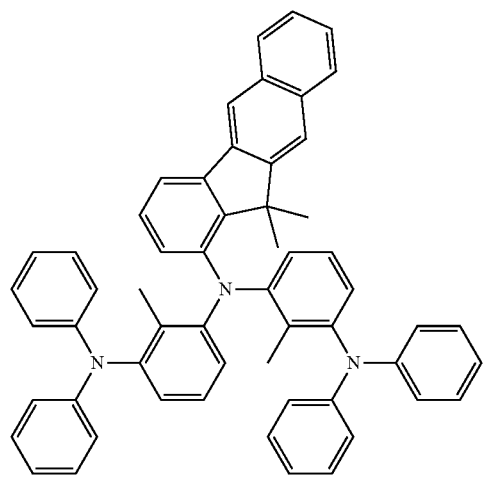
P-56
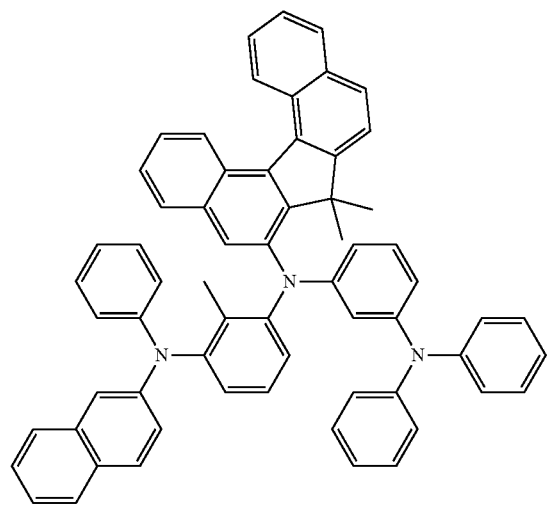

-continued
P-57
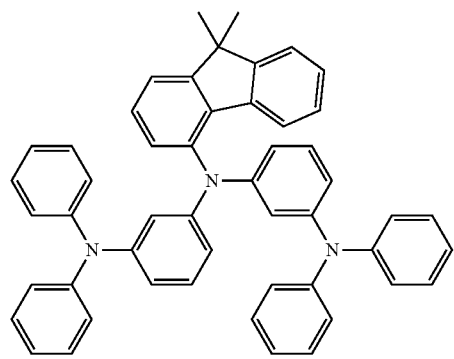
P-58
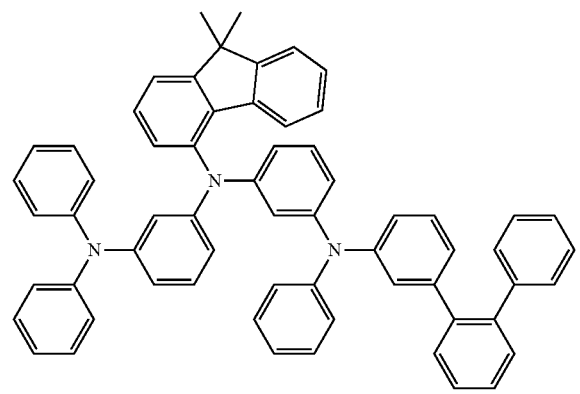
P-59
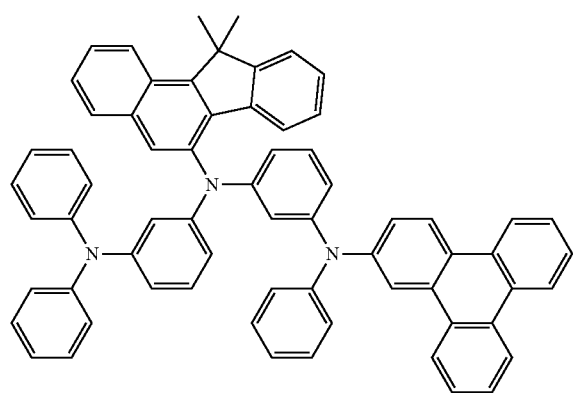
P-60
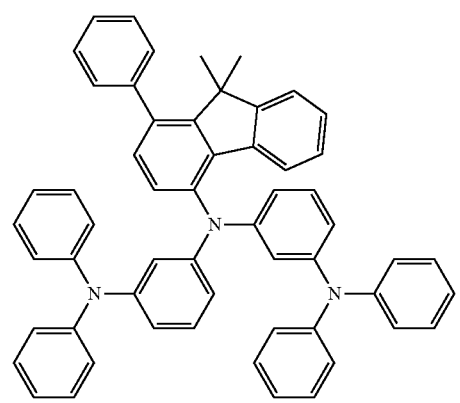
P-61
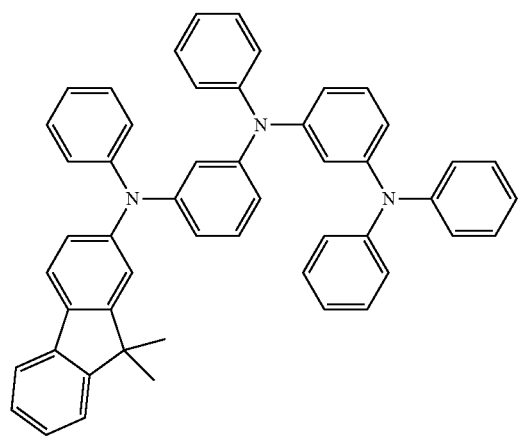
P-62
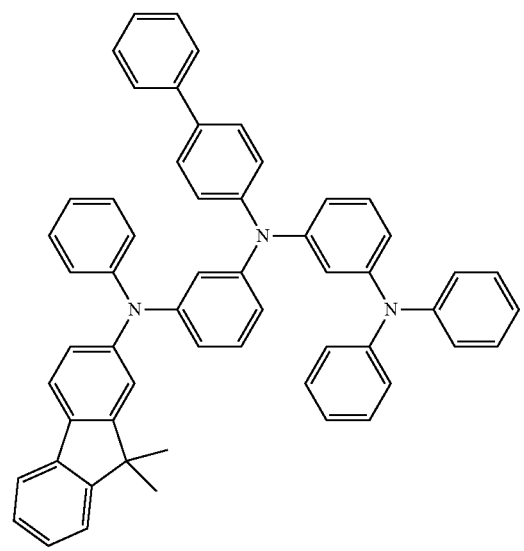

-continued
P-63
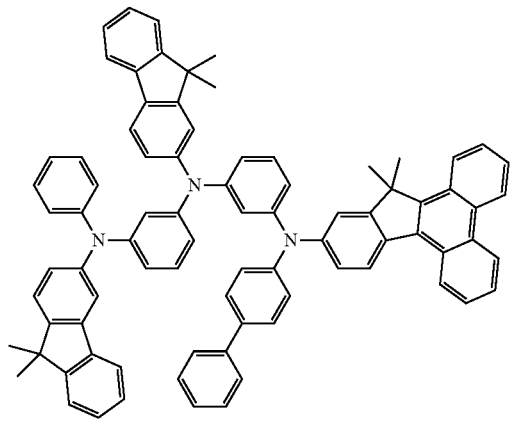
P-64
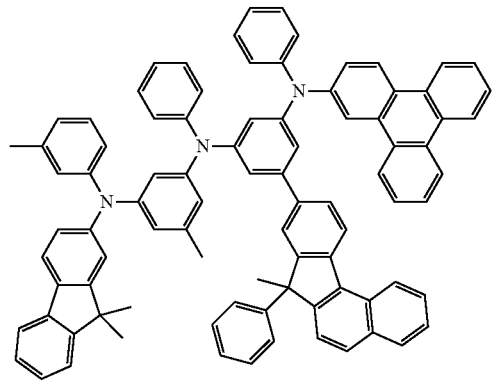
P-65
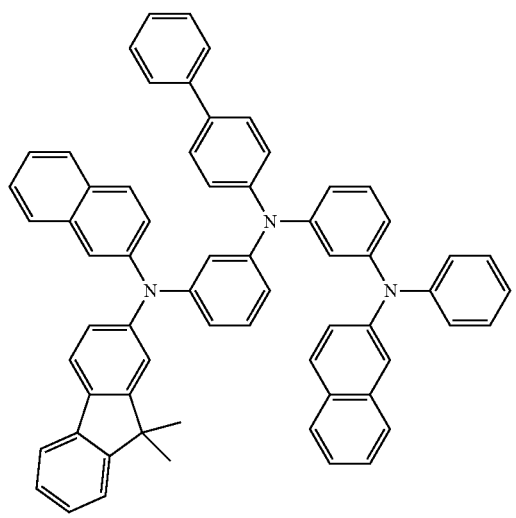
P-66
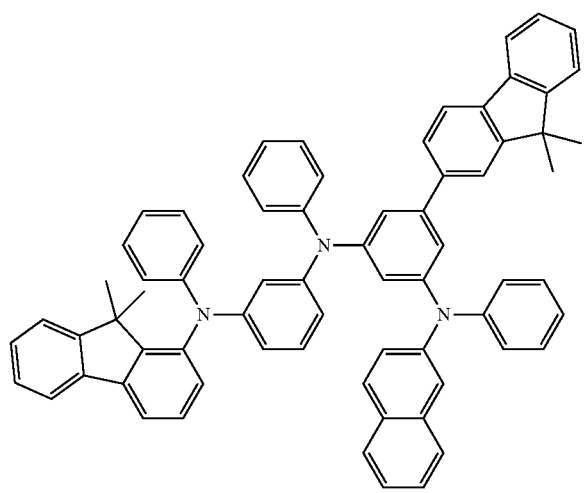
P-67
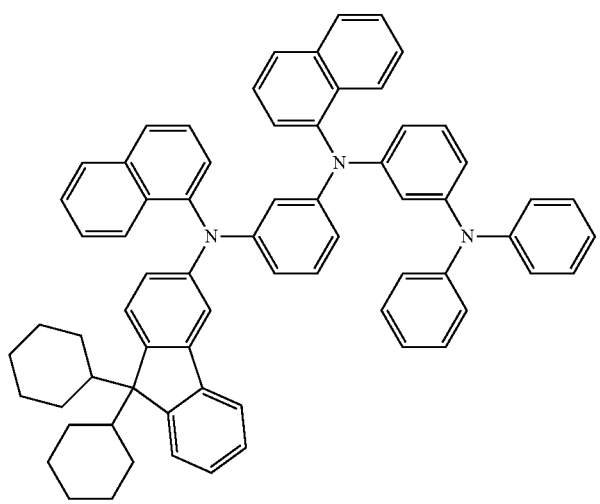
P-68
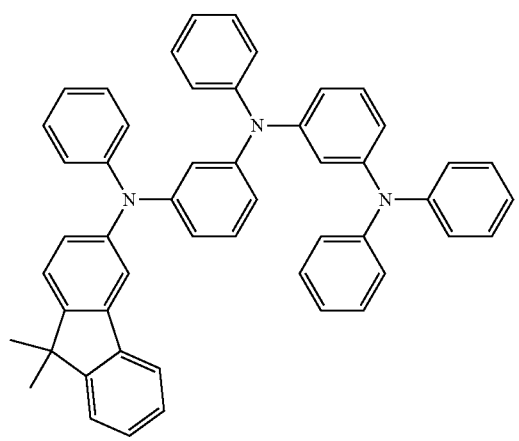

-continued
P-69
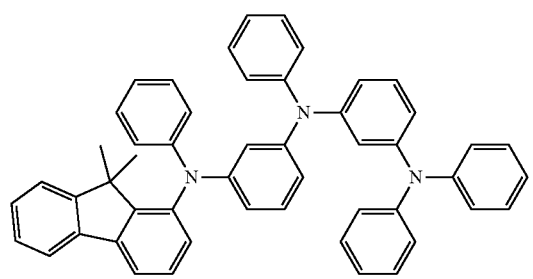
P-70
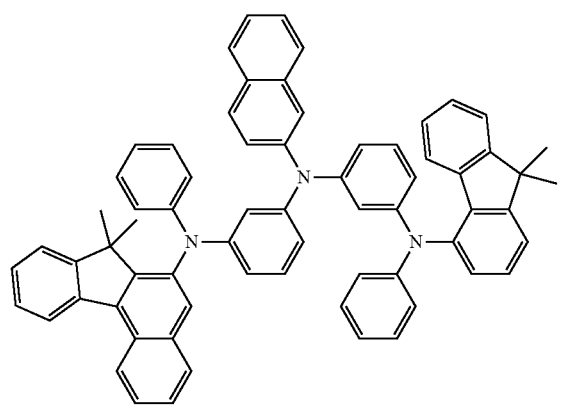
P-71
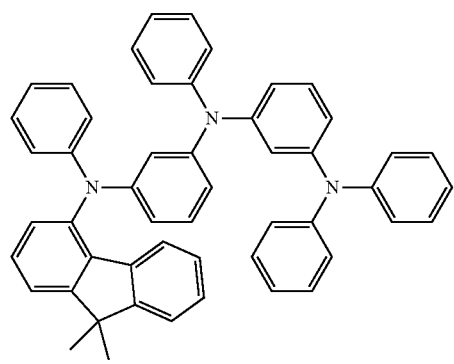
P-72
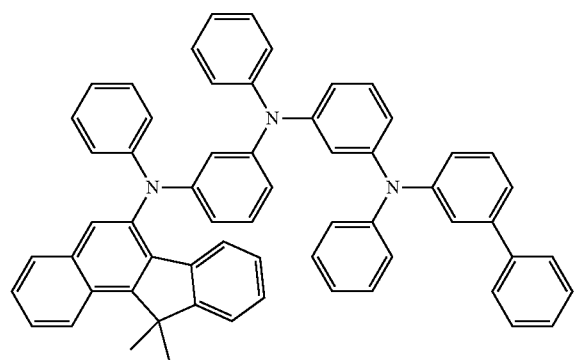
P-73
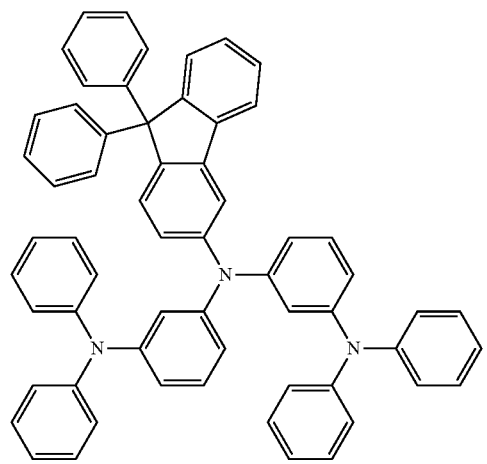
P-74
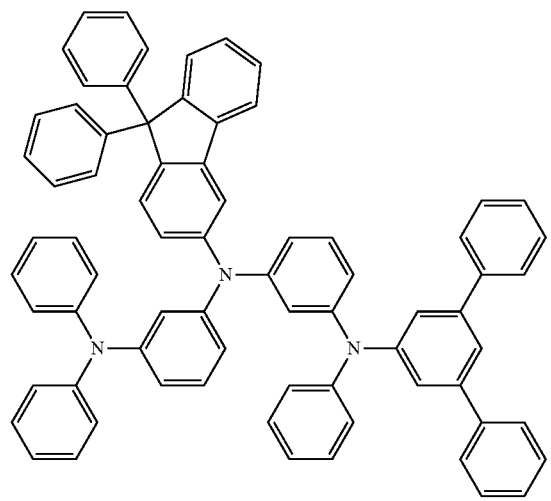

-continued
P-75
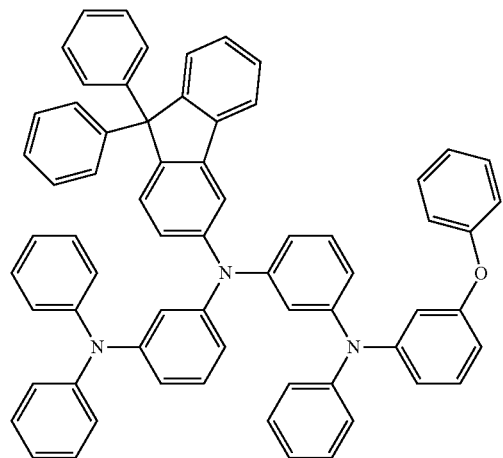
P-76
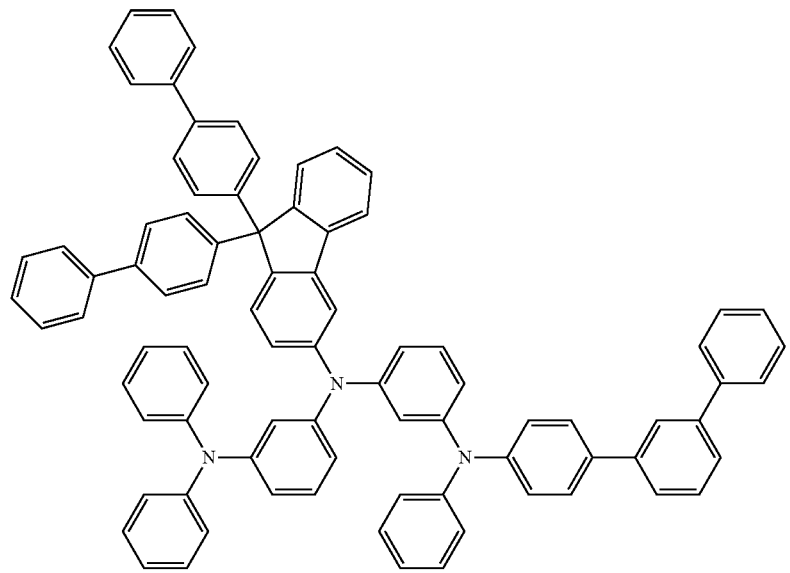
P-77
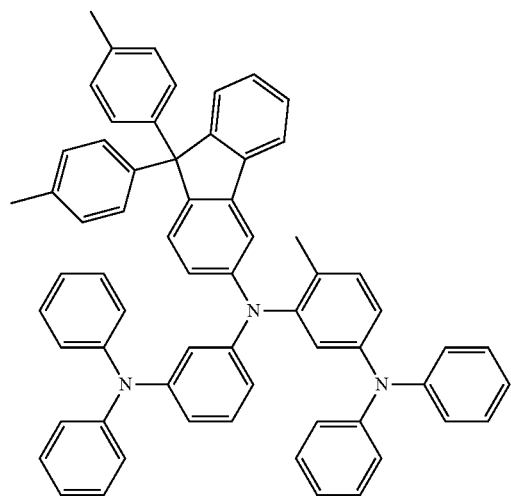
P-78
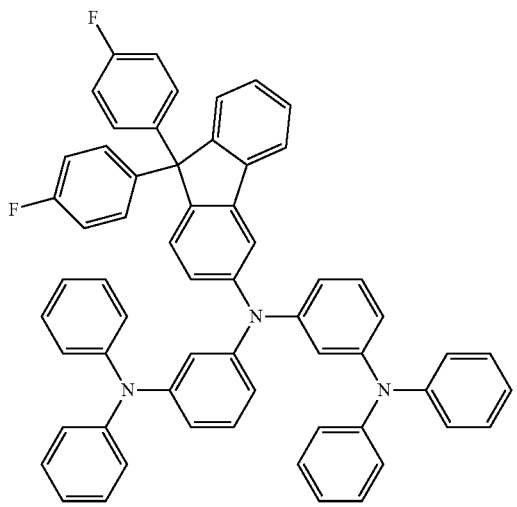

-continued
P-79
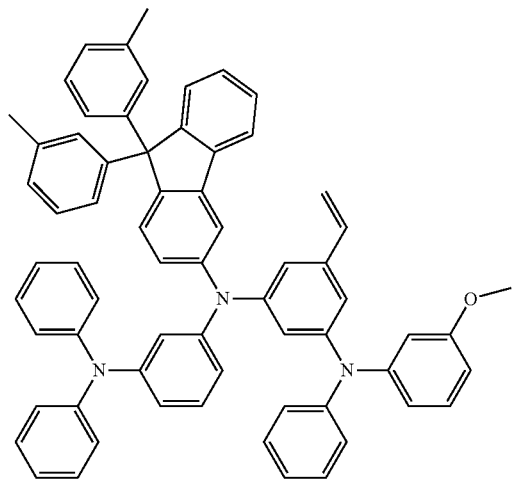
P-80
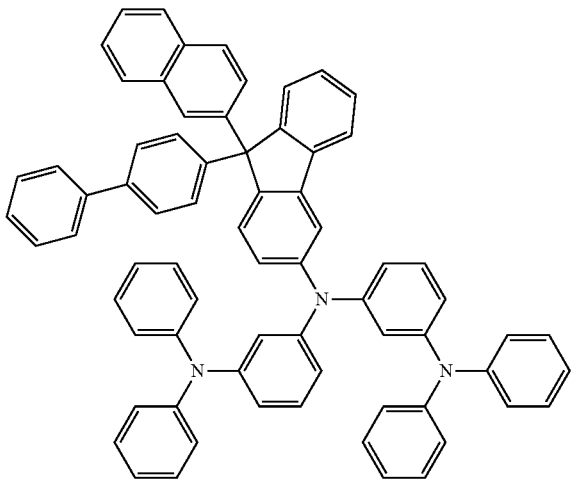
P-81
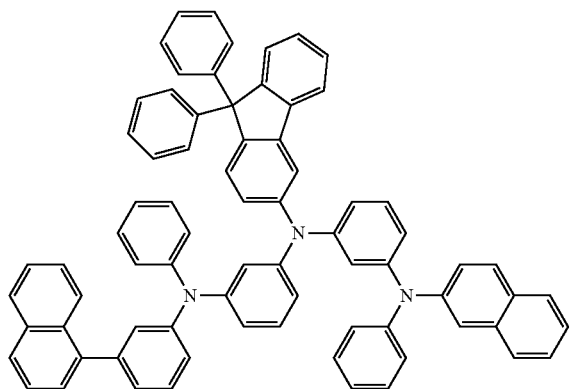
P-82
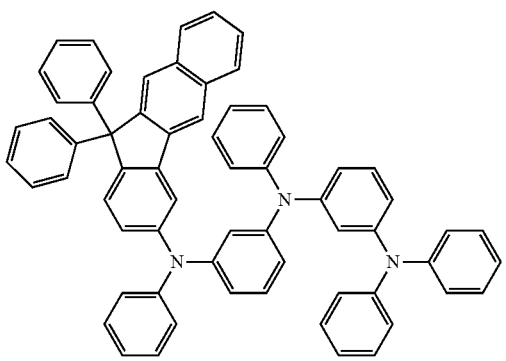
P-83
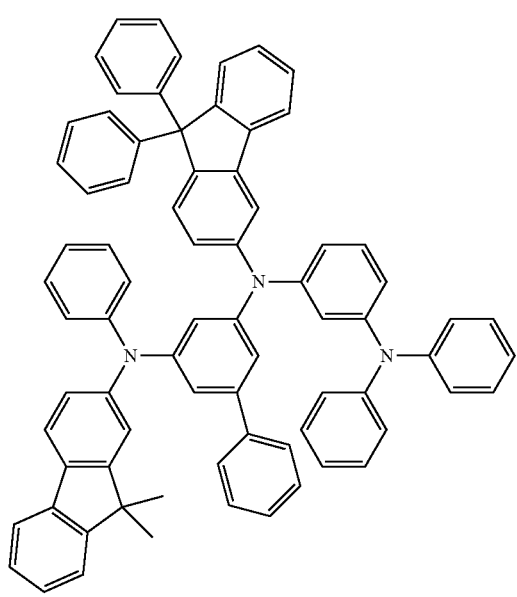
P-84
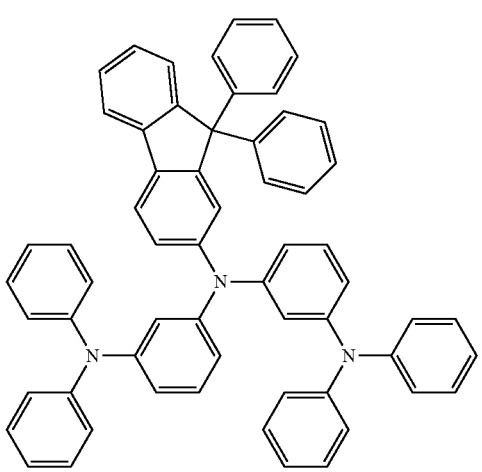

-continued
P-85
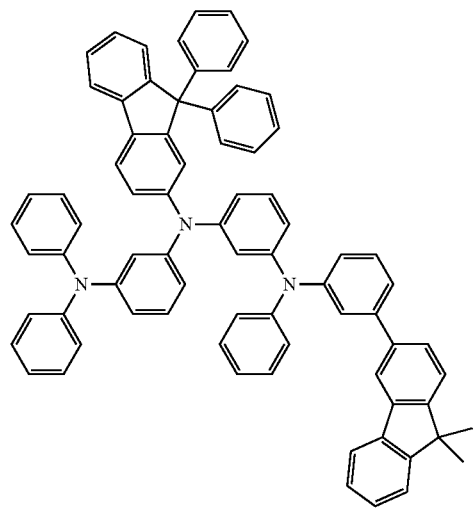
P-86
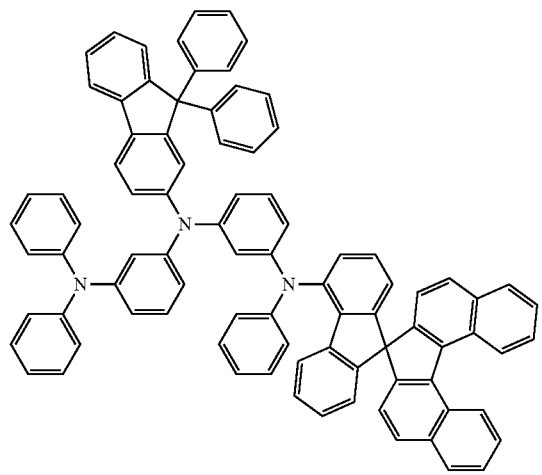
P-87
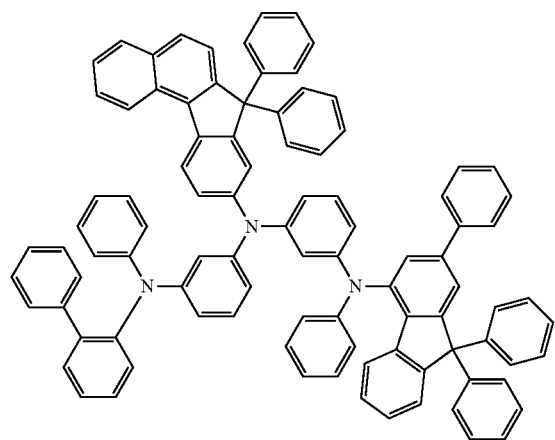
P-88
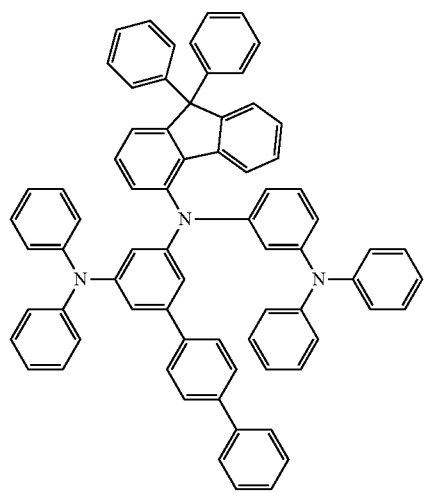
P-89
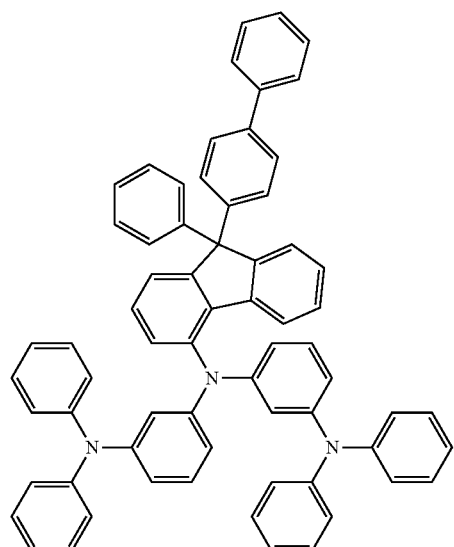
P-90
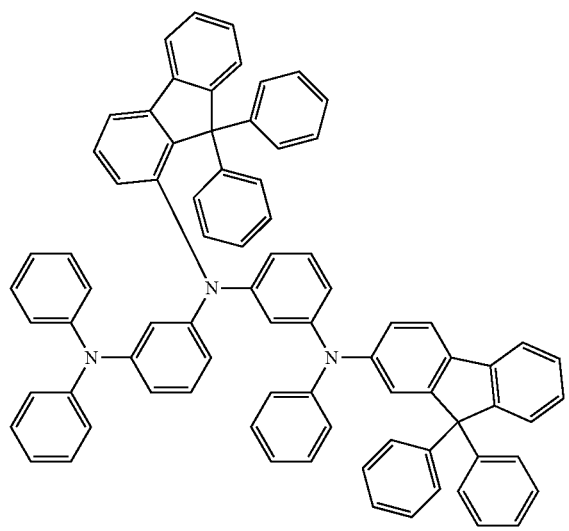

-continued
P-91
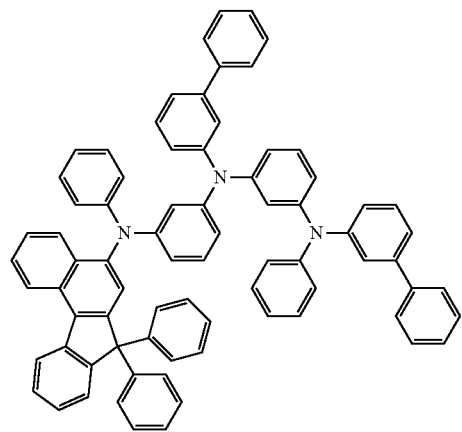
P-92
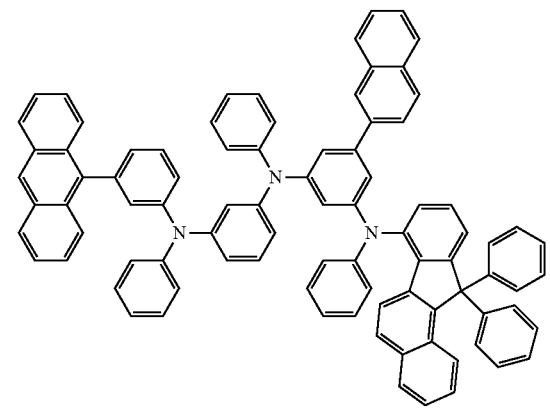
P-93
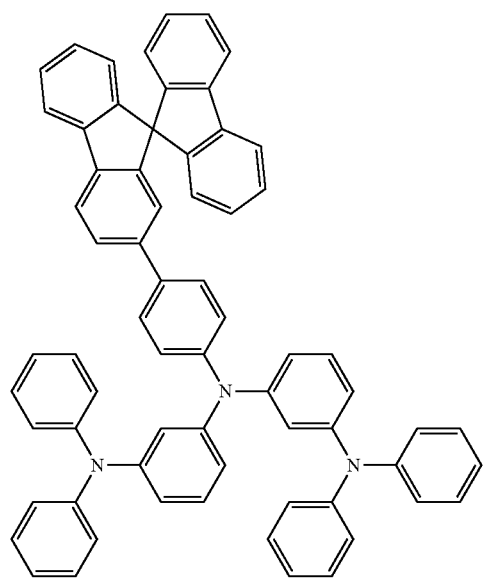
P-94
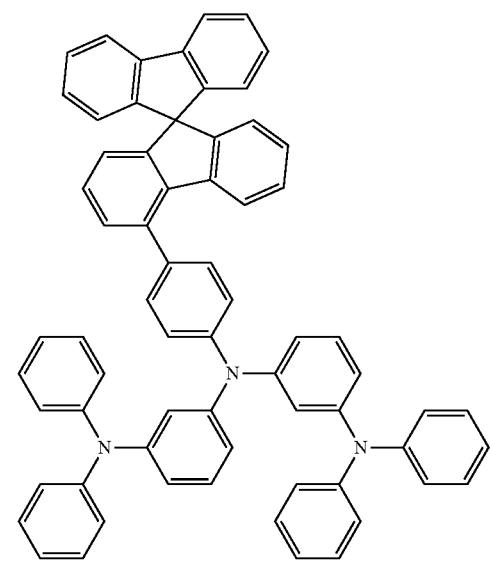
P-95
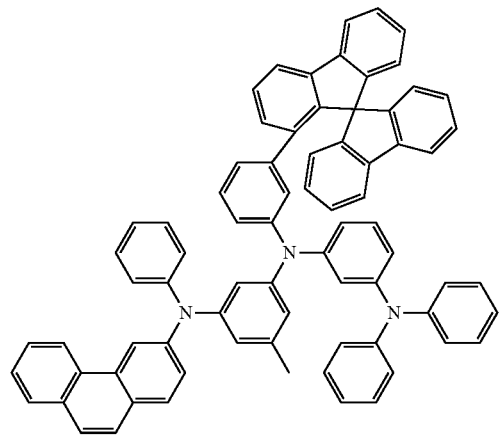
P-96
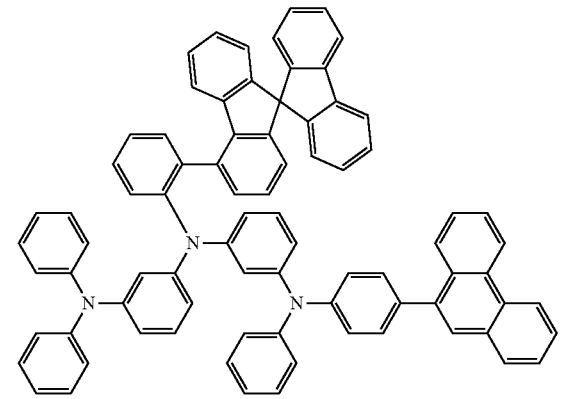

-continued
P-97
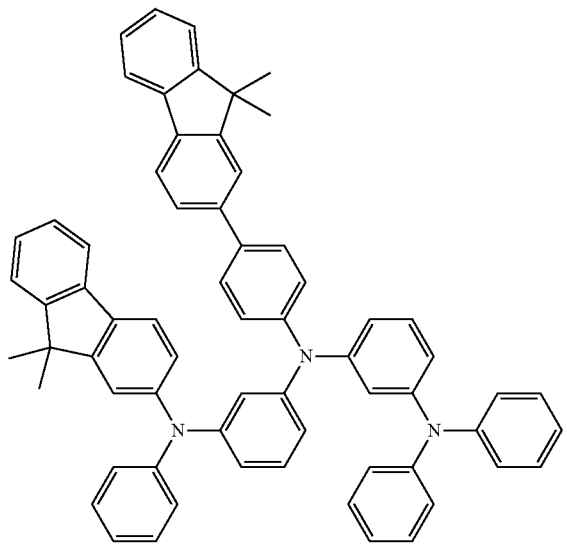
P-98
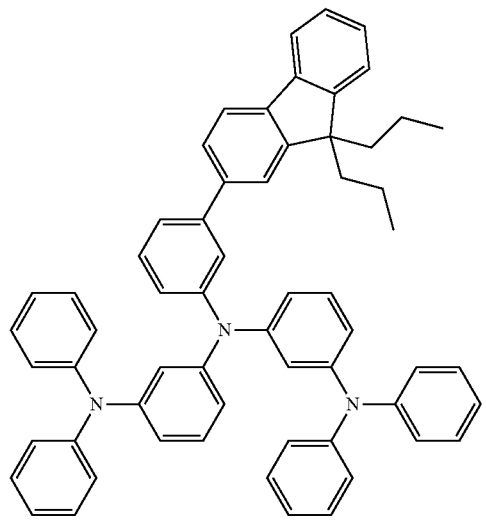
P-99
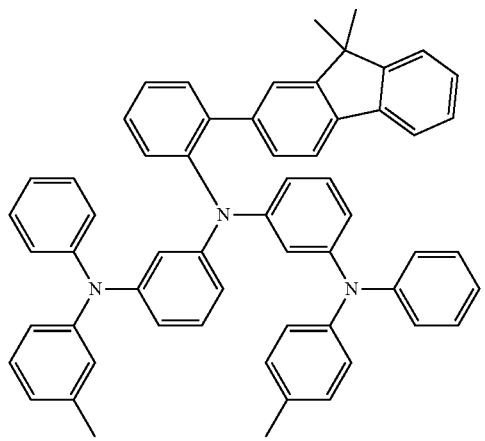
P-100
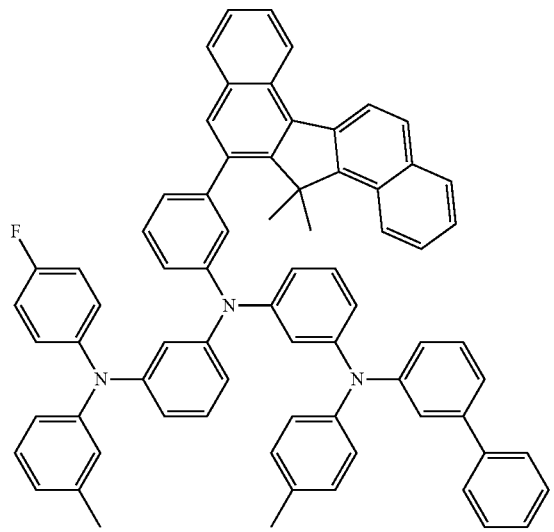
P-101
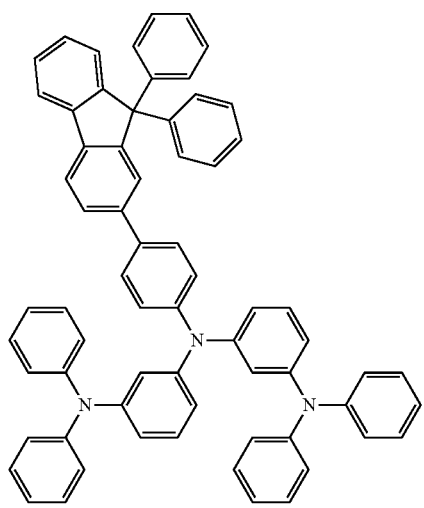
P-102
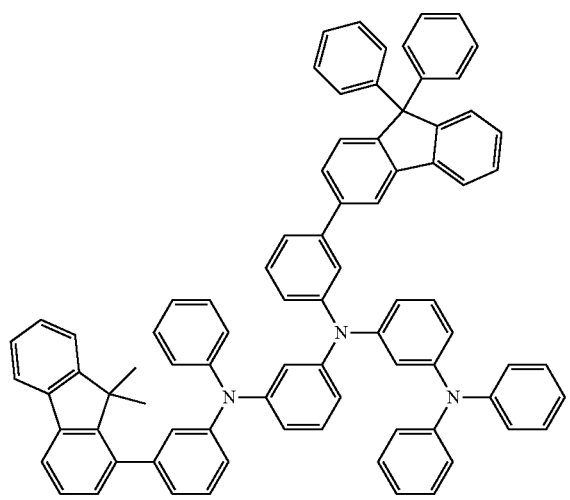

-continued

P-103

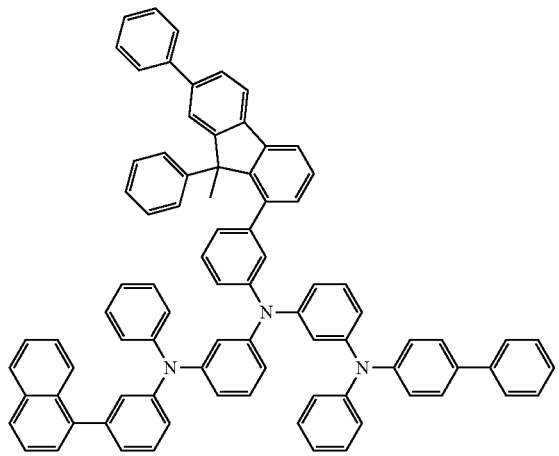

P-104

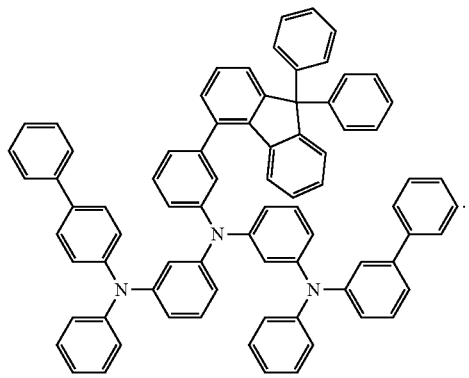

5. An organic electric element, comprising: a first electrode; a second electrode; and an organic layer disposed between the first electrode and the second electrode, wherein the organic layer contains the compound of claim 1.

6. The organic electric element of claim 5, wherein the organic layer is selected from the group consisting of a hole injection layer, a hole transport layer, an auxiliary light-emitting layer, and a light-emitting layer and contains the compound of claim 1.

7. The organic electric element of claim 6, wherein the organic layer is a hole transport layer or an auxiliary light-emitting layer.

8. The organic electric element of claim 5, further comprising a photo-efficiency improving layer formed on at least one of the surfaces of the first electrode and the second electrode, which are located opposite to the organic layer.

9. The organic electric element of claim 5, wherein the organic layer is formed using any one of a spin coating process, a nozzle printing process, an inkjet printing process, a slot coating process, a dip coating process, and a roll-to-roll process.

10. An electronic device, comprising:
   a display device including the organic electric element of claim 5; and
   a control unit for driving the display device.

11. The electronic device of claim 10, wherein the organic electric element is at least one of an organic electroluminescent diode, an organic solar cell, an organic photoconductor, an organic transistor, and a monochromatic or white illumination device.

* * * * *